US009494572B2

(12) United States Patent
Narla et al.

(10) Patent No.: US 9,494,572 B2
(45) Date of Patent: Nov. 15, 2016

(54) METHOD AND COMPOSITIONS FOR TREATING CANCER AND RELATED METHODS

(71) Applicant: Icahn School of Medicine at Mount Sinai, New York, NY (US)

(72) Inventors: Goutham Narla, New York, NY (US); Michael Ohlmeyer, Plainsboro, NJ (US); Matthew David Galsky, New Rochelle, NY (US); Suzanna Katz, New York, NY (US)

(73) Assignee: Icahn School of Medicine at Mount Sinai, New York, NY (US)

( * ) Notice: Subject to any disclaimer, the term of this patent is extended or adjusted under 35 U.S.C. 154(b) by 0 days.

(21) Appl. No.: 14/616,014

(22) Filed: Feb. 6, 2015

(65) Prior Publication Data

US 2015/0224101 A1    Aug. 13, 2015

Related U.S. Application Data

(62) Division of application No. 13/348,173, filed on Jan. 11, 2012, now Pat. No. 9,134,297.

(60) Provisional application No. 61/431,639, filed on Jan. 11, 2011.

(51) Int. Cl.
| | | |
|---|---|---|
| A61K 31/517 | (2006.01) |
| A61K 31/54 | (2006.01) |
| G01N 33/50 | (2006.01) |
| A61K 45/06 | (2006.01) |
| A61K 31/382 | (2006.01) |
| A61K 31/5415 | (2006.01) |
| A61K 31/55 | (2006.01) |
| G01N 33/68 | (2006.01) |

(52) U.S. Cl.
CPC ......... *G01N 33/5008* (2013.01); *A61K 31/382* (2013.01); *A61K 31/517* (2013.01); *A61K 31/5415* (2013.01); *A61K 31/55* (2013.01); *A61K 45/06* (2013.01); *G01N 33/6872* (2013.01); *G01N 2333/485* (2013.01); *G01N 2800/52* (2013.01)

(58) Field of Classification Search
CPC ............. A61K 31/382; A61K 31/517; A61K 31/5415; A61K 31/55; A61K 45/06; G01N 2333/485
USPC ........................... 514/217, 224.8, 266.4, 437
See application file for complete search history.

(56) References Cited

U.S. PATENT DOCUMENTS

| | | |
|---|---|---|
| 5,650,415 A | 7/1997 | Tang et al. |
| 5,656,643 A | 8/1997 | Spada et al. |
| 5,747,498 A | 5/1998 | Schnur et al. |
| 5,789,427 A | 8/1998 | Chen et al. |
| 2005/0137185 A1 | 6/2005 | Lee et al. |
| 2007/0280928 A1 | 12/2007 | Buck et al. |
| 2009/0156523 A1 | 6/2009 | Cho et al. |
| 2010/0239656 A1 | 9/2010 | Astsaturov et al. |

FOREIGN PATENT DOCUMENTS

| | | |
|---|---|---|
| DE | 19629652 | 1/1998 |
| EP | 0361485 | 4/1990 |
| EP | 0566226 | 11/1995 |
| EP | 0520722 | 12/1996 |
| EP | 0682027 | 10/1997 |
| EP | 0837063 | 4/1998 |
| EP | 0787772 | 9/2003 |
| WO | WO 92/20642 | 11/1992 |
| WO | WO 95/09847 | 4/1995 |
| WO | WO 95/19774 | 7/1995 |
| WO | WO 95/19970 | 7/1995 |
| WO | WO 96/30347 | 10/1996 |
| WO | WO 96/31510 | 10/1996 |
| WO | WO 96/33980 | 10/1996 |
| WO | WO 97/02266 | 1/1997 |
| WO | WO 97/03288 | 1/1997 |
| WO | WO 97/13771 | 4/1997 |
| WO | WO 97/19065 | 5/1997 |
| WO | WO 97/27199 | 7/1997 |
| WO | WO 97/30034 | 8/1997 |

(Continued)

OTHER PUBLICATIONS

International Search Report and Written Opinion in International Application No. PCT/US2011/020864, mailed Aug. 15, 2011, 15 pages.
International Preliminary Report on Patentability International Application No. PCT/US2011/020864, mailed Jul. 25, 2013, 12 pages.
International Search Report and Written Opinion in International Application No. PCT/US2012/020922, mailed Apr. 10, 2012, 19 pages.
International Preliminary Report on Patentability International Application No. PCT/US2012/020922, issued Jul. 16, 2013, 10 pages.
Abbott et al., "Search for large extra dimensions in dielectron and diphoton production," Phys Rev Lett., 2001, 86:1156-1161.

(Continued)

*Primary Examiner* — My-Chau T Tran
(74) *Attorney, Agent, or Firm* — Fish & Richardson P.C.

(57) ABSTRACT

The present invention relates to anti-cancer therapeutics. In certain aspects, cancers are treated with a combination of an anti-EGFR agent and an agent that increases the activity of the KLF6 tumor suppressor gene and/or an agent that increases activity of the FOXO1 tumor suppressor gene. In a preferred aspect, the anti-EGFR agent erlotinib a tricyclic agent compound, are used in combination to treat non-small cell lung cancer in a patient with primary or acquired drug resistance to erlotinib, and wherein the tricyclic agent is administered in an amount that does not lead to a substantial central nervous system effect. In additional aspects, the invention relates to compositions and kits useful for treating cancers, methods for screening for compounds that enhance the activity of anti-EGFR agent, and methods for determining whether a patient will respond to anti-EGFR therapy.

10 Claims, 26 Drawing Sheets

(56) References Cited

FOREIGN PATENT DOCUMENTS

| WO | WO 97/30044 | 8/1997 |
|---|---|---|
| WO | WO 97/32880 | 9/1997 |
| WO | WO 97/32881 | 9/1997 |
| WO | WO 97/34895 | 9/1997 |
| WO | WO 97/38983 | 10/1997 |
| WO | WO 97/38994 | 10/1997 |
| WO | WO 97/49688 | 12/1997 |
| WO | WO 98/02434 | 1/1998 |
| WO | WO 98/02437 | 1/1998 |
| WO | WO 98/02438 | 1/1998 |
| WO | WO 98/07726 | 2/1998 |
| WO | WO 98/14449 | 4/1998 |
| WO | WO 98/14450 | 4/1998 |
| WO | WO 98/14451 | 4/1998 |
| WO | WO 98/17662 | 4/1998 |
| WO | WO 98/33798 | 8/1998 |
| WO | WO 99/07701 | 2/1999 |
| WO | WO 99/35132 | 7/1999 |
| WO | WO 99/35146 | 7/1999 |
| WO | WO 01/34574 | 5/2001 |
| WO | WO 2005/027842 | 3/2005 |
| WO | WO 2012/096654 | 7/2012 |

OTHER PUBLICATIONS

Akiyama et al., "Circumvention of Multiple-Drug Resistance in human cancer cells by thioridazine, trifluoperazine, and chlorpromazine," May 1986, 76(5):839-844.

Amos-Landgraf et al., "A target-selected Apc-mutant rat kindred enhances the modeling of familial human colon cancer," PNAS, 2007, 104(10):4036-4041.

Amundadittir et al., "Transgenic mouse models of breast cancer," Breast Cancer Res. Treat., 1996, 39:119-135.

Aoki et al., "Proteasomal degradation of the FoxO1 transcriptional regulator in cells transformed by the P3k and Akt oncoproteins," Proc Natl Acad Sci U S A, 2004, 101:13613-13617.

Appelbaum, "Graft versus leukemia (GVL) in the therapy of acute lymphoblastic leukemia (ALL)," Leukemia, 1997, 11(Suppl. 4):S15-S17.

Bacus, "Biological grading of breast cancer using antibodies to proliferating cells and other markers," Am. J. Pathol., 1989, 135:783-92.

Beer et al., "Gene-expression profiles predict survival of patients with lung adenocarcinoma," Nat Med., 2002, 8:816-824.

Bhattacharjee et al., "Classification of human lung carcinomas by mRNA expression profiling reveals distinct adenocarcinoma subclasses," Proc Natl Acad Sci U S A, 2001, 98:13790-13795.

Bilir et al., "Potentiation of cytotoxicity by combination of imatinib and chlorimipramine in glioma," Intl J Oncol, 2008, 32:829-839.

Blackhall et al., "Erlotinib in non-small cell lung cancer: a review," Expert Opin Pharmacother., Jun. 2005, 6(6):995-1002.

Boehm et al., "Integrative genomic approaches identify IKBKE as a breast cancer oncogene," Cell, 2007, 129:1065-1079.

Booth et al., "Stromal and vascular invasion in an human in vitro bladder cancer model," Lab Invest., 1997, 76:843-857.

Boulikas, "Gene therapy of prostate cancer: p53, suicidal genes, and other targets," Anticancer Res., 1997, 17:1471-1506.

Camacho-Vanegas et al., "Functional inactivation of the KLF6 tumor suppressor gene by loss of heterozygosity and increased alternative splicing in glioblastoma," Int J Cancer, 2007, 121:1390-1395.

Campana et al., "Double and triple staining methods for studying the proliferative activity of human B and T lymphoid cells," J. Immunol. Meth., 1988, 107:79-88.

Carbo et al., "Interleukin-15 antagonizes muscle protein waste in tumour-bearing rats," Br J Cancer, 2000, 83(4):526-531.

Chen, "Effects of ectopic overexpression of $p21^{WAF1/CIP1}$ on aneuploidy and the malignant phenotype of human brain tumor cells," Oncogene, 1996, 13:1395-403.

Ciardiello and Tortora, "Drug therapy: EGFR antagonists in cancer treatment," New Engl J Med., 2008, 358:1160-1174.

Citri and Yarden, "EGF-ERBB signalling: towards the systems level," Nat Rev Mol Cell Biol., 2006, 7:505-516.

Costelli et al., "IGF-1 is downregulated in experimental cancer cachexia," Am J Physiol Regul Integr Comp Physiol., 2006, 291:R674-R683.

Cragg et al., "Gefitinib-induced killing of NSCLC cell lines expressing mutant EGFR requires BIM and can be enhanced by BH3 mimetics," Plos Medicine, 2007, 4:1681-1690.

Creese et al., "Dopamine receptor binding predicts clinical and pharmacological potencies of antischizophrenic drugs," Science, 1976, 192:481-483.

Daley et al., "Chlorimipramine: a novel anticancer agent with a mitochondrial target," Biochem Biophys Res Comm, 2005, 328:623-632.

Dankort and Muller, "Transgenic models of breast cancer metastasis," Cancer Treat. Res., 1996, 83:71-88.

Delia et al., "Dissociation between cell cycle arrest and apoptosis can occur in Li-Fraumeni cells heterozygous for p53 gene mutations," Oncogene, 1997, 14:2137-47.

DiFeo et al., "Roles of KLF6 and KLF6-SV1 in ovarian cancer progression and intraperitoneal dissemination," Clin Cancer Res., 2006, 12:3730-3739.

Donehower, "The p53-deficient mouse: a model for basic and applied cancer studies," Semin. Cancer Biol., 1996, 7:269-278.

Drexler, "Leukemia cell lines: in vitro models for the study of chronic myeloid leukemia," Leuk. Res., 1994, 18:919-927.

Endoh et al., "PTEN and PIK3CA expression is associated with prolonged survival after gefitinib treatment in EGFR-mutated lung cancer patients," J Thoracic Oncol., 2006, 1:629-634.

Fong et al., "Muir-Tone-like syndrome in Fhit-deficient mice," Proc. Nat. Acad. Sci., 2000, 97:4742-4747.

Frey, "Study of immune response to tumors in the rat," Methods, 1997, 12:173-188.

Ganapathi and Grabowski, "Enhancement of Sensitivity to Adriamycin in Resistant P388 Leukemia by the Calmodulin Inhibitor Trifluoperazine," Cancer Res., Aug. 1983, 43:3696-3699.

Gierthy et al., "Assessment of PCB estrogenicity in a human breast cancer cell line," Chemosphere, 1997, 34:1495-1505.

Glover, "N-myristoylation of p60src. Identification of a myristoyl-CoA:glycylpeptide N-myristoyltransferase in rat tissues," Biochem. J., 1988, 250:485-91.

Goldstein et al., "Biological efficacy of a chimeric antibody to the epidermal growth factor receptor in a human tumor xenograft model," Clin. Cancer Res., 1995, 1:1311-1318.

Gridelli et al., "Erlotinib in non-small cell lung cancer treatment: current status and future development," Oncologist, 2007, 12(7):840-9.

Gutman and Fidler, "Biology of human colon cancer metastasis," World J. Surg., 1995, 19:226-234.

Hait et al., "Phase I trial of combined therapy with bleomycin and the calmodulin antagonist, trifluoperazine," Cancer Chemother Pharmacol., 1989, 23:358-362.

Hambly et al., "Establishment and characterisation of new cell lines from human breast tumours initially established as tumour xenografts in NMRI nude mice," Breast Cancer Res. Treat., 1997, 43:247-258.

Harper et al., "The p21 Cdk-interacting protein Cip1 is a potent inhibitor of G1 cyclin-dependent kinases," Cell, 1993, 75:805-816.

Hordijk et al., "Inhibition of invasion of epithelial cells by Tiam1-Rac signaling," Science, 1997, 278:1464-66.

Hoshino et al., "S-phase fraction of human brain tumors in situ measured by uptake of bromodeoxyuridine," Int. J. Cancer, 1986, 38:369-74.

Huang et al., "Epidermal growth factor receptor blockade with C225 modulates proliferation, apoptosis, and radiosensitivity in squamous cell carcinomas of the head and neck," Cancer Res., 1999, 15:59(8):1935-40.

Ito et al., "Kruppel-like factor 6 is frequently down-regulated and induces apoptosis in non-small cell lung cancer cells," Cancer Res., 2004, 64:3838-3843.

(56) References Cited

OTHER PUBLICATIONS

Jarrett et al., "Model of human transitional cell carcinoma: tumor xenografts in upper urinary tract of nude rat," J. Endourol., 1995, 9:1-7.

Jemal et al., "Cancer statistics, 2006," CA Cancer J Clin., 2006, 56:106-130.

Jeoung et al., "Effects of tumor necrosis factor-alpha on antimitogenicity and cell cycle-related proteins in MCF-7 cells," J. Biol. Chem., 1995, 270:18367-73.

Johnson et al., "Approval summary for erlotinib for treatment of patients with locally advanced or metastatic non-small cell lung cancer after failure of at least one prior chemotherapy regimen," Clin Cancer Res., 2005, 11:6414-6421.

Kau et al., "A chemical genetic screen identifies inhibitors of regulated nuclear export of a Forkhead transcription factor in PTEN-deficient tumor cells," Cancer Cell, Dec. 2003, 4:463-476.

Kettunen et al., "Differentially expressed genes in nonsmall cell lung cancer: expression profiling of cancer-related genes in squamous cell lung cancer," Cancer Genet Cytogenet., 2004, 149:98-106.

Kobayashi et al., "EGFR mutation and resistance of non-small-cell lung cancer to gefitinib," N Engl J Med., 2005, 352:786-792.

Kuroda et al., "Prevention of cancer cachexia by a novel nuclear factor {kappa}B inhibitor in prostate cancer," Clin Cancer Res., 2005, 11:5590-5594.

Lam et al., "FOXO transcription factors: key regulators of cell fate," Biochem Soc Trans., 2006, 34:722-726.

Lazarus et al., "A new model of cancer cachexia: contribution of the ubiquitin-proteasome pathway," Am J Physiol Endocrinol Metab., 1999, 277:E332-E341.

Lee et al., "The novel combination of chlorpromazine and pentamidine exerts synergistic antiproliferative effects through dual mitotic action," Cancer Res., Dec. 1, 2007, 67(23):11359-67.

Levkovitz et al., "Differential induction of apoptosis by antidepressants in glioma and neuroblastoma cell lines: evidence for p-c-Jun, cytochrome c, and caspase-3 involvement," J Mol Neurosci., 2005, 27:29-42.

Li et al., "Subcellular distribution of p21 and PCNA in normal and repair-deficient cells following DNA damage," Curr. Biol., 1996, 6:189-199.

Liu et al., "Comparison of the drug-drug interactions potential of erlotinib and gefitinib via inhibition of UDP-glucuronosyltransferases," Drug Metab Dispos., Jan. 2010, 38(1):32-9.

Lovejoy et al., "Animal models and the molecular pathology of cancer," J. Pathol., 1997, 181:130-135.

Luria et al., Chapter 16 "Tumor Viruses," General Virology, 3d Ed., John Wiley & Sons, New York, 1978, pp. 436-446.

Ma et al., "Desipramine induces apoptosis in rat glioma cells via endoplasmic reticulum stress-dependent CHOP pathway," J Neurooncol, 2011, 101:41-48.

Mabry et al., "Transitions between lung cancer phenotypes—implications for tumor progression," Cancer Cells, 1991, 3:53-58.

Maekawa et al., "The Role of FOXO1 (FKHR) in Apoptosis of Non-Small Cell Lung Cancer (NSCLC)," Chest 2006—Poster Presentations Oct. 25, 2006, [Retrieved from the Internet Jul. 13, 2011, URL: http://meeting.chestpubs.org/cgi/content/abstract/130/4/234S-a, p. 243S, col. 1, para 5-11, abstract, 2 pages.

Mendelsohn, Chapter 317, "Principals of Neoplasia," Table 317-1 in Harrison's Principals of 1nternal Medicine, 13th Edition, Isselbacher et al., eds., McGraw-Hill, N.Y., 1994, p. 1814-1826.

Mimeault et al., "Synergistic antiproliferative and apoptotic effects induced by mixed epidermal growth factor receptor inhibitor ZD1839 and nitric oxide donor in human prostatic cancer cell lines," Prostate, Jan. 2004, 62(2):187-199.

Mitsudomi et al., "Mutations of ras genes distinguish a subset of non-small-cell lung cancer cell lines from small-cell lung cancer cell lines," Oncogene, 1991, 6:1353-1362.

Modjtahedi et al., "The human EGF receptor as a target for cancer therapy: six new rat mAbs against the receptor on the breast carcinoma MDA-MB 468," Br. J. Cancer, 1993, 67:247-253.

Moyer et al., "Induction of apoptosis and cell cycle arrest by CP-358,774, an inhibitor of epidermal growth factor receptor tyrosine kinase," Cancer Res., 1997, 57:4838-4848.

Murphy et al., "Enhancement of cisplatin efficacy by thalidomide in a 9L rat gliosarcoma model," J Neurooncol., 2007, 85:181-189.

Murren et al., "Trifluoperazine as a modulator of multidrug resistance in refractory breast cancer," Cancer Chemother Pharmacol., 1996, 38(1):65-70.

Narla et al., "A germline DNA polymorphism enhances alternative splicing of the KLF6 tumor suppressor gene and is associated with increased prostate cancer risk," Cancer Res., 2005, 65(4):1213-22.

Narla et al., "KLF6, a candidate tumor suppressor gene mutated in prostate cancer," Science, 2001, 294(5551):2563-6.

Narla et al., "KLF6-SV1 overexpression accelerates human and mouse prostate cancer progression and metastasis," J Clin Invest., 2008, 118(8):2711-21.

Narla et al., "Targeted inhibition of the KLF6 splice variant, KLF6 SV1, suppresses prostate cancer cell growth and spread," Cancer Res., 2005, 65(13):5761-8.

Ohnishi, "Purification of motility factor (GMF) from human malignant glioma cells and its biological significance in tumor invasion," Biochem. Biophys. Res. Commun , 1993, 193:518-25.

Oyasu, "Epithelial tumours of the lower urinary tract in humans and rodents," Food Chem. Toxicol., 1995, 33:747-755.

Paez et al., "EGFR mutations in lung cancer: correlation with clinical response to gefitinib therapy,", Science, 2004, 304:1497-1500.

Pao et al., "Acquired resistance of lung adenocarcinomas to gefitinib or erlotinib is associated with a second mutation in the EGFR kinase domain," PLoS Med., 2005, 2:e73, 11 pages.

Pao et al., "KRAS mutations and primary resistance of lung adenocarcinomas to gefitinib or erlotinib," PLoS Med., 2005, 2:e17, 5 pages.

Pardue, "Looking at polytene chromosomes," Methods Cell Biol., 1994, 44:333-351.

Park and Gazdar, "Biology of colorectal and gastric cancer cell lines," J. Cell Biochem., 1996, Suppl. 24:131-141.

Pilkington et al., "The role of tricyclic drugs in selective triggering of mitochondrially-mediated apoptosis in neoplastic glia: a therapeutic option in malignant glioma?" Radiol Oncol, 2006, 40:73-85.

Podsypanina et al., "Mutation of Pten/Mmac1 in mice causes neoplasia in multiple organ systems," Proc Natl Acad Sci U S A, 1999, 96:1563-1568.

Polakis, "The adenomatous polyposis coli (APC) tumor suppressor," Biochim. Biophys. Acta, 1997, 1332:F127-F147.

Politi et al., "Erlotinib resistance in mouse models of epidermal growth factor receptor-induced lung adenocarcinoma," Dis Model Mech., 2010, 3:111-119.

Politi et al., "Lung adenocarcinomas induced in mice by mutant EGF receptors found in human lung cancers respond to a tyrosine kinase inhibitor or to down-regulation of the receptors," Genes Dev., 2006, 20:1496-1510.

Prasad and Church, "Characterisation of DNA binding and transcriptional regulatory function of an endogenous mutant p53 in MDA-468 human breast cancer cells," Biochem. Biophys. Res. Commun , 1997, 232:14-19.

Probert et al., "Wasting, ischemia, and lymphoid abnormalities in mice expressing T cell-targeted human tumor necrosis factor transgenes," J Immunol., Aug. 15, 1993, 151(4):1894-906.

Product Sheet, ATCC Accession No. HB-8508, 2014, retrieved from the Internet Oct. 28, 2014, 2 pages.

Ribeiro et al., "Relationship between radiation response and p53 status in human bladder cancer cells," Int. J. Radiat. Biol., 1997,72:11-20.

Rice et al., "Targeting of multiple signaling pathways by the Hsp90 inhibitor SNX-2112 in EGFR resistance models as a single agent or in combination with erlotinib," Oncol Res., Jan. 2009, 18(5-6):229-242.

(56) References Cited

OTHER PUBLICATIONS

Rojas et al., "Controlling epidermal growth factor (EGF)-stimulated Ras activation in intact cells by a cell-permeable peptide mimicking phosphorylated EGF receptor," J Biol Chem., 1996, 271:27456-27461.
Royai et al., "Preclinical models of prostate cancer," Semin. Oncol., 1996, 23:35-40.
Russo and Russo, "Experimentally induced mammary tumors in rats," Breast Cancer Res. Treat., 1996, 39:7-20.
Sangodkar et al., "Targeted reduction of KLF6-SV1 restores chemotherapy sensitivity in resistant lung adenocarcinoma," Lung Cancer 2009, 66:292-297.
Sarbassov et al., "Phosphorylation and regulation of Akt/PKB by the rictor-mTOR complex," Science, 2005, 307:1098-1101.
Shepherd et al., "Erlotinib in previously treated non-small-cell lung cancer," N Engl J Med., 2005, 353:123-132.
Sherwood et al., "Selective inhibition of heregulin-dependent tyrosine phosphorylation and cellular signaling through erbB2, erbB3, and erbB4 by PD 158780 and a new irreversible inhibitor, PD 183805," Proc. Am. Assoc. Cancer Res., 1999, 40:723, Abstract No. 4778.
Shimamura et al., "Inferring dynamic gene networks under varying conditions for transcriptomic network comparison," Bioinformatics, 2010, 26:1064-1072.
Shoemaker et al., "Studies of neoplasia in the Min mouse," Biochem. Biophys. Acta, 1997, 1332:F25-F48.
Siena et al., "Reduced incidence of infusion-related reactions in metastatic colorectal cancer during treatment with cetuximab plus irinotecan with combined corticosteroid and antihistamine premedication," Cancer, 2010, 116(7):1827-1837.
Smits et al., "Apc1638N: a mouse model for familial adenomatous polyposis-associated desmoid tumors and cutaneous cysts," Gastroenterology, 1998, 114(2):275-283.
Sos et al., "PTEN loss contributes to erlotinib resistance in EGFR-mutant lung cancer by activation of AKT and EGFR," Cancer Res., 2009, 69:3256-3261.
Swafford et al., "Frequent aberrant methylation of p16INK4a in primary rat lung tumors," Mol. Cell. Biol., 1997, 17:1366-1374.
Taketo, "Ape gene knockout mice as a model for familial adenomatous polyposis," Prog Exp Tumor Res., 1999, 35:109-119.
Teramoto et al., "Inhibitory Effect of Anti-Epidermal Growth Factor Receptor Antibody on a Human Gastric Cancer," Cancer Supp., 1996, 77:1639-1645.
Tohyama, "Human factor-dependent leukemia cell lines," Int. J. Hematol., 1997, 65:309-317.
Traxler, "Tyrosine kinase inhibitors in cancer treatment (Part II)," Exp. Opin. Ther. Patents, 1998, 8(12):1599-1625.
Turner et al., "Treatment of human prostate cancer cells with dolastatin 10, a peptide isolated from a marine shell-less mollusk," Prostate, 1998, 34:175-81.
Tuzun, "Unraveling myasthenia gravis immunopathogenesis using animal models," Drug Discovery Today: Disease Models, 2006, 3(1):15-20.
van Custem et al., "Phase III trial of bevacizumab in combination with gemcitabine and erlotinib in patients with metastatic pancreatic cancer," J Clin Oncol., May 2009, 27(13):2231-2237.
Vassilev et al., "The levels of ubiquitinated histone H2A are highly upregulated in transformed human cells: partial colocalization of uH2A clusters and PCNA/cyclin foci in a fraction of cells in S-phase," J. Cell Sci., 1995, 108:1205-15.
Vet et al., "Differential expression of ferritin heavy chain in a rat transitional cell carcinoma progression model," Biochim. Biophys Acta, 1997, 1360:39-44.
Wang et al., "Establishment of an experimental intrapulmonary tumor nodule model," Ann. Thorne. Surg., 1997, 64:216-219.
Warren, "Cytokines in the cotton top tamarin model of human ulcerative colitis," Aliment. Pharmacol. Ther., 1996, 10(Supp 12):45-47.
Webber et al., "Immortalized and Tumorigenic Adult Human Prostatic Epithelial Cell Lines: Characteristics and Applications Part 1. Cell Markers and Immortalized Nontumorigenic Cell Lines," Prostate, 1996, 29:386-394.
Webber et al., "Immortalized and Tumorigenic Adult Human Prostatic Epithelial Cell Lines: Characteristics and Applications Part 2. Tumorigenic Cell Lines," Prostate, 1997, 30:58-64.
Webber et al., "Immortalized and Tumorigenic Adult Human Prostatic Epithelial Cell Lines: Characteristics and Applications Part 3. Oncogenes, Suppressor Genes, and Applications," Prostate, 1997, 30:136-142.
Weinert and Hartwell, "Cell cycle arrest of cdc mutants and specificity of the RAD9 checkpoint," Genetics, 1993, 134:63-80.
Wiklund et al., "Cytotoxic effects of antipsychotic drugs implicate cholesterol homeostasis as a novel chemotherapeutic target," Int J Cancer, Jan. 1, 2010, 126(1):28-40.
Woodburn et al., "ZD 1839, an epidermal growth factor tyrosine kinase in inhibitors selected for clinical development," Proc. Am. Assoc. Cancer Res., 1997, 38:633, Abstract No. 4251.
Yang et al., "Eradication of established tumors by a fully human monoclonal antibody to the epidermal growth factor receptor without concomitant chemotherapy," Cancer Res., 1999, 59:1236-43.
Yano and Sone, "Novel metastasis model of human lung cancer cells representing different histological types in SCID mice depleted of NK cells," Gan To Kagaku Ryoho, 1997, 24:489-494 (English Summary on p. 494).
Yea et al., "Ras promotes growth by alternative splicing-mediated inactivation of the KLF6 tumor suppressor in hepatocellular carcinoma," Gastroenterol., 2008, 134:1521-1531.
Yu et al., "Mutation-Specific Antibodies for the Detection of EGFR Mutations in Non-Small-Cell Lung Cancer," Clin Cancer Res., 2009, 15:3023-3028.
Zabalou et al., "A three-season comparative analysis of the chromosomal distribution of P and hobo mobile elements in a natural population of *Drosophila melanogaster*," Hereditas, 1994, 120:127-40.
Zong et al., "Trifluoperazine modulates DNA damage-induced cell death in human lung cancer cells through inhibition of DNA repair, cell cycle delays, and augmentation of pro-apoptotic signaling," Proc Am Assoc Cancer Res Annu Meeting, Apr. 2010, 51:163.
Terragni et al., "Phosphatidylinositol 3-kinase signaling in proliferating cells maintains an anti-apoptotic transcriptional program mediated by inhibition of FOXO and non-canonical activation of NFkB transcription factors", Jan. 28, 2008, BMC Cell Biology, vol. 9:6.
DiFeo et al., "The role of KLF6 and its splice variants in cancer therapy", 2009, Drug Resistance Updates, vol. 12, Issues 1-2, pp. 1-7.
Sangodkar et al., "Targeting the FOX01/KLF6 axis regulates EGFR signaling and treatment response", 2012, J. Clin. Invest., vol. 122, Issue 7, pp. 2637-2651.

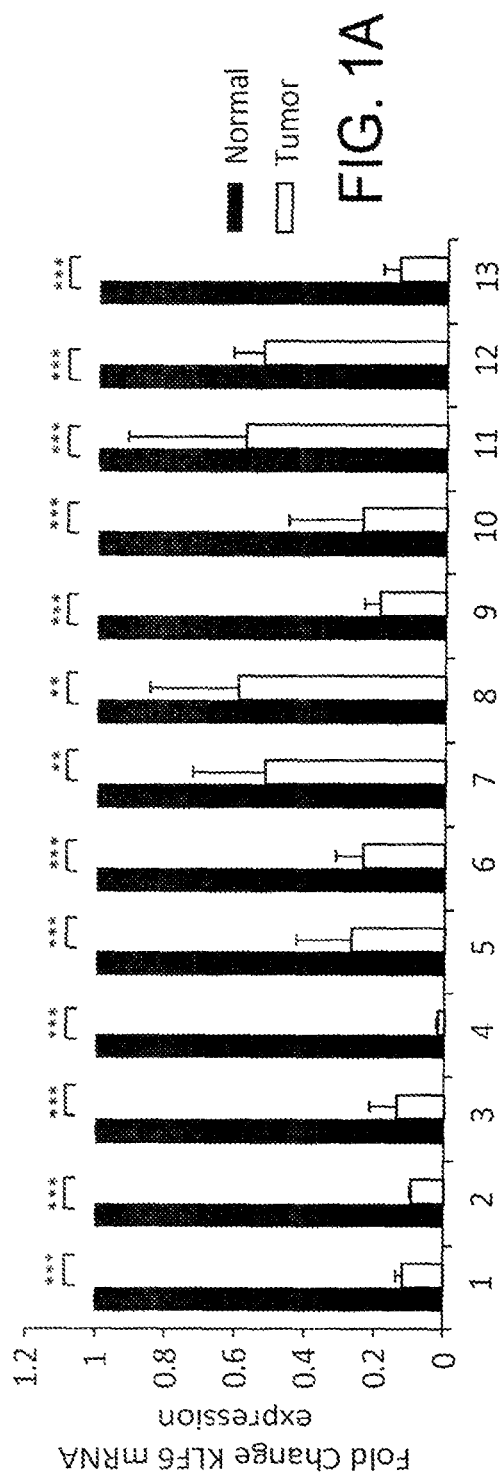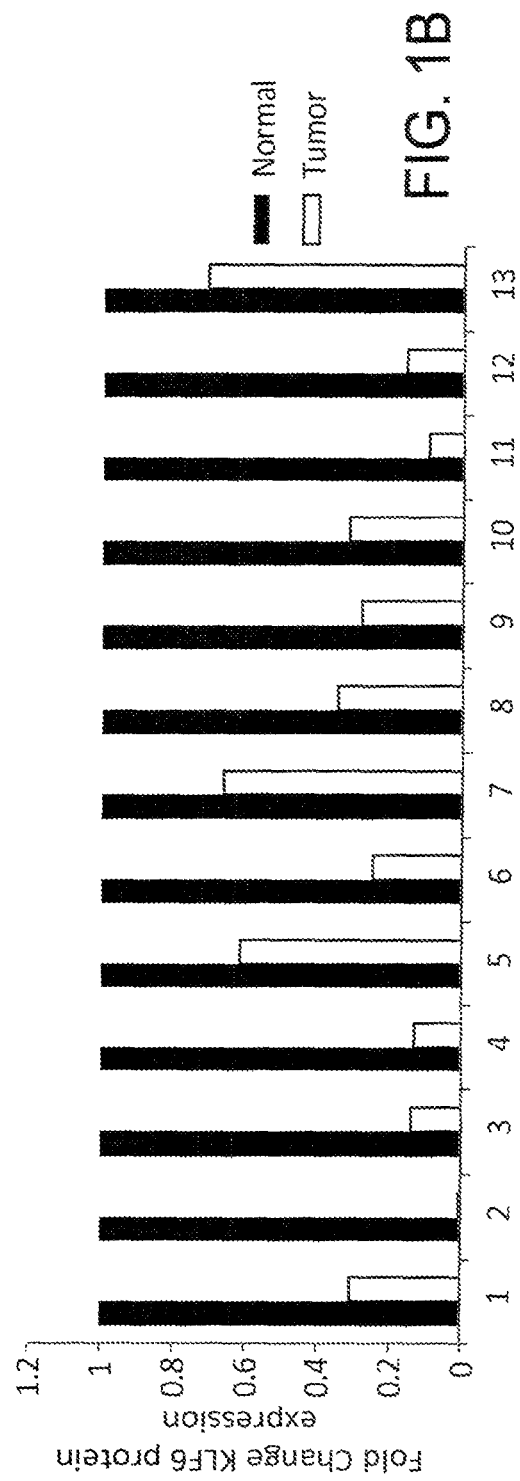

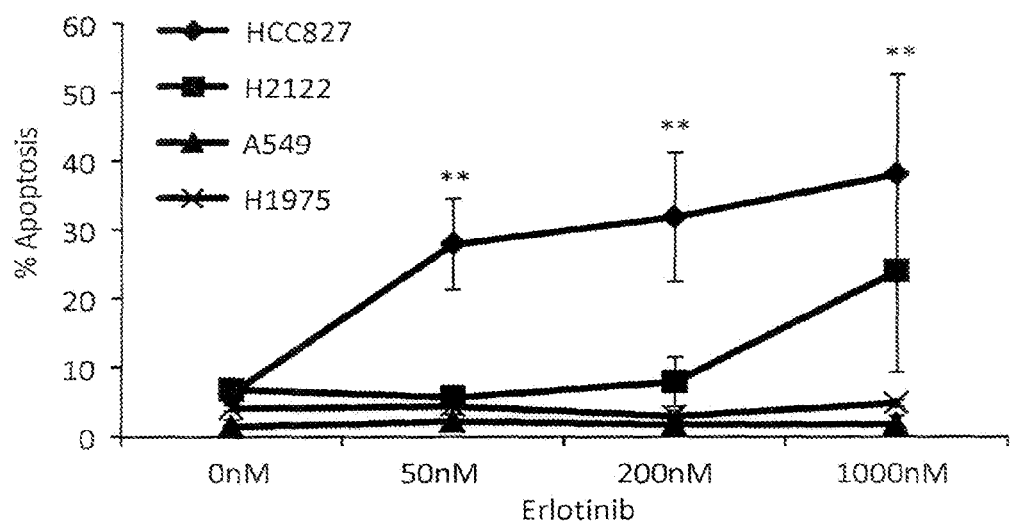
FIG. 2A
FIG. 2B
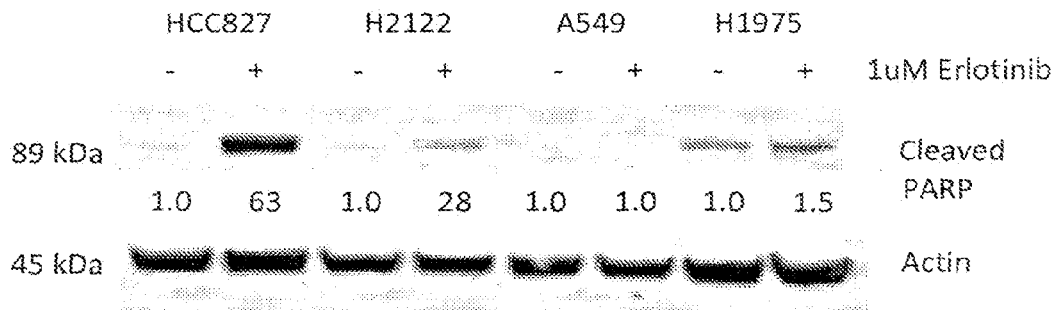
FIG. 2C

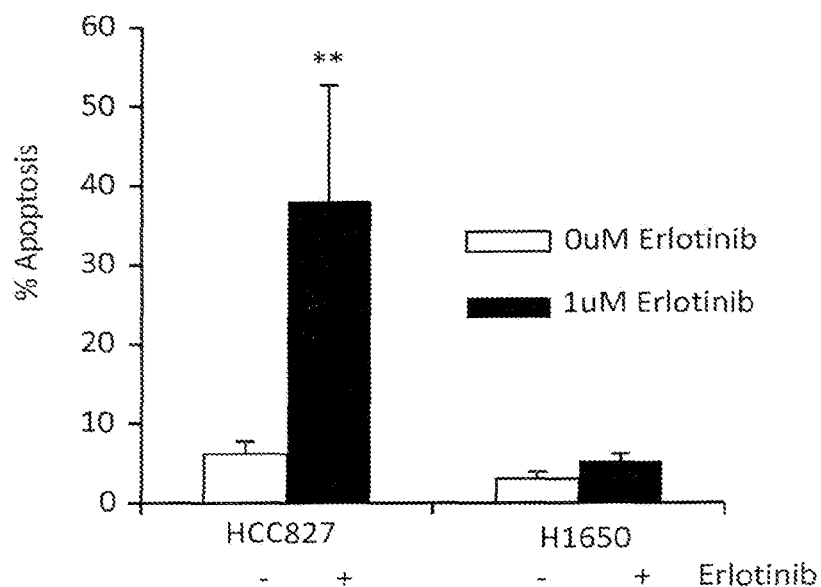
FIG. 7A
FIG. 7B
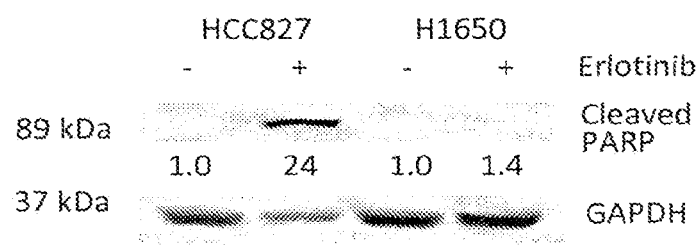
FIG. 7C

METHOD AND COMPOSITIONS FOR TREATING CANCER AND RELATED METHODS

CROSS REFERENCE TO RELATED APPLICATIONS

This application is a divisional application of U.S. patent application Ser. No. 13/348,173, filed Jan. 11, 2012 which claims the benefit of priority under 35 U.S.C. §119(e) of application No. 61/431,639, filed Jan. 11, 2011, both of which are hereby incorporated herein by reference in its entirety.

REFERENCE TO SEQUENCE LISTING

Pursuant to 37 C.F.R. 1.821(c), a sequence listing is submitted herewith as an ASCII compliant text file named "Sequence Listing.txt" that was created on Jan. 11, 2012, and has a size of 1,121 bytes. The content of the aforementioned file named "Sequence Listing.txt" is hereby incorporated by reference in its entirety.

FIELD OF THE INVENTION

The invention relates to anti-cancer therapeutics.

BACKGROUND

Members of the epidermal growth factor receptor family (ErbB1/HER1, ErbB2/HER2, ErbB3/HER3, and ErbB4/HER4) are transmembrane tyrosine kinases that are activated by ligand-induced dimerization. These receptors regulate cell proliferation, differentiation, and migration, and their abnormal activation is associated with a variety of human cancers. Several cancer drugs interact with the ATP-binding site of the EGFR kinase to halt tumor growth and increase apoptosis in cancer cells.

Compounds that directly inhibit the kinase activity of the EGFR, as well as antibodies that reduce EGFR kinase activity by blocking EGFR activation have been used as anti-cancer therapeutics. Such therapeutics are not effective for many EGFR-related illnesses or are not effective against certain patient populations. Additionally, efficacy of anti-EGFR therapeutics is limited by the invariable development of primary or acquired drug resistance.

The present inventors have discovered a new nuclear transcriptional network involving the KLF6 and FOXO1 tumor suppressor genes that regulate response to anti-EGFR-based therapies. The discovery has led to new and improved therapies for treatment of cancer.

SUMMARY

The invention relates to anti-cancer therapeutics.

In one aspect, the invention relates to treating cancers with a combination of an anti-epidermal growth factor receptor (anti-EGFR) agent and an agent that increases the activity of the Krüppel-like factor 6 (KLF6) tumor suppressor gene.

In one aspect, the invention relates to treating cancers with a combination of an anti-EGFR agent and an agent that increases the activity of the transcription factor forkhead box O1 (FOXO1) tumor suppressor gene.

In one aspect, the invention relates to treating cancers with a combination of an anti-EGFR agent and an agent that increases the activity of KLF6 or an agent that increases FOXO1.

In another aspect, the invention relates to treating cancers with a combination of an anti-EGFR agent and an agent that increases nuclear accumulation of nuclear FOXO1.

In another aspect, the invention relates to treating cancers with a combination of an anti-EGFR agent and an agent that increases nuclear accumulation of nuclear KLF6.

In another aspect, the invention relates to treating cancers with an anti-EGFR therapeutic and a tricyclic agent.

In another aspect, the invention relates to treating cancers with an anti-EGFR therapeutic and a tricyclic agent, wherein the tricyclic agent is administered at a dose that does not lead to a substantial central nervous system effect.

In another aspect, the invention relates to treating cancers with a combination of an anti-EGFR-agent and an agent that increases the activity of KLF6 in patients with primary or acquired drug resistance to anti-EGFR agents.

In another aspect, the invention relates to treating cancers with a combination of an anti-EGFR-agent and an agent that increases nuclear localization of KLF6 in patients with primary or acquired drug resistance to anti-EGFR agents.

In another aspect, the invention relates to enhancing sensitivity to anti-EGFR agents by increasing KLF6 activity.

In another aspect, the invention relates to restoring sensitivity to anti-EGFR agents by increasing KLF6 activity.

In another aspect, the invention relates to treating cancers with a combination of an anti-EGFR-agent and an agent that increases the activity of FOXO1 in patients with primary or acquired drug resistance to anti-EGFR agents.

In another aspect, the invention relates to treating cancers with a combination of an anti-EGFR-agent and an agent that increases nuclear localization of FOXO1 in patients with primary or acquired drug resistance to anti-EGFR agents.

In another aspect, the invention relates to enhancing sensitivity to anti-EGFR agents by increasing FOXO1 activity.

In another aspect, the invention relates to restoring sensitivity to anti-EGFR agents by increasing FOXO1 activity.

In another aspect, the invention relates to a method of identifying a compound that enhances cellular sensitivity to an anti-EGFR agent by contacting a cell with a test compound and determining whether the test compound increases activity of KLF6 or FOXO1 in the cell.

In another aspect, the invention relates to kits including an anti-EGFR agent and an agent that increases activity of KLF6.

In another aspect, the invention relates to kits including an anti-EGFR agent and an agent that increases activity of FOXO1.

In another aspect, the invention relates to pharmaceutical compositions including an anti-EGFR agent, an agent that enhances the therapeutic effect of the anti-EGFR agent, and a pharmaceutically acceptable excipient.

In another aspect, the invention relates to treating cancers with a combination of an anti-EGFR agent and an agent that increases the activity of the KLF6 tumor suppressor gene, provided that the agent that increases activity of KLF6 is not a phenothiazine.

In another aspect, the invention relates to treating cancers with a combination of an anti-EGFR agent and an agent that increases the activity of the FOXO1 tumor suppressor gene, provided that the agent that increases activity of FOXO1 is not a phenothiazine.

In another aspect, the invention relates to treating lung cancer, preferably non-small cell lung cancer (NSCLC) and more preferably lung adenocarcinoma, with a combination of an anti-EGFR agent, preferably erlotinib, and an agent that increases the activity of the KLF6 tumor suppressor gene, e.g., a tricyclic agent.

In another aspect, the invention relates to treating lung cancer, preferably non-small cell lung cancer (NSCLC) and more preferably lung adenocarcinoma, with a combination of an anti-EGFR agent, preferably erlotinib, and an agent that increases the activity of the KLF6 tumor suppressor gene, wherein the agent that increases activity of the KLF6 tumor suppressor gene is not a phenothiazine or a pharmaceutically acceptable salt thereof.

In another aspect, the invention relates to the use of an agent that increases activity of the KLF6 tumor suppressor gene as an adjunct anti-cancer therapy for cancer patients who have been treated with an anti-EGFR agent and developed primary or acquired drug resistance to the anti-EGFR agent.

In another aspect, the invention relates to treating cancers with a synergistic combination of an anti-EGFR agent and an agent that increases the activity of the KLF6 tumor suppressor gene.

In another aspect, the invention relates to treating lung cancer, preferably non-small cell lung cancer (NSCLC) and more preferably lung adenocarcinoma, with a combination of an anti-EGFR agent, preferably erlotinib, and an agent that increases the activity of the FOXO1 tumor suppressor gene, preferably a tricyclic agent.

In another aspect, the invention relates to treating lung cancer, preferably non-small cell lung cancer (NSCLC) and more preferably lung adenocarcinoma, with a combination of an anti-EGFR agent, preferably erlotinib, and an agent that increases the activity of the FOXO1 tumor suppressor gene, wherein the agent that increases activity of the FOXO1 tumor suppressor gene is not a phenothiazine or a pharmaceutically acceptable salt thereof.

In another aspect, the invention relates use of an agent that increases activity of the FOXO1 tumor suppressor gene as an adjunct anti-cancer therapy for cancer patients who have been treated with an anti-EGFR agent and developed primary or acquired drug resistance to the anti-EGFR agent.

In another aspect, the invention relates to treating cancers with a synergistic combination of an anti-EGFR agent and an agent that increases the activity of the FOXO1 tumor suppressor gene.

In another aspect, the invention relates to treating neoplastic disease by administering an agent that increases KLF6 activity or an agent that increases FOXO1 activity to a subject suffering from neoplastic disease.

In another aspect, the invention relates to treating neoplastic disease by administering an agent that increases KLF6 activity or an agent that increases FOXO1 activity to a subject suffering from neoplastic disease who is predicted to be only partially responsive or non-responsive to an anti-EGFR.

In another aspect, the invention relates to methods of treating NSCLC by administering an anti-EGFR agent and a tricyclic agent where the combined administered amounts of the agents together comprise a therapeutically effective amount of an active combination of agents to treat NSCLC.

In another aspect, the invention relates to methods of treating a FOXO1-disregulated condition by administering an anti-EGFR agent and a tricyclic agent where the combined administered amounts of the agents together comprise a therapeutically effective amount of an active combination of agents to treat the FOXO1-disregulated condition.

In another aspect, the invention relates to predicting whether a patient will respond to anti-EGFR therapy by determining the functional state or localization of KLF6 in cells of the patient, wherein when the cells exhibit an essentially normal functional state or a normal localization of KLF6 the patient is predicted to be a patient who will respond to anti-EGFR therapy, and when the cells exhibit a reduced functional state or mislocalization of KLF6 the patient is predicted to be a patient who will not respond to anti-EGFR therapy.

In another aspect, the invention relates to predicting whether a patient will respond to anti-EGFR therapy by determining the functional state or localization of FOXO1 in cells of the patient, wherein when the cells exhibit an essentially normal functional state or a normal localization of FOXO1 the patient is predicted to be a patient who will respond to anti-EGFR therapy, and when the cells exhibit a reduced functional state or mislocalization of FOXO1 the patient is predicted to be a patient who will not respond to anti-EGFR therapy.

The details of one or more embodiments of the invention are set forth in the accompanying drawings and the description below. Other features, objects, and advantages of the invention will be apparent from the description and drawings, and from the claims.

DESCRIPTION OF DRAWINGS

FIG. 1a-g shows results demonstrating EGFR-activation correlates with KLF6 downregulation in primary human and mouse lung adenocarcinoma. (a) Normalized quantitative real-time PCR (qRT-PCR) of KLF6 mRNA in patient-derived lung adenocarcinoma tumor samples and matched adjacent normal tissue; (b) Normalized KLP6 protein present in protein lysates from tumor and matched adjacent normal tissue; (c) KLF6 protein expression as in EGFR-activated and EGFR nonactivated tumor samples; (d) Western blot of human tumor-normal pair lysates probed with antibodies to total EGFR (T-EGFR), phosphotyrosine-EGFR (P-EGFR—Y-1068), KLF6 and GAPDH; (e) Normalized expression of human EGFR mRNA in $EGFR^{L858R}$ tetracycline-inducible mice fed normal diet (Normal) and doxycycline-supplemented diet (L858R); (f) Normalized expression of KLF6 mRNA in control mice fed normal diet (Normal) and doxycycline-supplemented diet (L858R); (g) Western blot of tumor lysates from $EGFR^{L858R}$ tetracycline-inducible mice fed normal diet (Normal) and doxycycline-supplemented diet (L858R), probed with monoclonal $EGFR^{L858R}$ Ab, polyclonal KLF6 antibody, and mouse tubulin antibody. Statistical significance determined with Students' T-test (n=3, presented as means, error bars indicate±standard deviation), P values indicated as following: *P<0.05; P<0.01; *P<0.001.

FIG. 2a-k shows results demonstrating lung adenocarcinoma cell lines upregulate KLF6 in response to anti-EGFR therapy erlotinib. (a) Mutation status of EGFR, Ras, PI3K, and PTEN status in lung adenocarcinoma cell lines; (b) Dose response curve of lung adenocarcinoma cell lines 72 h after treatment with erlotinib; (c) Cleavage of PARP on protein lysates isolated from cell lines treated with 1 µM erlotinib for 72 hours; (d) KLF6 promoter activity in the erlotinib sensitive cell line HCC827 48 hours after the addition of erlotinib; (e) Normalized change in KLF6 mRNA expression following 72 h exposure to 1 µM erlotinib treatment; (f) Western blot analysis of wtKLF6 protein in lung adenocarcinoma cell lines following 72 h exposure to 1 µM erlotinib; (g) KLF6 mRNA expression in mouse tumor samples overexpressing the lung-specific oncogenic $EGFR^{L858R}$ mutation in the presence and absence of erlotinib; (h) Western blot analysis of induction of apoptosis via increased expression of the apoptotic marker cleaved caspase-3 in erlotinib treated mice; (i) Normalized KLF6 mRNA expression in a treatment sensitive lung adenocarcinoma cell line with sequence-specific KLF6 siRNA (siKLF6) or scrambled siRNA control (siNTC); (j) Western blot analysis of KLF6 protein 72 h after transfection with KLF6 siRNA (siKLF6) or scrambled siRNA control (siNTC) and subsequent treatment with 50 nM of erlotinib and apoptosis, measured by apoptotic marker cleaved PARP; (k) Apoptotic response to erlotinib treatment after transfection KLF6 siRNA (siKLF6) or scrambled siRNA control (siNTC). All experiments were repeated three independent times; western blots representative of three independent experiments and statistical significance Student's T-test reported with standard deviation. P values indicated as following: *P<0.05; P<0.01; *P<0.001.

FIG. 7a-e shows results demonstrating constitutive activation of AKT via PTEN depletion confers resistance to erlotinib. (a) Summary of mutant EGFR, RAS, PI3K, and PTEN status in HCC827 and H1650 lung adenocarcinoma cell lines; (b) Apoptosis measured by FACS analysis by sub-G1 propidium iodide staining, (c) Western blot analysis with PARP and GAPDH antibodies, (d) Normalized KLF6 mRNA and (e) Western blot of protein lysates in HCC827 and H1650 cell lines, untreated or treated with 1 µM erlotinib for 48 h. Experiments were repeated three independent times, statistical significance determined via Students' T-test, reported as means (with ±standard deviation), P-values as follows: *P<0.05; **P<0.001.

Like reference symbols in the various drawings indicate like elements.

DETAILED DESCRIPTION

Figure 1C:
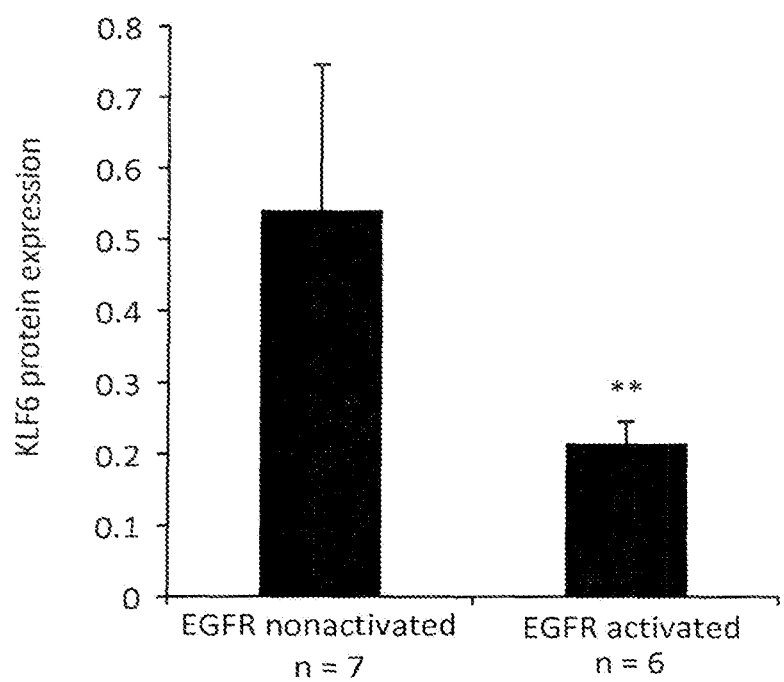
Figure 1D:
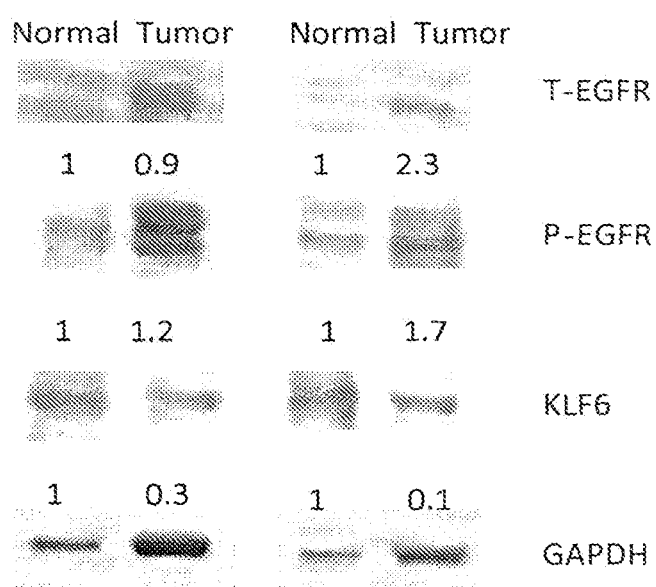

The present invention relates to cancer therapies.

The transcription factors forkhead box 01 (FOXO1) and Krüppel like factor 6 (KLF6) have roles in the regulation of diverse cellular processes including development, differentiation, proliferation and apoptosis. KLF6 is a tumor suppressor gene that is frequently inactivated by loss of heterozygosity (LOH), dysregulated alternative splicing, somatic mutation, and/or decreased expression in human cancer. KLF6 (usually referred to in these reports as COPEB) has been reported to be significantly dysregulated in lung cancer tumors compared to normal tissue and/or as a contributor to gene signatures that predict survival of lung cancer patients. KLF6 expression was also found to be significantly decreased in patient-derived lung adenocarcinoma samples compared to matched normal lung tissue. Overexpression of KLF6 has been reported to be connected with spontaneous apoptosis and decreased colony formation in lung adenocarcinoma cell lines.

FOXO1 is a transcriptional regulator of the G1/S checkpoint and of apoptosis. FOXO1 has been identified as a direct transcriptional activator of KLF6 gene expression, through binding to the KLF6 promoter. FOXO1 has also been identified as being functionally inactivated in cancer through decreased expression by AKT-mediated phosphorylation and/or cytoplasmic mislocalization in a variety of human malignancies.

The inventor has discovered a novel signalizing network in which inhibition of EGFR signaling results in decreased AKT activation and increased nuclear accumulation of FOXO1, resulting in transactivation of the KLF6 tumor suppressor gene. The inventor has surprisingly found that restoration of KLF6 activity by, for example, increasing nuclear accumulation of FOXO1 restored sensitivity to an anti-EGFR therapeutic in a resistant lung adenocarcinoma cell line. In a xenograft mouse model for lung adenocarcinoma, combined treatment with the anti-EGFR agent, erlotinib, and the phenothiazine FOXO1 nuclear export inhibitor, trifluoperazine showed synergistic effects in reducing tumor growth and increasing survival.

As set forth in greater detail in the Examples below, the inventor has identified a transcriptional network involving the KLF6 and FOXO1 tumor suppressor genes that regulates response to anti-EGFR-based therapies in both cell culture and in vivo models of the disease Inhibition of AKT signaling was found to promote FOXO1 nuclear localization, resulting in transactivation of the KLF6 tumor suppressor gene and induction of apoptosis in lung adenocarcinoma cell lines. Furthermore, the use of the FDA-approved drug Trifluoperazine Hydrochloride (TFP) that promotes FOXO1 nuclear localization, was shown to restore sensitivity to erlotinib-resistant cell lines through modulation of the KLF6/FOXO1 signaling cascade in both cell culture and a xenograft lung adenocarcinoma model. Conversely, targeted reduction of KLF6 using sequence specific siRNAs resulted in a decreased erlotinib response in both cell culture and in in vivo models of disease. Analysis by quantitative real-time PCR and western blotting confirm a significant correlation between activated oncogenic EGFR signaling and down-regulation of the FOXO1 and KLF6 tumor suppressor gene network in both primary human lung adenocarcinoma patient samples and a transgenic mouse model of the disease. These studies define a novel transcriptional network regulating oncogenic EGFR signaling and identify a class of FDA-approved drugs to restore chemosensitivity to anti-EGFR-based therapy for the treatment of metastatic lung adenocarcinoma.

Accordingly, in one aspect, the invention provides a method of treating cancers with a combination of an anti-epidermal growth factor receptor (anti-EGFR) agent and an agent that increases the activity or changes the localization of the Krüppel-like factor 6 (KLF6) and/or FOXO1 tumor suppressor genes.

As used herein, the terms "anti-epidermal growth factor receptor" and "anti-EGFR agent" also refer to any chemical entity that is currently known in the art or that will be identified in the future, and that, upon administration to a patient, results in inhibition of a biological activity associated with activation of the EGF receptor in the patient, including any of the downstream biological effects otherwise resulting from the binding to EGFR of its natural ligand. Such anti-EGFR agents include any agent that can block EGFR activation or any of the downstream biological effects of EGFR activation that are relevant to treating cancer in a patient. Such an inhibitor can act by binding directly to the intracellular domain of the receptor and inhibiting its kinase activity. Alternatively, such an inhibitor can act by occupying the ligand binding site or a portion thereof of the EGFR receptor, thereby making the receptor inaccessible to its natural ligand so that its normal biological activity is prevented or reduced. Alternatively, such an inhibitor can act by modulating the dimerization of EGFR polypeptides, or interaction of EGFR polypeptide with other proteins, or enhance ubiquitination and endocytotic degradation of EGFR. EGFR kinase inhibitors include but are not limited to low molecular weight inhibitors (small molecule based approaches), antibodies or antibody fragments, antisense constructs, small inhibitory RNAs (i.e. RNA interference by dsRNA; RNAi), and ribozymes. In a preferred embodiment, the EGFR kinase inhibitor is a small organic molecule or an antibody that binds specifically to the human EGFR.

Anti-EGFR agents can include, for example, quinazoline EGFR kinase inhibitors, pyrido-pyrimidine EGFR kinase inhibitors, pyrimido-pyrimidine EGFR kinase inhibitors, pyrrolo-pyrimidine EGFR kinase inhibitors, pyrazolo-pyrimidine EGFR kinase inhibitors, phenylamino-pyrimidine EGFR kinase inhibitors, oxindole EGFR kinase inhibitors, indolocarbazole EGFR kinase inhibitors, phthalazine EGFR kinase inhibitors, isoflavone EGFR kinase inhibitors, quinalone EGFR kinase inhibitors, and tyrphostin EGFR kinase inhibitors, such as those described in the following patent publications, and all pharmaceutically acceptable salts and solvates of said anti-EGFR agents: International Patent Publication No. WO 96/33980, WO 96/30347, WO 97/30034, WO 97/30044, WO 97/38994, WO 97/49688, WO 98/02434, WO 97/38983, WO 95/19774, WO 95/19970, WO 97/13771, WO 98/02437, WO 98/02438, WO 97/32881, WO 98/33798, WO 97/32880, WO 97/3288, WO 97/02266, WO 97/27199, WO 98/07726, WO 97/34895, WO 96/31510, WO 98/14449, WO 98/14450, WO 98/14451, WO 95/09847, WO 97/19065, WO 98/17662, WO 99/35146, WO 99/35132, WO 99/07701, and WO 92/20642; European Patent Application No. EP 520722, EP 566226, EP 787772, EP 837063, and EP 682027; U.S. Pat. Nos. 5,747,498, 5,789,427, 5,650,415, and 5,656,643; and German Patent Application No. DE 19629652. Additional non-limiting examples of low molecular weight anti-EGFR agents include any of the EGFR kinase inhibitors described in Traxler, P., 1998, Exp. Opin. Ther. Patents 8(12):1599-1625.

Specific preferred examples of low molecular weight anti-EGFR agents that can be used according to the present invention include erlotinib, (also known as [6,7-bis(2-methoxyethoxy)-4-quinazolin-4-yl]-(3-ethynylphenyl) amine; OSI-774, or Tarceva™ (erlotinib HCl); OSI Pharmaceuticals/Genentech/Roche) (U.S. Pat. No. 5,747,498; International Patent Publication No. WO 01/34574, and Moyer, J. D. et al. (1997) Cancer Res. 57:4838-4848); canertinib (also known as CI 1033; formerly known as PD183805; Pfizer) (Sherwood et al., 1999, Proc. Am. Assoc. Cancer Res. 40:723); PD-158780 (Pfizer); AG-1478 (University of California); CGP-59326 (Novartis); PKI-166 (Novartis); EKB-569 (Wyeth); GW-2016 (also known as GW-572016 or lapatinib ditosylate; GSK); and gefitinib (also known as ZD1839 or Iressa™; Astrazeneca) (Woodburn et al., 1997, Proc. Am. Assoc. Cancer Res. 38:633).

A particularly preferred low molecular weight anti-EGFR agents that can be used according to the present invention is erlotinib, i.e., [6,7-bis(2-methoxyethoxy)-4-quinazolin-4-yl]-(3-ethynylphenyl) amine, its hydrochloride salt (i.e. erlotinib HCl, Tarceva™), or other salt forms (e.g., erlotinib mesylate).

Antibody-based anti-EGFR agents include any anti-EGFR antibody or antibody fragment that can partially or completely block EGFR activation by its natural ligand. Non-limiting examples of antibody-based anti-EGFR agents include those described in Modjtahedi, H., et al., 1993, Br. J. Cancer 67:247-253; Teramoto, T., et al., 1996, Cancer 77:639-645; Goldstein et al., 1995, Clin. Cancer Res. 1:1311-1318; Huang, S. M., et al., 1999, Cancer Res. 15:59(8):1935-40; and Yang, X., et al., 1999, Cancer Res. 59:1236-1243. Thus, the anti-EGFR agent can be the monoclonal antibody Mab E7.6.3 (Yang, X. D. et al. (1999) Cancer Res. 59:1236-43), or Mab C225 (ATCC Accession No. HB-8508), or an antibody or antibody fragment having the binding specificity thereof. Suitable monoclonal antibody EGFR kinase inhibitors include, but are not limited to, IMC-C225 (also known as cetuximab or Erbitux™; Imclone Systems), ABX-EGF (Abgenix), EMI 72000 (Merck KgaA, Darmstadt), RH3 (York Medical Bioscience Inc.), MDX-447 (Medarex/Merck KgaA), and Vectibix (Amgen).

Anti-EGFR antibody can be administered, for example, with weekly doses in the range of about 0.5 mg/kg to about 10 mg/kg, preferably about 2 mg/kg to about 3 mg/kg, or about 2 mg/kg. Antibody can be administered every two weeks with doses in the range of about 1 mg/kg to about 15 mg/kg, preferably about 3 mg/kg to about 10 mg/kg, or about 6 mg/kg. Antibody can be administered every three weeks with doses in the range of about 2 mg/kg to about 30 mg/kg, preferably about 5 mg/kg to about 15 mg/kg, or about 9 mg/kg. Some antibodies can be administered with doses in the range of 50 to 500 mg/m$^2$, where dosing in mg/m$^2$, as opposed to the conventional measurement of dose in mg/kg, is a measurement based on surface area. The therapeutically effective amount of EGFR antibody in the composition can be chosen from about 1 mg, about 2 mg, about 3 mg, about 4 mg, about 5 mg, about 6 mg, about 7 mg, about 8 mg, about 9 mg, about 10 mg, about 11 mg, about 12 mg, about 13 mg, about 14 mg, or about 15 mg. In a particular exemplary dosage, monoclonal anti-EGFR antibody, e.g., Cetuximab is administered at an initial weekly dosage of 250 mg/m$^2$ followed by a dose of 400 mg/m$^2$.

As used herein, the terms "agent that increases activity of KLF6" "agent that increases activity of the KLF6 tumor suppressor" and "KLF6 activating agent" are synonymous and refer to any chemical entity that is currently known in the art or that will be identified in the future, and that, upon administration to a patient, results in increased biological activity associated with increased expression of the Krüppel-like factor 6 gene in the patient. Increased activity of KLF6 may be due to, for example and without limitation, increased transcription of the KLF6 gene, decreased alternative splicing of the KLF6 gene into its oncogenic splice variant, KLF6-SV1, increased translation of KLF6 mRNA, change in the subcellular localization of KLF6, or increased half-life of KLF6 mRNA or protein. Expression of the KLF6 may be activated by FOXO1, which exists in both the nucleus and cytoplasm. As described herein, agents that cause accumulation of FOXO1 in the nucleus lead to increased KLF6 expression. Accordingly, "KLF6 activating agents" include agents that increase nuclear accumulation of FOXO1. Nuclear accumulation of a FOXO1 may be due to, for example and without limitation, increased retention of FOXO1 in the nucleus, e.g., by binding to a stable nuclear component or inhibition of nuclear export, or an increased rate of transport of FOXO1 from the cytoplasm to the nucleus or agents that increase the half-life of FOXO1 protein or increase expression of FOXO1 mRNA expression. In addition, KLF6 or FOXO1 activating agents can be agents that changes the phosphorylation or ubiquitination state of a protein, thereby affecting it stability, localization and/or function.

In another aspect, increase of FOXO1 activity may be used in the compositions and methods described herein, independent of an increase in KLF6 activity. In certain aspects, the invention thus provides an "agent that increases activity of FOXO1", "agent that increases activity of the FOXO1 tumor suppressor" and "FOXO1 activating agent," all of which are synonymous and refer to any chemical entity that is currently known in the art or that will be identified in the future, and that, upon administration to a patient, results in increased biological activity associated with expression of the FOXO1 gene in a patient. Increased activity of FOXO1 may be due to, for example and without limitation, increased transcription of the FOXO1 gene, increased translation of FOXO1 mRNA, changes in phosphorylation of FOXO1, change in the subcellular localization of FOXO1, or increased half-life of FOXO1 mRNA or protein. Nuclear accumulation of a FOXO1 may be due to, for example and without limitation, increased retention of FOXO1 in the nucleus, e.g., by binding to a stable nuclear component or inhibition of nuclear export, or an increased rate of transport of FOXO1 from the cytoplasm to the nucleus or agents that increase the half-life of FOXO1 protein or increase expression of FOXO1 mRNA expression. In addition, FOXO1 activating agents can be agents that change the phosphorylation or ubiquitination state of a protein, thereby affecting it stability, localization and/or function.

As used herein, the term "tricyclic agent" refers collectively to tricyclic antipsychotics and tricyclic antidepressants. By way of example and without limitation, phenothiazine compounds (e.g., chlorpromazine and trifluoperazine) and thioxanthene compounds are conventionally referred to as "antipsychotics" whereas dibenzazepine compounds (e.g., chloripramine and imiprarmine) are conventionally referred to as "antidepressants". When used herein, the terms "tricyclic antidepressant" and "tricyclic antipsychotics" are used solely in accordance with custom and are meant to be coextensive in meaning and are thus not to be construed as being mutually exclusive.

In certain aspects of the invention, a KLF6 activating agent is a phenothiazine compound, e.g., trifluoperazine (IUPAC name 10-[3-(4-methylpiperazin-1-yl)propyl]-2-(trifluoromethyl)-10H-phenothiazine) or chlorpromazine (IUPAC name 3-(2-chloro-10H-phenothiazin-10-yl)-N,N-dimethyl-propan-1-amine) or a pharmaceutically acceptable salt thereof. As described herein, trifluoperazine and chlorpromazine affect FOXO1 nuclear localization leading to increased KLF6 expression.

Phenothiazine compounds are well known in the art. Examples of phenothiazine compounds include aliphatic compounds, piperidines, and, and piperazines. Phenothiazines with aliphatic side-chains include acepromazine, aceprometazine, ahistan, alimemazine, aminopromazine, chloracizine, chlorphenetazine, chlorproetazine, chlorpromazine, cyamemazine, dacemazine, diethazine, dimethothiazine, dimethoxanthate, ethacizine, ethopropazine, etymemazine, fenethazine, fluacizine, isopromethazine, levomepromazine methiomeprazine, methopromazine, methotrimeprazine, metiazinic acid, promazine, promethazine, propiomazine, propionyl-promazine, thiazinamium chloride, thiomethylpropazine, trifluomeprazine, and triflupromazine. Phenothiazines with methylpiperazine side-chains include butaperazine, perazine, prochlorperazine, thiethylperazine, thioproperazine, and trifluoperazine. Phenothiazines with piperazine-ethanol side-chains include acetophenazine, carphenazine, dixyrazine, fluphenazine, perphenazine, and thiopropazate. Phenothiazines with piperazine-ethyl side-chains include cyclophenazine, imiclozapine, methophenazine, and oxaflumazine. Phenothiazines with piperidine side-chains include duoperone, flupimazine, homophenazine, mesoridazine, metopimazine, oxyridazine, pipamazine, pipazethate, periciazine, piperacetazine, pipotiazine, perimetazine, spiclomazine, sulforidazine, and thioridazine. Miscellaneous phenothiazines include azaclorcizine, azaftozine, dichloropromazine, fenoverine, flutizenol, ftormetazine, ftorpropazine, prothipendyl, mequitazine, methdilazine, moricizine, oxomemazine, propyromazine, protizinic acid, pyrathiazine, quizaltazine, and tolonium chloride. Other examples of phenothiazine compounds are compounds 186057T and 5216177 that are disclosed in Kau et al., Cancer Cell, 2003, 4:463-476.

Exemplary dosage ranges for phentothiazine compounds are as follows. Thioridazine: 25 mg-100 mg per dose, 2-4 doses/day, 50-800 mg/day. Fluphenazine: 0.5 mg-10 mg per dose, 1-4 doses/day, 0.5-40 mg/day. Mesoridazine: 50-100 mg per dose, 3 doses/day, 150-400 mg/day. Trifluoperazine: 1-20 mg per dose, 2 doses/day, 2-40 mg/day. Chlorpromazine: 30-800 mg per dose, 1-4 doses/day, 30 mg-2 g/day. Perphenazine: 4-16 mg/dose, 2-4 doses/day, 12-64 mg/day.

Phenothiazine compounds are dopamine receptor antagonists and are clinically useful as antipsychotics, antihistaminics and antiemetics. Without being bound by theory, the inhibitory effect of trifluoperazine and chlorpromazine on FOXO1 nuclear export that leads to nuclear accumulation of FOXO1 and KLF6 activation is not believed due to activity of these compounds at dopamine receptors. See Kau et al., Cancer Cell, 2003, 4:463-476.

Anti-EGFR agents may be used in therapeutic combination with additional tricyclic agents. Examples of additional tricylic agents include, without limitation, dibenzazepines, e.g., 7-OH-Amoxapine, amezepine, amineptine, amitriptyline, amitriptylinoxide, amoxapine, aptazapine, azepindole, azipramine, butriptyline, cianopramine, ciclazindol, ciclopramine, clomipramine, cotriptyline, cyanodothiepin, demexiptiline, depramine/balipramine, desipramine, dibenzepin, dimetacrine, dosulepin/dothiepin, doxepin, enprazepine, esmirtazapine, fluotracen, hepzidine, homopipramol, imipramine, imipraminoxide, intriptyline, iprindole, ketipramine, litracen, lofepramine, losindole, loxapine, maprotiline, mariptiline, mazindol, melitracen, metapramine, mezepine, mianserin, mirtazapine, naranol, nitroxazepine, nortriptyline, noxiptiline, octriptyline, opipramol, oxaprotiline, pipofezine, pirandamine, propizepine, protriptyline, quinupramine, setiptiline/teciptiline, tandamine, tampramine, tianeptine, tienopramine and trimipramine. Preferred dibenzazepines are imipramine, desipramine, and clomipramine.

Additional examples of tricyclic agents include, without limitation, thioxanthenes, e.g., chlorprothixene, clopenthixol, flupenthixol, thiothixene, and zuclopenthixol.

When tricyclic agents are used in anti-cancer therapies, it is preferable to avoid the CNS effects such agents. Preferred tricyclic agents for anti-EGFR therapies are low potency dopamine receptor agonists. See Creese et al., Science, 1976, 192:481-483. Such agents are preferably used at a dose that exhibits anti-EGFR, i.e., anti-proliferative, effects with low, minimal, or absence of CNS effects. Low potency CNS agents may thus be used in relatively high doses, increasing their anti-proliferative effects, but without eliciting a CNS effect. Examples of low potency tricyclic agents include the phenothiazine compounds, promazine (average daily clinical dose for CNS effect, 33 Rmole/kg), chlorpromazine (average daily clinical dose for CNS effect, 12 μmole/kg), triflupromazine (average daily clinical dose for CNS effect, 6 μmole/kg) and thiordazine (average daily clinical dose for CNS effect, 13 μmole/kg). Examples of medium potency tricyclic agents include the thioxanthene compound, chlorprothixene and the phenothiazine compound, perphenazine (average daily clinical dose for CNS effect, ~1 μmole/kg). High potency tricyclic agents include the phenothiazine compounds, fluphenazine (average daily clinical dose for CNS effect, 0.17 μmole/kg), trifluoperazine (average daily clinical dose for CNS effect, 0.3 μmole/kg), and prochlorperazine (compazine) (average daily clinical dose for CNS effect, ~0.1 μmole/kg) and the thioxanthene compounds, flupentixol (average daily clinical dose for CNS effect, 0.01 μmole/kg), thiothixene (average daily clinical dose for CNS effect, 0.4 μmole/kg), and zuclopenthixol (average daily clinical dose for CNS effect, ~0.05 μmole/kg).

Certain tricyclic agents are isosteric with the phenothiazine antipsychotics and have been shown to have anti-proliferative properties. Levkovitz et al., J Mol Neurosci, 2005, 27:29-42; Daley et al., Biochem Biophys Res Comm, 2005, 328:623-632; Ma et al., J Neurooncol, 2011, 101:41-48; Pilkington et al., Radiol Oncol, 2006, 40:73-85. Chloripramine has been reported to potentiate the efficacy of imatinib in glioma therapy. Bilir et al., Intl J Oncol, 2008, 32:829-839. The anti-proliferative properties of chlorpromazine, promazine, chlorimpramine in combination with the anti-EGFR based therapy, erlotinib have been tested in vitro versus H1650 (lung), PC3 (prostate) and ASPC1, MiaPaca2 (pancreatic) cancer cell lines.

In certain embodiments of the invention, KLF6 activating agents include all KLF6 activating agents except phenothiazines.

The invention also encompasses a pharmaceutical composition that is comprised of an anti-EGFR agent, an agent that increases activity of the KLF6 tumor suppressor and a pharmaceutically acceptable carrier.

The invention also encompasses a pharmaceutical composition that is comprised of an anti-EGFR agent, an agent that increases activity of and/or changes the localization of the FOXO1 tumor suppressor and a pharmaceutically acceptable carrier.

The amount of anti-EGFR agent administered and the timing of anti-EGFR agent administration will depend on the type (species, gender, age, weight, smoker/non-smoker, etc.) and condition of the patient being treated, the severity of the disease or condition being treated, and on the route of administration. For example, small molecule EGFR kinase inhibitors can be administered to a patient in doses ranging from 0.001 to 100 mg/kg of body weight per day or per week in single or divided doses, or by continuous infusion (see for example, International Patent Publication No. WO 01/34574). In particular, erlotinib can be administered to a patient in doses ranging from 5-200 mg per day, or 100-1600 mg per week, in single or divided doses, or by continuous infusion. Another dose is 150 mg/day.

In certain aspects, the invention provides a method for the treatment of cancer in a patient in need thereof, comprising administering to a patient either simultaneously or sequentially a therapeutically effective amount of a combination comprising an anti-EGFR agent and an agent that increases activity of the KLF6 tumor suppressor gene. In certain aspects, an anti-EGFR agent and an agent that increases activity of the KLF6 tumor suppressor gene are administered in an amount that provides for a synergistic anti-tumor effect. In another aspect of the present invention, an anti-EGFR agent and an agent that increases activity of the KLF6 tumor suppressor gene are administered in an amount that is subtherapeutic with respect to the individual components. In one aspect, the EGFR Kinase inhibitor is erlotinib.

In certain aspects, the invention provides a method for the treatment of cancer in a patient in need thereof, comprising administering to a patient either simultaneously or sequentially a therapeutically effective amount of a combination comprising an anti-EGFR agent and an agent that increases activity of the FOXO1 tumor suppressor gene. In certain aspects, an anti-EGFR agent and an agent that increases activity of the FOXO1 tumor suppressor gene are administered in an amount that provides for a synergistic anti-tumor effect. In another aspect of the present invention, an anti-EGFR agent and an agent that increases activity of the FOXO1 tumor suppressor gene are administered in an amount that is subtherapeutic with respect to the individual components. In one aspect, the EGFR Kinase inhibitor is erlotinib.

In certain aspects, the compounds, compositions and methods of the invention are useful as therapeutics for treatment, prevention, amelioration, or management of various cancers or neoplastic diseases and symptoms thereof.

Compositions and methods described herein may be useful generally for the prevention, therapeutic treatment, prophylactic treatment or management of various cancers or neoplastic disorders of the central nervous system, peripheral nervous system, gastrointestinal/digestive system, genitourinary system, gynecological, head and neck, hematological/blood, musculoskeletal/soft tissue, respiratory, and breast. Examples of use include, but are not limited to, protection against and repair of injury resulting from cancers or neoplastic disorders of the brain (astrocytoma, glioblastoma, glioma), spinal cord, pituitary gland, breast (Infiltrating, Pre-invasive, inflammatory cancers, Paget's Disease, Metastatic and Recurrent Breast Cancer), blood (Hodgkin's Disease, Leukemia, Multiple Myeloma, Lymphoma), Lymph node cancer, Lung (Adenocarcinoma, Oat Cell, Non-small Cell, Small Cell, Squamous Cell, Mesothelioma), skin (melanoma, basal cell, squamous cell, Karposi's Sarcoma), Bone Cancer (Ewing's Sarcoma, Osteosarcoma, Chondrosarcoma), head and neck (laryngeal, pharyngeal (nasal cavity & sinus cavity), and esophageal cancers), oral (jaw, salivary gland, throat, thyroid, tongue, and tonsil cancers), eye, gynecological (Cervical, Endometrial, Fallopian, Ovarian, Uterine, Vaginal, and Vulvar), Genitourinary (Adrenal, bladder, kidney, penile, prostate, testicular, and urinary cancers), and gastrointestinal (appendix, bile duct (extrahepatic bile duct) colon, gallbladder, gastric, intestinal, colon, liver, pancreatic, rectal, and stomach cancers) as well as those listed below: (for a review of such disorders, see Fishman et al., 1985, Medicine, 2 d Ed., J.B. Lippincott Co., Philadelphia): Leukemia: acute leukemia, acute lymphocytic leukemia, acute myelocytic leukemia, myeloblastic, promyelocytic, myelomonocytic, monocytic erythroleukemia, chronic leukemia, chronic myelocytic (granulocytic) leukemia, chronic lymphocytic leukemia, Polycythemia vera, Gastric carcinoma, Lymphoma (malignant and non-malignant): Hodgkin's disease, non-Hodgkin's disease, Multiple myeloma, Waldenstrom's macroglobulinemia, Heavy chain disease, Solid tumors sarcomas and carcinomas: fibrosarcoma, myxosarcoma, liposarcoma, chondrosarcoma, osteogenic sarcoma, chordoma, angiosarcoma, endotheliosarcoma, lymphangiosarcoma, lymphangioendotheliosarcoma, synovioma, mesothelioma, Ewing's tumor, leiomyosarcoma, rhabdomyosarcoma, colon carcinoma, pancreatic cancer, breast cancer, ovarian cancer, prostate cancer, squamous cell carcinoma, oral squamous cell carcinoma, hepatocellular carcinoma, basal cell carcinoma, adenocarcinoma, sweat gland carcinoma, sebaceous gland carcinoma, papillary carcinoma, papillary adenocarcinomas: cystadenocarcinoma, medullary carcinoma, bronchogenic carcinoma, renal cell carcinoma, hepatoma, bile duct carcinoma, choriocarcinoma, seminoma, embryonal carcinoma, Wilms' tumor, cervical cancer, cervix adenocarcinoma, uterine cancer, testicular tumor, lung carcinoma, small cell lung carcinoma, non-small cell lung adenocarcinoma, bladder carcinoma, epithelial carcinoma, glioma, malignant glioma, glioblastoma, multiforme astrocytic gliomas, medulloblastoma, craniopharyngioma, ependymoma, pinealoma, hemangioblastoma, acoustic neuroma, oligodendroglioma, meningioma, melanoma, neuroblastoma, retinoblastoma, etc.

In specific aspects, cancer, malignancy or dysproliferative changes (such as metaplasias and dysplasias), or hyperproliferative disorders, are treatable or preventable in the ovary, breast, colon, lung, skin, pancreas, prostate, bladder, or uterus. In other specific embodiments, the cancer treatable or preventable by the administration of an effective amount of a compound or combination of compounds is sarcoma, melanoma, or leukemia. In other specific aspects, the cancer treatable or preventable by the administration of an effective amount of a compound is multiple myeloma, leukemia, a myelodysplastic syndrome or a myeloproliferative disorder. In another specific embodiment, the cancer treatable or preventable by the administration of an effective amount of a compound or compounds is a glioma.

Further, the compound may be administered according to the current method to treat, ameliorate or manage various syndromes associated with various functional benign or cancerous tumors. Amongst those syndromes that may benefit from treatment with the compounds are Beckwith-Wiedmann Syndrome, SBLA Syndrome, Li-Fraumeni Syndrome, Familial Adenomatous Polyposis syndrome (Gardner Syndrome), Hereditary Nonpolyposis Colorectal Cancer, Turcot Syndrome, Cowden Syndrome, Carney Triad Syndrome, Multiple Endocrine Neoplasia Syndromes (Wermer (MEN-1), Sipple (MEN-2a, MEN-2b), Von Hipple-Lindau Syndrome, Cushing's Syndrome, Addison's Syndrome, Verner Morrison Syndrome, Zollinger-Ellison Syndrome, WDHA Syndrome, Pancreatic Cholera, Isaac's Syndrome, Rippling muscle syndrome, Stiffman syndrome, Paraneoplastic Ataxia, Yo Syndrome, Tr Syndrome, Hu Syndrome, CV-2 Syndrome, CRMP-5 Syndromes, Opsoclonus/Myoclonus, Ma Syndromes, Morvan's fibrillary chorea, Bannayan-Riley-Runalcaba Syndrome, Peutz-Jegher Syndrome, Muir-Tone Syndrome, Hirschsprung Disease, Lynch Syndrome, Lambert-Eaton Myastenic Syndrome, Myasthenia Gravis, Neuromyotonia, Paraneoplastic Cerebellat Degeneration, Paraneoplastic Limbic Encephalitis, Sweets Syndrome, Birt-Hogg-Dube Syndrome, Naevoid Basal Cell Carcinoma Syndrome, Generalized Basaloid Follicular, Hamartoma Syndrome, Bazex Syndrome, Brooke Spiegler Syndrome, Familial Cylindromatosis, Multiple Familial Trichoepitheliomas, Androgen Deprivation Syndrome, Therapy Related Myelodysplastic Syndrome, Somnolence Syndrome, Gulf War Syndrome, and Somatostatinoma Syndrome. The compounds may be used in accordance with the method of the current invention to address the above-noted syndromes. For example, the compounds may be administered to address hereditary syndromes such as Li Fraumeni, Hereditary Nonpolyposis Colorectal Cancer, Familial Adenomatous Polyposis, and Von Hippel-Lindau Syndrome by either delaying the onset of the neoplastic aspects of the disease, reducing the number of neoplastic growths associated with the syndrome, or in general enhancing the quality of life or the longevity of those patients afflicted with these conditions. The compounds may also be administered prophylactically to address syndromes related to certain treatment, chemotherapy or radiation therapy, of the neoplastic disorder or cancer, such as androgen deprivation syndrome, therapy related myelodysplastic syndrome or somnolence syndrome, in the hopes of preventing the syndromes or reducing the severity of the syndrome.

As mentioned above, these cancers and neoplastic disorders are merely illustrative of the range of disorders that can be addressed by the compounds used in the method of the current invention. Accordingly, this invention generally provides preventative, therapeutic, or prophylactic treatment of the consequences of cancers or neoplastic disorders.

Cancer or a neoplastic disease, including, but not limited to, a neoplasm, a tumor, a metastasis, or any disease or disorder characterized by uncontrolled cell growth, can be treated or prevented by administration of an effective amount of a compound of the invention. In one aspect, a composition comprising an effective amount of one or more Compounds of the Invention, or a pharmaceutically acceptable salt thereof, is administered.

In certain aspects, the invention encompasses methods for treating or preventing cancer or a neoplastic disease comprising administering to a patient need thereof an effective amount of a compound and another therapeutic agent. In one embodiment, the therapeutic agent is a chemotherapeutic agent including, but not limited to, methotrexate, taxol, mercaptopurine, thioguanine, hydroxyurea, cytarabine, cyclophosphamide, ifosfamide, nitrosoureas, cisplatin, carboplatin, mitomycin, dacarbazine, procarbizine, etoposides, campathecins, bleomycin, doxorubicin, idarubicin, daunorubicin, dactinomycin, plicamycin, mitoxantrone, asparaginase, vinblastine, vincristine, vinorelbine, paclitaxel, and docetaxel. In one embodiment, the compound exerts its activity at the same time the other therapeutic agent exerts its activity. Other therapeutic agents are: Radiation: .gamma.-radiation, Alkylating agents Nitrogen mustards: cyclophosphamide, Ifosfamide trofosfamide, Chlorambucil, Nitrosoureas: carmustine (BCNU), Lomustine (CCNU), Alkylsulphonates busulfan, Treosulfan, Triazenes: Dacarbazine, Platinum containing compounds: Cisplatin carboplatin, Plant Alkaloids, Vinca alkaloids: vincristine, Vinblastine, Vindesine, Vinorelbine, Taxoids: paclitaxel, Docetaxol, DNA Topoisomerase Inhibitors Epipodophyllins: etoposide, Teniposide, Topotecan, 9-aminocamptothecin irinotecan (Campto®), crisnatol, Mytomycins: Mytomycin C, Mytomycin C Anti-metabolites, Anti-folates: DHFR inhibitors: methotrexate, Trimetrexate, IMP dehydrogenase Inhibitors: mycophenolic acid, Tiazofurin, Ribavirin EICAR, Ribonucleotide reductase Inhibitors: hydroxyurea deferoxamine, Pyrimidine analogs: Uracil analogs, 5-Fluorouracil, Floxuridine, Doxifluridine, Ratitrexed, Cytosine analogs cytarabine (ara C) Cytosine arabinoside fludarabine, Purine analogs: mercaptopurine, Thioguanine, Hormonal therapies Receptor antagonists: Anti-estrogens, Tamoxifen, Raloxifene megestrol, LHRH agonists: goscrclin, Leuprolide, acetate Anti-androgens: flutamide, bicalutamide, Retinoids/Deltoids Vitamin D3 analogs: EB 1089, CB 1093, KH 1060, Photodyamic therapies: vertoporfin (BPD-MA), Phthalocyanine photosensitizer, Pc4 Demethoxy-hypocrellin A (2BA-2-DMHA) Cytokines: Interferon-α Interferon-γ, Tumor necrosis factor Others: Isoprenylation inhibitors: Lovastatin Dopaminergic neurotoxins: 1-methyl-4-phenylpyridinium ion Cell cycle inhibitors: staurosporine, Actinomycins: Actinomycin D, Dactinomycin, Bleomycins: bleomycin A2, Bleomycin B2, Peplomycin, Anthracyclines: daunorubicin, Doxorubicin (adriamycin), Idarubicin, Epirubicin, Pirarubicin, Zorubicin, Mitoxantrone, MDR inhibitors: verapamil, $Ca^{2+}$ ATPase inhibitors: thapsigargin, TNF-a inhibitors/thalidomide angiogenesis inhibitors 3-(3,4-dimethoxy-phenyl)-3-(1-oxo-1,3-dihydro-isoindol-2-yl)-propionamide (Se1CIDs™), ImiDs™, Revimid.™, Actimid™.

In other embodiments, the present methods for treating or preventing cancer further comprise administering radiation therapy. The cancer can be refractory or non-refractory. The compound can be administered to a patient that has undergone surgery as treatment for the cancer.

In a specific embodiment, compound can be administered to a patient that has undergone surgery as treatment for the cancer concurrently with chemotherapy or radiation therapy. In another specific embodiment, a chemotherapeutic agent or radiation therapy is administered prior or subsequent to administration of a compound, preferably at least an hour, five hours, 12 hours, a day, a week, a month, more preferably several months (e.g., up to three months).

The chemotherapeutic agent or radiation therapy administered concurrently with, or prior or subsequent to, the administration of a compound can be accomplished by any method known in the art. The chemotherapeutic agents are preferably administered in a series of sessions, any one or a combination of the chemotherapeutic agents listed above can be administered. With respect to radiation therapy, any radiation therapy protocol can be used depending upon the type of cancer to be treated. For example, but not by way of limitation, x-ray radiation can be administered; in particular, high-energy megavoltage (radiation of greater than 1 MeV energy) can be used for deep tumors, and electron beam and orthovoltage x-ray radiation can be used for skin cancers. Gamma-ray emitting radioisotopes, such as radioactive isotopes of radium, cobalt and other elements, may also be administered to expose tissues to radiation.

Additionally, the invention provides methods of treatment of cancer or neoplastic disease with a compound as an alternative to chemotherapy or radiation therapy where the chemotherapy or the radiation therapy has proven or may prove too toxic, e.g., results in unacceptable or unbearable side effects, for the patient being treated. Alternatively, the invention provides methods of treatment wherein the compound is administered prior to, simultaneously with or following treatment with chemotherapy or radiation in an effort to prevent or ameliorate the toxic side effects of the treatment method. The patient being treated can, optionally, be treated with other cancer treatments such as surgery, radiation therapy or chemotherapy, depending on which treatment is found to be acceptable or bearable.

In preferred aspects, the compounds, compositions and methods of the invention are useful as therapeutics for treatment of cancers and neoplastic diseases that are caused, in whole or in part, by mutations in EGFR. In other preferred aspects, the compounds, compositions and methods of the invention are useful as therapeutics for treatment of cancers and neoplastic diseases that are treatable, in whole or in part, with anti-EGFR agents.

Cancers and neoplastic diseases that may be treated with the compounds, compositions and methods of the invention include, for example and without limitation, prostatic, pulmonary, pancreatic, gastric, hepatocellular, lung, breast, glioblastoma, head and neck, ovarian, renal cell, leukemia, lymphomas, sarcomas, mesotheliomas and endometrial cancers.

In a preferred embodiment, the compounds, compositions and methods of the invention are used to treat lung cancer, more preferably non small cell lung cancer (NSCLC) and, most preferably, lung adenocarcinoma.

The American Cancer Society estimates 172,700 deaths from lung cancer in the United States for 2009, exceeding cancer mortality from colorectal, breast, prostate, and pancreatic cancer combined. Lung adenocarcinoma is the most common histology (~50%) among non-small cell lung cancers (NSCLC), which as a group constitute the majority of all lung malignancies (~80%). The use of traditional cytotoxic chemotherapy to treat lung cancer is supported by evidence from dozens of randomized controlled trials. Data from clinical trials suggests, however, that >50% of patients derive no benefit from chemotherapy and thus can be considered to have chemotherapy-resistant lung cancer.

Dysregulated EGFR signaling has been implicated in playing a central role in the pathogenesis of a significant percentage of lung adenocarcinomas. Thus, much effort has been focused on the development of anti-EGFR-based therapies for the treatment of metastatic lung adenocarcinoma. Evidence from clinical trials has demonstrated that anti-EGFR-based strategies are clinically efficacious in the treatment of chemoresistant lung adenocarcinoma. Subset analysis suggests that tumors with activating EGFR mutations respond best to this class of targeted molecular therapies. Targeted molecular therapies directed against EGFR have become a mainstay for the treatment of chemoresistant metastatic lung adenocarcinoma that exhibit increased EGFR expression, receptor amplification, and activating mutations. The clinical utility of anti-EGFR-based strategies is limited, however, by the invariable development of primary or acquired drug resistance.

Primary and acquired resistance to anti-EGFR-based therapies can develop through several distinct molecular mechanisms. Commonly, constitutive activation of downstream mediators of a specific oncogenic signaling pathway will result in the development of treatment resistance. Examples of molecular events that can lead to resistance to anti-EGFR-based therapies include a gatekeeper mutation of the T790 residue (T790M) in the EFGR, activating mutations downstream of EGFR (K-Ras or PI3K), MET amplification or activation of the PI3K/AKT signaling axis through several mechanisms, for example, due to loss of the PTEN tumor suppressor gene and activating PI3K mutations.

Without being bound by theory, the PI3K-AKT signaling axis is believed to play a role in the transformed phenotype in lung adenocarcinoma. The downstream transcriptional networks regulated by PI3K-AKT signaling, however, are not completely understood.

In one aspect, an anti-EGFR agent, including erlotinib, may be administered in either a therapeutic or subtherapeutic amount for the treatment of NSCLC. In one embodiment, an anti-EGFR agent, including erlotinib, is administered in a generally subtherapeutic amount of between about 1 mg/kg and about 95 mg/kg for the duration of the treatment regimen. The treatment regimen, in one embodiment, is 35 days. An anti-EGFR agent, including erlotinib, may also be administered in an amount of between about 25 mg/kg and about 75 mg/kg or about 50 mg/kg. Therapeutic amounts of an anti-EGFR agent, including erlotinib, may also be used, including amounts of about 100 mg/kg or greater.

The isolated compounds to be used within the method of the current invention may be demonstrated to inhibit tumor cell proliferation, cell transformation and tumorigenesis in vitro or in vivo using a variety of assays known in the art, or described herein. Such assays can use cells of a cancer cell line or cells from a patient. Many assays well-known in the art can be used to assess such survival and/or growth; for example, cell proliferation can be assayed by measuring ($^3$H)-thymidine incorporation, by direct cell count, by detecting changes in transcription, translation or activity of known genes such as proto-oncogenes (e.g., fos, myc) or cell cycle markers (Rb, cdc2, cyclin A, D1, D2, D3 or E). The levels of such protein and mRNA and activity can be determined by any method well known in the art. For example, protein can be quantitated by known immunodiagnostic methods such as Western blotting or immunoprecipitation using commercially available antibodies (for example, many cell cycle marker antibodies are from Santa Cruz, Inc.). mRNA can be quantitated by methods that are well known and routine in the art, for example by northern analysis, RNase protection, the polymerase chain reaction in connection with the reverse transcription, etc. Cell viability can be assessed by using trypan-blue staining or other cell death or viability markers known in the art. Differentiation can be assessed visually based on changes in morphology and by changes in relevant marker gene expression, etc.

The present invention provides for cell cycle and cell proliferation analysis by a variety of techniques known in the art, including but not limited to the following:

As one example, bromodeoxyuridine ("BRDU") incorporation may be used as an assay to identify proliferating cells. The BRDU assay identifies a cell population undergoing DNA synthesis by incorporation of BRDU into newly synthesized DNA. Newly synthesized DNA may then be detected using an anti-BRDU antibody (see Hoshino et al., 1986, Int. J. Cancer 38, 369; Campana et al., 1988, J. Immunol. Meth. 107, 79).

Cell proliferation may also be examined using (3H)-thymidine incorporation (see e.g., Chen, J., 1996, Oncogene 13:1395 403; Jeoung, J., 1995, J. Biol. Chem. 270:18367 73). This assay allows for quantitative characterization of S-phase DNA synthesis. In this assay, cells synthesizing DNA will incorporate ($^3$H)-thymidine into newly synthesized DNA. Incorporation may then be measured by standard techniques in the art such as by counting of radioisotope in a Scintillation counter (e.g., Beckman LS 3800 Liquid Scintillation Counter).

Detection of proliferating cell nuclear antigen (PCNA) may also be used to measure cell proliferation. PCNA is a 36 kilodalton protein whose expression is elevated in proliferating cells, particularly in early G1 and S phases of the cell cycle and therefore may serve as a marker for proliferating cells. Positive cells are identified by immunostaining using an anti-PCNA antibody (see Li et al., 1996, Curr. Biol. 6:189 199; Vassilev et al., 1995, J. Cell Sci. 108:1205 15).

Cell proliferation may be measured by counting samples of a cell population over time (e.g., daily cell counts). Cells may be counted using a hemacytometer and light microscopy (e.g., HyLite hemacytometer, Hausser Scientific). Cell number may be plotted against time in order to obtain a growth curve for the population of interest. In a preferred embodiment, cells counted by this method are first mixed with the dye Trypan-blue (Sigma), such that living cells exclude the dye, and are counted as viable members of the population.

DNA content and/or mitotic index of the cells may be measured, for example, based on the DNA ploidy value of the cell. For example, cells in the G1 phase of the cell cycle generally contain a 2N DNA ploidy value. Cells in which DNA has been replicated but have not progressed through mitosis (e.g., cells in S-phase) will exhibit a ploidy value higher than 2N and up to 4N DNA content. Ploidy value and cell-cycle kinetics may be further measured using propidium iodide assay (see e.g., Turner, T., et al., 1998, Prostate 34:175 81). Alternatively, the DNA ploidy may be determined by quantitation of DNA Feulgen staining (which binds to DNA in a stoichiometric manner) on a computerized microdensitometry staining system (see e.g., Bacus, S., 1989, Am. J. Pathol. 135:783 92). In another embodiment, DNA content may be analyzed by preparation of a chromosomal spread (Zabalou, S., 1994, Hereditas. 120:127 40; Pardue, 1994, Meth. Cell Biol. 44:333 351).

The expression of cell-cycle proteins (e.g., CycA. CycB, CycE, CycD, cdc2, Cdk4/6, Rb, p21 or p27) provide crucial information relating to the proliferative state of a cell or population of cells. For example, identification in an anti-proliferative signaling pathway may be indicated by the induction of p21cip1. Increased levels of p21 expression in cells results in delayed entry into G1 of the cell cycle (Harper et al., 1993, Cell 75:805 816; Li et al., 1996, Curr. Biol. 6:189 199). p21 induction may be identified by immunostaining using a specific anti-p21 antibody available commercially (e.g., from Santa Cruz, Inc.). Similarly, cell-cycle proteins may be examined by Western blot analysis using commercially available antibodies. In another embodiment, cell populations are synchronized prior to detection of a cell cycle protein. Cell-cycle proteins may also be detected by FACS (fluorescence-activated cell sorter) analysis using antibodies against the protein of interest.

Detection of changes in length of the cell cycle or speed of cell cycle may also be used to measure inhibition of cell proliferation by a compound of the invention. In one embodiment the length of the cell cycle is determined by the doubling time of a population of cells (e.g., using cells contacted or not contacted with one or more Compounds of the Invention). In another embodiment, FACS analysis is used to analyze the phase of cell cycle progression, or purify G1, S, and G2/M fractions (see e.g., Delia, D. et al., 1997, Oncogene 14:2137 47).

Lapse of cell cycle checkpoint(s), and/or induction of cell cycle checkpoint(s), may be examined by the methods described herein, or by any method known in the art. Without limitation, a cell cycle checkpoint is a mechanism which ensures that a certain cellular events occur in a particular order. Checkpoint genes are defined by mutations that allow late events to occur without prior completion of an early event (Weinert, T., and Hartwell, L., 1993, Genetics, 134:63 80). Induction or inhibition of cell cycle checkpoint genes may be assayed, for example, by Western blot analysis, or by immunostaining, etc. Lapse of cell cycle checkpoints may be further assessed by the progression of a cell through the checkpoint without prior occurrence of specific events (e.g. progression into mitosis without complete replication of the genomic DNA).

In addition to the effects of expression of a particular cell cycle protein, activity and post-translational modifications of proteins involved in the cell cycle can play an integral role in the regulation and proliferative state of a cell. The invention provides for assays involved in the detection of post-translational modifications (e.g., phosphorylation) by any method known in the art. For example, antibodies that detect phosphorylated tyrosine residues are commercially available, and may be used in Western blot analysis to detect proteins with such modifications. In another example, modifications such as myristylation, may be detected on thin layer chromatography or reverse phase hplc (see e.g., Glover, C., 1988, Biochem. J. 250:485 91; Paige, L., 1988, Biochem J.; 250:485 91).

Activity of signaling and cell cycle proteins and/or protein complexes is often mediated by a kinase activity. The present invention provides for analysis of kinase activity by assays such as the histone H1 assay (see e.g., Delia, D. et al., 1997, Oncogene 14:2137 47).

The compounds used within the methods of the invention can also be demonstrated to alter cell proliferation in cultured cells in vitro using methods which are well known in the art. Specific examples of cell culture models include, but are not limited to, for lung cancer, primary rat lung tumor cells (Swafford et al., 1997, Mol. Cell. Biol., 17:1366 1374) and large-cell undifferentiated cancer cell lines (Mabry et al., 1991, Cancer Cells, 3:53 58); colorectal cell lines for colon cancer (Park and Gazdar, 1996, J. Cell Biochem. Suppl. 24:131 141); multiple established cell lines for breast cancer (Hambly et al., 1997, Breast Cancer Res. Treat. 43:247 258; Gierthy et al., 1997, Chemosphere 34:1495 1505; Prasad and Church, 1997, Biochem. Biophys. Res. Commun. 232: 14 19); a number of well-characterized cell models for prostate cancer (Webber et al., 1996, Prostate, Part 1, 29:386 394; Part 2, 30:58 64; and Part 3, 30:136 142; Boulikas, 1997, Anticancer Res. 17:1471 1505); for genitourinary cancers, continuous human bladder cancer cell lines (Ribeiro et al., 1997, Int. J. Radiat. Biol. 72:11 20); organ cultures of transitional cell carcinomas (Booth et al., 1997, Lab Invest. 76:843 857) and rat progression models (Vet et al., 1997, Biochim. Biophys Acta 1360:39 44); and established cell lines for leukemias and lymphomas (Drexler, 1994, Leuk. Res. 18:919 927, Tohyama, 1997, Int. J. Hematol. 65:309 317).

Compounds used in methods of treatment can also be demonstrated to inhibit cell transformation (or progression to malignant phenotype) in vitro. In this embodiment, cells with a transformed cell phenotype are contacted with one or more compounds, and examined for change in characteristics associated with a transformed phenotype (a set of in vitro characteristics associated with a tumorigenic ability in vivo), for example, but not limited to, colony formation in soft agar, a more rounded cell morphology, looser substratum attachment, loss of contact inhibition, loss of anchorage dependence, release of proteases such as plasminogen activator, increased sugar transport, decreased serum requirement, or expression of fetal antigens, etc. (see Luria et al., 1978, General Virology, 3d Ed., John Wiley & Sons, New York, pp. 436 446).

Loss of invasiveness or decreased adhesion may also be used to demonstrate the anti-cancer effects of the compounds used in the method of the Invention. For example, a critical aspect of the formation of a metastatic cancer is the ability of a precancerous or cancerous cell to detach from primary site of disease and establish a novel colony of growth at a secondary site. The ability of a cell to invade peripheral sites is reflective of a potential for a cancerous state. Loss of invasiveness may be measured by a variety of techniques known in the art including, for example, induction of E-cadherin-mediated cell-cell adhesion. Such E-cadherin-mediated adhesion can result in phenotypic reversion and loss of invasiveness (Hordijk et al., 1997, Science 278:1464 66).

Loss of invasiveness may further be examined by inhibition of cell migration. A variety of 2-dimensional and 3-dimensional cellular matrices are commercially available (Calbiochem-Novabiochem Corp. San Diego, Calif.). Cell migration across or into a matrix may be examined by microscopy, time-lapsed photography or videography, or by any method in the art allowing measurement of cellular migration. In a related embodiment, loss of invasiveness is examined by response to hepatocyte growth factor (HGF). HGF-induced cell scattering is correlated with invasiveness of cells such as Madin-Darby canine kidney (MDCK) cells. This assay identifies a cell population that has lost cell scattering activity in response to HGF (Hordijk et al., 1997, Science 278:1464 66).

Alternatively, loss of invasiveness may be measured by cell migration through a chemotaxis chamber (Neuroprobe/Precision Biochemicals Inc. Vancouver, BC). In such assay, a chemo-attractant agent is incubated on one side of the chamber (e.g., the bottom chamber) and cells are plated on a filter separating the opposite side (e.g., the top chamber). In order for cells to pass from the top chamber to the bottom chamber, the cells must actively migrate through small pores in the filter. Checkerboard analysis of the number of cells that have migrated may then be correlated with invasiveness (see e.g., Ohnishi, T., 1993, Biochem. Biophys. Res. Commun. 193:518 25).

Compounds used in methods of the invention can also be demonstrated to inhibit tumor formation in vivo. A vast number of animal models of hyperproliferative disorders, including tumorigenesis and metastatic spread, are known in the art (see Table 317-1, Chapter 317, "Principals of Neoplasia," in Harrison's Principals of Internal Medicine, 13th Edition, Isselbacher et al., eds., McGraw-Hill, N.Y., p. 1814, and Lovejoy et al., 1997, J. Pathol. 181:130 135). Specific examples include for lung cancer, transplantation of tumor nodules into rats (Wang et al., 1997, Ann. Thorac. Surg. 64:216 219) or establishment of lung cancer metastases in SCID mice depleted of NK cells (Yono and Sone, 1997, Gan To Kagaku Ryoho 24:489 494); for colon cancer, colon cancer transplantation of human colon cancer cells into nude mice (Gutman and Fidler, 1995, World J. Surg. 19:226 234), the cotton top tamarin model of human ulcerative colitis (Warren, 1996, Aliment. Pharmacol. Ther. 10 Supp 12:45 47) and mouse models with mutations of the adenomatous polyposis tumor suppressor (Polakis, 1997, Biochim. Biophys. Acta 1332:F127 F147); for breast cancer, transgenic models of breast cancer (Dankort and Muller, 1996, Cancer Treat. Res. 83:71 88; Amundadittir et al., 1996, Breast Cancer Res. Treat. 39:119 135) and chemical induction of tumors in rats (Russo and Russo, 1996, Breast Cancer Res. Treat. 39:7 20); for prostate cancer, chemically-induced and transgenic rodent models, and human xenograft models (Royai et al., 1996, Semin. Oncol. 23:35 40); for genitourinary cancers, induced bladder neoplasm in rats and mice (Oyasu, 1995, Food Chem. Toxicol 33:747 755) and xenografts of human transitional cell carcinomas into nude rats (Jarrett et al., 1995, J. Endourol. 9:1 7); and for hematopoietic cancers, transplanted allogeneic marrow in animals (Appelbaum, 1997, Leukemia 11 (Suppl. 4): S15 S17). Further, general animal models applicable to many types of cancer have been described, including, but not restricted to, the p53-deficient mouse model (Donehower, 1996, Semin. Cancer Biol. 7:269 278), the Min mouse (Shoemaker et al., 1997, Biochem. Biophys. Acta, 1332:F25 F48), and immune responses to tumors in rat (Frey, 1997, Methods, 12:173 188). Additionally, for example, a compounds ability to arrest or retard the growth of a tumor in vivo may be verified using a 9 L rat gliasarcoma model as disclosed in (Murphy et al. 2007, J Neurooncol. 85:181-189). In this model, 9 L gliasarcoma are implanted into rats. The 9 L gliasarcoma may be derived from a piece of tumor that is implanted or from a cell culture. Further, the 9 L gliasarcoma may be implanted subcutaneously as disclosed in Murphy et al.

For example, a compound to be used in the methods of the invention can be administered to a test animal, in one embodiment a test animal predisposed to develop a type of tumor, and the test animal subsequently examined for a decreased incidence of tumor formation in comparison with an animal not administered the compound. Alternatively, a compound can be administered to test animals having tumors (e.g., animals in which tumors have been induced by introduction of malignant, neoplastic, or transformed cells, or by administration of a carcinogen) and subsequently examining the tumors in the test animals for tumor regression in comparison to animals not administered the compound.

Further compounds used within the methods of the invention, may be tested in various in vivo assays in the art to determine their ability to prevent, treat, ameliorate, or manage the symptoms associated with cancer. For example, the compound's ability to address cachexia may be evaluated in vitro using an interleukin-6 assay disclosed in Kuroda et al., Clinical Cancer Research 2005 11:5590-5594. Additionally, in vivo assays, including, but not limited to, the Yoshida AH-130 rat ascites hepatoma assay (Carbo et al., British Journal of Cancer (2000) 83(4):526-531; Costelli et al., Am J Physiol Regul Integr Comp Physiol (2006) 291:R674-R683); T-Cell Targeted Human Tumor Necrosis Factor murine model (Probert et al., (1993) 151(4): 1894-1906); R-1 clone murine model (Lazarus et al. Am J Physiol Endocrinol Metab (1999) 277:E332-E341); and human prostate cancer (JCA-1) murine model (Kuroda et al., Clinical Cancer Research 2005 11:5590-5594) are useful in evaluating the compounds ability to prevent, treat, manage or ameliorate cachexia associated with cancer or neoplastic diseases.

Further a compound's ability to prevent, treat, ameliorate or manage the various syndromes associated with cancer can be evaluated using well known models in the art. For example, several animal models have been generated such as the ApcMin Mouse, 1638n, and ApcPirc models for Familial adenomatous polyposis (Amos-Landgraf J, Kwong L N, Dove W F, et al (2007). "A target-selected Apc-mutant rat kindred enhances the modeling of familial human colon cancer." PNAS 104 (10): 4036-4041); 1638N: A mouse model for familial adenomatous polyposis-associated desmoid tumors and cutaneous cysts. Gastroenterology, Volume 114, Issue 2, Pages 275-283 R. Smits, W. van der Houven van Oordt, A. Luz, C. Zurcher, S. Jagmohan-Changur, C. Breukel, P. Khan, R. Fodde; Hiai H, Hino O (eds): Animal Models of Cancer Predisposition Syndromes Prog Exp Tumor Res. Basel, Karger, 1999, vol 35, pp 109-119 (DOI: 10.1159/000062007); knock out and transgenic mice models as well as an animal model involving immunization with the acetylcholine receptor as models of myasthenia gravis (Erdem Tuzun Unraveling myasthenia gravis immunopathogenesis using animal models Drug Discovery Today: Disease Models Volume 3, Issue 1, Spring 2006, Pages 15-20); Fhit-deficient mice as a model of Muir-Tone syndrome (Fong et al., Muir-Tone-like syndrome in Fhit-deficient mice. Proc. Nat. Acad. Sci. 97: 4742-4747, 2000.)

In preferred aspects, compounds are tested for anti-neoplastic activity in the in vitro and in vivo models described in the Examples below.

In certain aspects, an agent that increases KLF6 and/or FOXO1 activity (including an agent that affect localization of KLF6 and/or FOXO1) is used as adjunct therapy, to treatment with an anti-EGFR agent, including erlotinib. Adjunct therapy includes, for example, treatment of a patient with a combination of an anti-EGFR agent and an agent that increases KLF6 and/or activity where the patient has failed to respond to therapy with an anti-EGFR agent either as monotherapy or in combination with one or more other therapeutic agent. In a preferred embodiment, adjunct therapy includes treatment of a patient with a combination of an anti-EGFR agent and an agent that increases KLF6 and/or activity where the patient has developed primary or acquired drug resistance to the anti-EGFR agent.

One example of adjunct therapy is the use of compounds and compositions that increase the activity of KLF6 and/or FOXO1 as therapy to treat patients who have developed resistant to an anti-EGFR therapy.

In another aspect, compounds and compositions described herein may be used in combination therapy as primary therapy for treatment of cancers and other neoplastic diseases. In preferred aspects, compounds and compositions described herein may be used in combination therapy as primary therapy in combination with an anti-EGFR agent.

In certain aspects, the invention also provides for treatment with a KLF6 and/or FOXO1 activating agent as first line therapy with an anti-EGFR agent for treating a patient who is predicted to be only partially responsive or non-responsive to anti-EGFR agents. Such partially or non-responsive patients may be identified, for example and without limitation, as having a PI3K mutation, having increased levels of phosphorylated AKT (e.g., at ser 473 and/or thr 308), having decreased activity of KLF6 and/or FOXO1, having mislocalized of KLF6 and/or FOXO1, or any other method known in the art that would predict a patient would not respond fully to an anti-EFGR agent. In a preferred aspect, the invention provides for treatment with a KLF6 and/or FOXO1 activating agent as first line therapy with an anti-EGFR agent for treating a patient who is predicted to be only partially responsive or non-responsive to erlotinib.

In another aspect, the invention provides for predicting whether a patient will respond to anti-EGFR therapy by determining the functional state or localization of KLF6 in cells of the patient. In the absence of evidence to the contrary, patients with cells that exhibit an essentially normal functional state of KLF6 and normal localization of KLF6 are predicted to respond to anti-EGFR therapy. Patients with cells that exhibit a reduced functional state of KLF6 or mislocalized of KLF6 are predicted to be resistant to or fail to respond anti-EGFR therapy.

The functional state of KLF6 may be determined by examining KLF6 expression or KLF6 activity. Localization of KLF6 may be determined by determining the level of KLF6 in cell fractions or by immunolocalization methods that are known in the art. The functional state of KLF6 may also be assessed by determining whether cells bear of mutant KLF6 allele or are deleted for one or both KLF6 alleles.

In another aspect, the invention provides for predicting whether a patient will respond to anti-EGFR therapy by determining the functional state or localization of FOXO1 in cells of the patient. In the absence of evidence to the contrary, patients with cells that exhibit an essentially normal functional state of FOXO1 and normal localization of FOXO1 are predicted to respond to anti-EGFR therapy. Patients with cells that exhibit a reduced functional state of FOXO1 or mislocalized of FOXO1 are predicted to be resistant to or fail to respond anti-EGFR therapy.

In another aspect, FOXO1 activity or localization can be used as a biomarker to predict whether patients resistant to an anti-EGFR therapy will respond to an adjunct therapy. Anti-EGFR resistant patients are treated with a potential adjunct therapy agent. Relocalization of FOXO1 to the nucleus in the cells of such patients following treatment with the potential adjunct therapy indicates that an anti-EGFR resistant patient will respond to adjunct therapy with the adjunct therapy agent. Failure of FOXO1 to relocalize to the nucleus in the cells of such patients following treatment with the potential adjunct therapy indicates that an anti-EGFR resistant patient will not respond to adjunct therapy with the adjunct therapy agent. Preferred adjunct therapy agents are, for example and without limitation, tricyclic agents.

For predicting whether a patient will respond to anti-EGFR therapy, FOXO1 functional state or localization may be determined in tumor cells, e.g., solid tumor cells, obtained from a biopsy of the patient. Solid tumor tissue may be obtained by, for example and without limitation, fine needle aspiration, core biopsy, and skin biopsy. Alternatively, FOXO1 functional state or localization may be determined in circulating tumor cells (CTCs) obtained from the patient. CTCs may be obtained from peripheral blood using by, for example and without limitation, capture by microfilter, density gradient centrifugation, CTC chips, or immunomagnetic capture.

The functional state of FOXO1 may be determined by examining FOXO1 expression or FOXO1 activity. Phosphorylation of nuclear FOXO1 is carried out by Akt results in translocation to the cytoplasm where phosphorylated FOXO1 is sequestered, inactive, as a complex with 14-3-3 proteins and subsequently targeted for proteasome mediated degradation is increasingly being recognized as a major mechanism for functional inactivation. The functional state of FOXO1 may thus be determined by determining FOXO1 phosphorylation levels, acetylation levels, or other post-translational modifications to the FOXO1 protein or FOXO1cellular localization. Localization of FOXO1 may be determined by determining the level of FOXO1 in cell fractions or by immunolocalization methods that are known in the art. The functional state of FOXO1 may also be assessed by determining whether cells bear of mutant FOXO1 allele or are deleted for one or both FOXO1 alleles.

Antibody-based anti-EGFR agent, or antisense, RNAi or ribozyme constructs, can be administered to a patient in doses ranging from 0.1 to 100 mg/kg of body weight per day or per week in single or divided doses, or by continuous infusion. In some instances, dosage levels below the lower limit of the aforesaid range may be more than adequate, while in other cases still larger doses may be employed without causing any harmful side effect, provided that such larger doses are first divided into several small doses for administration throughout the day.

For purposes of the present invention, "combination treatment with" "co-administration of" and "co-administering" an anti-EGFR agent and an agent that increases activity of the KLF6 tumor suppressor gene (both components referred to together as the "two active agents") refer to any administration of the two active agents, either separately or together, where the two active agents are administered as part of an appropriate dose regimen designed to obtain the benefit of the combination therapy. Thus, the two active agents can be administered either as part of the same pharmaceutical composition or in separate pharmaceutical compositions. An anti-EGFR agent can be administered prior to, at the same time as, or subsequent to administration of an agent that increases activity of the KLF6 tumor suppressor gene, or in some combination thereof. Where the anti-EGFR agent is administered to the patient at repeated intervals, e.g., during a standard course of treatment, an agent that increases activity of the KLF6 tumor suppressor gene can be administered prior to, at the same time as, or subsequent to, each administration of the anti-EGFR agent, or some combination thereof, or at different intervals in relation to the anti-EGFR agent treatment, or in a single dose prior to, at any time during, or subsequent to the course of treatment with the anti-EGFR agent.

The anti-EGFR agent and/or KLF6 activating agent will typically be administered to the patient in a dose regimen that provides for the most effective treatment of the cancer (from both efficacy and safety perspectives) for which the patient is being treated, as known in the art, and as disclosed, e.g. in International Patent Publication No. WO 01/34574. In conducting the treatment method of the present invention, anti-EGFR agent and/or KLF6 activating agent can be administered in any effective manner known in the art, such as by oral, topical, intravenous, intra-peritoneal, intramuscular, intra-articular, subcutaneous, intranasal, intra-ocular, vaginal, rectal, or intradermal routes, depending upon the type of cancer being treated, the type of anti-EGFR agent being used (e.g., small molecule, antibody, RNAi or antisense construct), and the medical judgment of the prescribing physician as based, e.g., on the results of published clinical studies.

The anti-EGFR agent and KLF6 activating agent can be administered either separately or together by the same or different routes, and in a wide variety of different dosage forms. For example, the anti-EGFR agent is preferably administered orally or parenterally, and KLF6 activating agent is preferably administered orally or parenterally. In one embodiment, the anti-EGFR agent is administered orally. Where the anti-EGFR agent is erlotinib HCl (Tarceva™), oral administration is preferable.

The anti-EGFR agent and KLF6 activating agent can be administered with various pharmaceutically acceptable inert carriers in the form of tablets, capsules, lozenges, troches, hard candies, powders, sprays, creams, salves, suppositories, jellies, gels, pastes, lotions, ointments, elixirs, syrups, and the like. Administration of such dosage forms can be carried out in single or multiple doses. Carriers include solid diluents or fillers, sterile aqueous media and various non-toxic organic solvents, etc. Oral pharmaceutical compositions can be suitably sweetened and/or flavored.

The anti-EGFR agent and KLF6 activating agent can be combined together with various pharmaceutically acceptable inert carriers in the form of sprays, creams, salves, suppositories, jellies, gels, pastes, lotions, ointments, and the like. Administration of such dosage forms can be carried out in single or multiple doses. Carriers include solid diluents or fillers, sterile aqueous media, and various non-toxic organic solvents, etc.

Methods of preparing pharmaceutical compositions comprising an anti-EGFR agent are known in the art, and are described, e.g., in PCT Publication No. WO 01/34574. Methods of preparing pharmaceutical compositions comprising KLF6 activating agent are also well known in the art and taught herein. In view of the teaching of the present invention, methods of preparing pharmaceutical compositions comprising anti-EGFR agent and KLF6 activating agent will be apparent from the above-cited publications and from other known references, such as Remington's Pharmaceutical Sciences, Mack Publishing Company, Easton, Pa., 18$^{th}$ edition (1990).

For oral administration of anti-EGFR agents and KLF6 activating agents, tablets containing one or both of the active agents are combined with any of various excipients such as, for example, micro-crystalline cellulose, sodium citrate, calcium carbonate, dicalcium phosphate and glycine, along with various disintegrants such as starch (and preferably corn, potato or tapioca starch), alginic acid and certain complex silicates, together with granulation binders like polyvinyl pyrrolidone, sucrose, gelatin and acacia. Additionally, lubricating agents such as magnesium stearate, sodium lauryl sulfate and talc are often very useful for tableting purposes. Solid compositions of a similar type may also be employed as fillers in gelatin capsules; preferred materials in this connection also include lactose or milk sugar as well as high molecular weight polyethylene glycols. When aqueous suspensions and/or elixirs are desired for oral administration, the EGFR kinase inhibitor may be combined with various sweetening or flavoring agents, coloring matter or dyes, and, if so desired, emulsifying and/or suspending agents as well, together with such diluents as water, ethanol, propylene glycol, glycerin and various like combinations thereof.

For parenteral administration of either or both of the active agents, solutions in either sesame or peanut oil or in aqueous propylene glycol may be employed, as well as sterile aqueous solutions comprising the active agent or a corresponding water-soluble salt thereof. Such sterile aqueous solutions are preferably suitably buffered, and are also preferably rendered isotonic, e.g., with sufficient saline or glucose. These particular aqueous solutions are especially suitable for intravenous, intramuscular, subcutaneous and intraperitoneal injection purposes. The oily solutions are suitable for intra-articular, intramuscular and subcutaneous injection purposes. The preparation of all these solutions under sterile conditions is readily accomplished by standard pharmaceutical techniques well known to those skilled in the art. Any parenteral formulation selected for administration of proteinaceous anti-EGFR agents should be selected so as to avoid denaturation and loss of biological activity.

Additionally, it is possible to topically administer either or both of the active agents, by way of, for example, creams, lotions, jellies, gels, pastes, ointments, salves and the like, in accordance with standard pharmaceutical practice. For example, a topical formulation comprising an anti-EGFR agent and/or a KLF6 activating agent in about 0.1% (w/v) to about 5% (w/v) concentration can be prepared.

For veterinary purposes, the active agents can be administered separately or together to animals using any of the forms and by any of the routes described above. In a preferred embodiment, the EGFR kinase inhibitor is administered in the form of a capsule, bolus, tablet, liquid drench, by injection or as an implant. As an alternative, the EGFR kinase inhibitor can be administered with the animal feedstuff, and for this purpose a concentrated feed additive or premix may be prepared for a normal animal feed. The PDX is preferably administered in the form of liquid drench, by injection or as an implant. Such formulations are prepared in a conventional manner in accordance with standard veterinary practice.

The present invention further provides a kit comprising a single container comprising anti-EGFR agent and KLF6 activating agent. The present invention further provides a kit comprising a first container comprising an anti-EGFR agent and a second container comprising a KLF6 activating agent. In a preferred embodiment, the kit containers may further include a pharmaceutically acceptable carrier. The kit may further include a sterile diluent, which is preferably stored in a separate additional container. The kit may further include a package insert comprising printed instructions directing the use of the combined treatment as a method for treating cancer.

Preferably the composition is comprised of a pharmaceutically acceptable carrier and a non-toxic therapeutically effective amount of an anti-EGFR agent and KLF6 activating agent (including pharmaceutically acceptable salts of each component thereof). Moreover, within this preferred embodiment, the invention encompasses a pharmaceutical composition for the treatment of disease, the use of which results in the inhibition of growth of neoplastic cells, benign or malignant tumors, or metastases, comprising a pharmaceutically acceptable carrier and a non-toxic therapeutically effective amount of an anti-EGFR agent and KLF6 activating agent (including pharmaceutically acceptable salts of each component thereof).

The term "pharmaceutically acceptable salts" refers to salts prepared from pharmaceutically acceptable non-toxic bases or acids. When a compound of the present invention is acidic, its corresponding salt can be conveniently prepared from pharmaceutically acceptable non-toxic bases, including inorganic bases and organic bases. Salts derived from such inorganic bases include aluminum, ammonium, calcium, copper (cupric and cuprous), ferric, ferrous, lithium, magnesium, manganese (manganic and manganous), potassium, sodium, zinc and the like salts. Particularly preferred are the ammonium, calcium, magnesium, potassium and sodium slats. Salts derived from pharmaceutically acceptable organic non-toxic bases include salts of primary, secondary, and tertiary amines, as well as cyclic amines and substituted amines such as naturally occurring and synthesized substituted amines. Other pharmaceutically acceptable organic non-toxic bases from which salts can be formed include ion exchange resins such as, for example, arginine, betaine, caffeine, choline, N',N'-dibenzylethylenediamine, diethylamine, 2-diethylaminoethanol, 2-dimethylaminoethanol, ethanolamine, ethylenediamine, N-ethylmorpholine, N-ethylpiperidine, glucamine, glucosamine, histidine, hydrabamine, isopropylamine, lysine, methylglucamine, morpholine, piperazine, piperidine, polyamine resins, procaine, purines, theobromine, triethylameine, trimethylamine, tripropylamine, tromethamine and the like.

When a compound of the present invention is basic, its corresponding salt can be conveniently prepared from pharmaceutically acceptable non-toxic acids, including inorganic and organic acids. Such acids include, for example, acetic, benzenesulfonic, benzoic, camphorsulfonic, citric, ethanesulfonic, fumaric, gluconic, glutamic, hydrobromic, hydrochloric, isethionic, lactic, maleic, malic, mandelic, methanesulfonic, mucic, nitric, pamoic, pantothenic, phosphoric, succinic, sulfuric, tartaric, p-toluenesulfonic acid and the like. Particularly preferred are citric, hydrobromic, hydrochloric, maleic, phosphoric, sulfuric and tartaric acids.

The pharmaceutical compositions of the present invention comprise an anti-EGFR agent and KLF6 activating agent (including pharmaceutically acceptable salts of each component thereof) as active ingredient, a pharmaceutically acceptable carrier and optionally other therapeutic ingredients or adjuvants. Other therapeutic agents may include those cytotoxic, chemotherapeutic or anti-cancer agents, or agents that enhance the effects of such agents, as listed above. The compositions include compositions suitable for oral, rectal, topical, and parenteral (including subcutaneous, intramuscular, and intravenous) administration, although the most suitable route in any given case will depend on the particular host, and nature and severity of the conditions for which the active ingredient is being administered. The pharmaceutical compositions may be conveniently presented in unit dosage form and prepared by any of the methods well known in the art of pharmacy.

In practice, the compounds represented by an anti-EGFR agent and KLF6 activating agent combination (including pharmaceutically acceptable salts of each component thereof) of this invention can be combined as the active ingredient in intimate admixture with a pharmaceutical carrier according to conventional pharmaceutical compounding techniques. The carrier may take a wide variety of forms depending on the form of preparation desired for administration, e.g. oral or parenteral (including intravenous). Thus, the pharmaceutical compositions of the present invention can be presented as discrete units suitable for oral administration such as capsules, cachets or tablets each containing a predetermined amount of the active ingredient. Further, the compositions can be presented as a powder, as granules, as a solution, as a suspension in an aqueous liquid, as a non-aqueous liquid, as an oil-in-water emulsion, or as a water-in-oil liquid emulsion. In addition to the common dosage forms set out above, an anti-EGFR agent and KLF6 activating agent combination (including pharmaceutically acceptable salts of each component thereof) may also be administered by controlled release means and/or delivery devices. The combination compositions may be prepared by any of the methods of pharmacy. In general, such methods include a step of bringing into association the active ingredients with the carrier that constitutes one or more necessary ingredients. In general, the compositions are prepared by uniformly and intimately admixing the active ingredient with liquid carriers or finely divided solid carriers or both. The product can then be conveniently shaped into the desired presentation.

In one embodiment of this invention, a pharmaceutical composition can comprise an anti-EGFR agent and KLF6 activating agent in combination with an anticancer agent, wherein said anti-cancer agent is a member selected from the group consisting of alkylating drugs, antimetabolites, microtubule inhibitors, podophyllotoxins, antibiotics, nitrosoureas, hormone therapies, kinase inhibitors, activators of tumor cell apoptosis, and antiangiogenic agents.

The pharmaceutical carrier employed can be, for example, a solid, liquid, or gas. Examples of solid carriers include lactose, terra alba, sucrose, talc, gelatin, agar, pectin, acacia, magnesium stearate, and stearic acid. Examples of liquid carriers are sugar syrup, peanut oil, olive oil, and water. Examples of gaseous carriers include carbon dioxide and nitrogen.

In preparing the compositions for oral dosage form, any convenient pharmaceutical media may be employed. For example, water, glycols, oils, alcohols, flavoring agents, preservatives, coloring agents, and the like may be used to form oral liquid preparations such as suspensions, elixirs and solutions; while carriers such as starches, sugars, microcrystalline cellulose, diluents, granulating agents, lubricants, binders, disintegrating agents, and the like may be used to form oral solid preparations such as powders, capsules and tablets. Because of their ease of administration, tablets and capsules are the preferred oral dosage units whereby solid pharmaceutical carriers are employed. Optionally, tablets may be coated by standard aqueous or nonaqueous techniques.

A tablet containing the composition of this invention may be prepared by compression or molding, optionally with one or more accessory ingredients or adjuvants. Compressed tablets may be prepared by compressing, in a suitable machine, the active ingredient in a free-flowing form such as powder or granules, optionally mixed with a binder, lubricant, inert diluent, surface active or dispersing agent. Molded tablets may be made by molding in a suitable machine, a mixture of the powdered compound moistened with an inert liquid diluent. Each tablet preferably contains from about 0.05 mg to about 5 g of the active ingredient and each cachet or capsule preferably containing from about 0.05 mg to about 5 g of the active ingredient.

Pharmaceutical compositions of the present invention suitable for parenteral administration may be prepared as solutions or suspensions of the active compounds in water. A suitable surfactant can be included such as, for example, hydroxypropylcellulose. Dispersions can also be prepared in glycerol, liquid polyethylene glycols, and mixtures thereof in oils. Further, a preservative can be included to prevent the detrimental growth of microorganisms.

Pharmaceutical compositions of the present invention suitable for injectable use include sterile aqueous solutions or dispersions. Furthermore, the compositions can be in the form of sterile powders for the extemporaneous preparation of such sterile injectable solutions or dispersions. In all cases, the final injectable form must be sterile and must be effectively fluid for easy syringability. The pharmaceutical compositions must be stable under the conditions of manufacture and storage; thus, preferably should be preserved against the contaminating action of microorganisms such as bacteria and fungi. The carrier can be a solvent or dispersion medium containing, for example, water, ethanol, polyol (e.g., glycerol, propylene glycol and liquid polyethylene glycol), vegetable oils, and suitable mixtures thereof.

Pharmaceutical compositions of the present invention can be in a form suitable for topical use such as, for example, an aerosol, cream, ointment, lotion, dusting powder, or the like.

Further, the compositions can be in a form suitable for use in transdermal devices. These formulations may be prepared, utilizing an anti-EGFR agent and KLF6 activating agent (including pharmaceutically acceptable salts of each component thereof) of this invention, via conventional processing methods. As an example, a cream or ointment is prepared by admixing hydrophilic material and water, together with about 5 wt % to about 10 wt % of the compound, to produce a cream or ointment having a desired consistency.

Pharmaceutical compositions of this invention can be in a form suitable for rectal administration wherein the carrier is a solid. It is preferable that the mixture forms unit dose suppositories. Suitable carriers include cocoa butter and other materials commonly used in the art. The suppositories may be conveniently formed by first admixing the composition with the softened or melted carrier(s) followed by chilling and shaping in molds.

In addition to the aforementioned carrier ingredients, the pharmaceutical formulations described above may include, as appropriate, one or more additional carrier ingredients such as diluents, buffers, flavoring agents, binders, surface-active agents, thickeners, lubricants, preservatives (including anti-oxidants) and the like. Furthermore, other adjuvants can be included to render the formulation isotonic with the blood of the intended recipient. Compositions containing an anti-EGFR agent and KLF6 activating agent combination (including pharmaceutically acceptable salts of each component thereof) may also be prepared in powder or liquid concentrate form.

Dosage levels for the compounds of the combination of this invention will be approximately as described herein, or as described in the art for these compounds. It is understood, however, that the specific dose level for any particular patient will depend upon a variety of factors including the age, body weight, general health, sex, diet, time of administration, route of administration, rate of excretion, drug combination and the severity of the particular disease undergoing therapy.

Additional objects, advantages, and novel features of the present invention will become apparent to one ordinarily skilled in the art upon examination of the following examples, which are not intended to be limiting. Additionally, each of the various embodiments and aspects of the present invention as delineated hereinabove and as claimed in the claims section below finds experimental support in the following examples.

EXAMPLES

Example 1

Methods

Cell Culture, Mice Tumor Samples, and Patient Sample Cohort.

HCC827, H2122, H1975, and H1650 cell lines were obtained from the American Tissue Culture Collection and were cultured according to the supplier's instructions. Cell line A549luc was obtained from Caliper Life Sciences and were cultured according to the supplier's instructions. H3255 cell line was obtained from Dr. Katerina Politi and Dr. Harold Varmus at Memorial Sloan-Kettering Cancer Center. $EGFR^{L858R}$-derivedtumor samples (Politi, K., et al. Genes Dev 20, 1496-1510 (2006)) were generously provided from Dr. Katerina Politi and Dr. Harold Varmus at Memorial Sloan-Kettering Cancer Center and were grown in RPMI medium supplemented with 10% FBS, penicillin and streptomycin. PTEN/Mmac1+/− heterozygous mice were obtained from the NCI Mouse Repository. All animal studies were approved by the Mount Sinai School of Medicine IACUC. Human tissue samples were obtained from the Mount Sinai BioBank under Institutional Review Board (IRB) approval. Tissue samples were snap frozen in liquid nitrogen at the time of surgery.

Chemicals.

Erlotinib was obtained from OSI Pharmaceuticals Inc., AKT inhibitor IV from Calbiochem, and TFP from Sigma Aldrich. All chemicals were dissolved in DMSO at either 10 mM stock solution (erlotinib and AKT inhibitor IV) or 40 mM stock solution (TFP). Further dilutions to the required concentration were made in RPMI 1640 medium (Fisher Scientific).

Antibodies.

Rabbit antibodies specific for P-EGFR (2234), EGFR (4405), L858R (3197), P-AKT (4058), AKT (9272), P-ERK (9272), ERK (4695), Cleaved Caspase 3 (9661), P-FOXO1 (2486), and FOXO1 (2880) were obtained from Cell Signaling Technologies. Rabbit polyclonal KLF6 antibody (sc-7158), goat polyclonal Actin antibody (sc-1616), and mouse monoclonal GAPDH antibody (sc-32233) were purchased from Santa Cruz Biotechnology. Rabbit polyclonal PARP (G7341) was obtained from Promega.

Quantitative Real-Time PCR.

RNA was isolated from cell lines and tumor samples using the RNeasy Mini Kit (Qiagen) as per manufacturer's instructions. For each PCR reaction, 1 µg RNA was reverse transcribed using iScript cDNA synthesis kit (BioRad Laboratories). Each cDNA sample was subjected to sequence-specific partial amplification with specific primers and the SYBR green PCR Master Mix (Applied Biosystems) on an ABI PRISM 7900HT plate-reader instrument. Expression levels of KLF6 mRNA were detected with validated KLF6-specific primer sequences as previously described by DiFeo, A., et al., Clin Cancer Res 12, 3730-3739 (2006). The following primers were also used: FOXO1 forward 5' AAGGATAAGGGTGACAGCAACAG (SEQ ID NO: 1) and reverse 5' TTGCTGTGTAGGGACAGATTATGAC (SEQ ID NO: 2, and EGFR forward 5' TCCTCTGGAG-GCTGAGAAAA (SEQ ID NO: 3) and reverse 5' GGGCTCTGGAGGAAAAGAAA (SEQ ID NO: 4). All values were normalized to glyceraldehyde-3-phosphate dehydrogenase (GAPDH) levels and compared to both 18S and actin internal controls.

Plasmids and siRNAs.

AKTmyr and FOXO1 plasmids (Addgene) were transfected into cells by Lipofectamine 2000 incubation (Invitrogen) for 20 minutes. Validated KLF6-specific siRNA was transfected using HiPerfect (Qiagen) into cell lines seeded at 60-70% confluency. For FOXO1 inhibition, transfections were performed using FOXO1A ON-TARGETplus SMARTpool from Dharmacon. Knockdown and overexpression was assessed by western blotting and quantitative real-time PCR.

KLF6 Promoter Assay.

HCC827 cells were co-transfected with 1 µg of pGL3-KLF6 promoter luciferase construct and pRL-TK plasmid (see Yea, S., et al. Gastroenterology 134, 1521-1531 (2008)) (as a control for transfection efficiency). Cells were treated with increasing doses of erlotinib 6 h after transfection. Cell lysates were prepared using the Dual-Luciferase Reporter Assay system (Promega) 24 h after treatment. Luciferase activity was analyzed in 20 µL of lysate using Modulus II Microplate Multimode Reader.

Nuclear Cytoplasmic Fractionation.

H1650 cells were seeded and grown to 60-70% confluency, and treated with increasing doses of TFP. Cell lysates were extracted using NE-PER Nuclear and Cytoplasmic Extraction Reagents (Thermo Scientific) according to supplier's protocol.

Clonogenic Assay.

HCC827 shLuc and shKLF6 were plated at a low density in 6-well plates. After 24 h, cells were treated with 50 nM of erlotinib and further incubated for 7 days. Cells were fixed and then stained with 1% crystal violet staining solution.

TUNEL Assay and Immunohistochemistry.

ApopTag Fluorescein In Situ Apoptosis Detection kit (Millipore) was used according to supplier's protocol to perform TUNEL assay. Vectashield Mounting Medium with Propidium Iodide (Vector Laboratories) was used to counterstain. Quantitation of images obtained from TUNEL was performed using NIS-Elements for Basic Sciences (NIKON) and normalized to nuclear counterstaining by propidium iodide. Paraffin-embedded tumors were stained with anti-PCNA (FL-261), which was obtained from Santa Cruz. Quantitation was completed using a cell counter function of ImageJ (http://rsb.info.nih gov/ij/).

Analysis of Apoptosis.

Cells treated with drug or transfected with siRNA were stained with propidium iodide to ascertain DNA content and determine cell cycle distribution within the cell population as previously described. Sangodkar, J., et al. Lung Cancer 66, 292-297 (2009). Sub-G1 peaks were analyzed on DNA histograms; hypo diploid DNA represented dead cells. This fraction indicated apoptotic as well as necrotic cells. Apoptosis was further validated by Caspase 3 and PARP cleavage through western blotting.

Tumorgenicity Assay.

pSUPER.retro.puro vectors (Oligoengine) encoding short hairpin RNA targeting KLF6 were designed. See Shepherd, F. A., et al. N Engl J Med 353, 123-132 (2005). A pSUPER vector encoding Luciferase shRNA was used as a control. Stable cell lines of HCC827 were generated by retroviral transfection of the pSUPER-shLuciferase (shLuc) and pSUPER-shKLF6 (shKLF6) and selected with 2 µg/mL puromycin as described by Shepherd, F. A., et al., N Engl J Med 353, 123-132 (2005). Polyclonal pools of the shRNA-infected cell lines were collected and KLF6 knockdown was determined by qRT-PCR and Western blot. Stable cell lines ($10 \times 10^7$) were injected in the right flank of the 6 to 8-week old female BALB/c nu/nu mice. Tumor volume was assessed weekly as described by Sangodkar, J., et al. (Lung Cancer 66, 292-297 (2009)) until volumes reached an average of 100 $mm^3$. The following treatments were administered via intraperitoneal injection: Vehicle (DMSO) and erlotinib (25 mg/kg). A total of 4 treatments were given with a 48 h rest period.

H1650 cells ($5 \times 10^6$) were similarly injected into the right flank of 6 to 8-week old female BALB/c nu/nu mice. Tumor volume was assessed weekly as previously described by Sangodkar, J., et al., supra until volumes reached an average of 200 $mm^3$. The following treatments were administered via intraperitoneal injection: Vehicle control (DMSO), erlotinib (25 mg/kg), TFP (10 mg/kg), and combination erlotinib (25 mg/kg) and TFP (10 mg/kg). A total of four treatments were given with a 48 h rest period. All animal studies were approved by the Mount Sinai School of Medicine IACUC.

Statistical Analyses.

Kaplan-Meier survival curve and patient cohort analysis was performed using GraphPad Prism. Statistical significance determined with Students' T-test (presented as means, error bars indicate±standard deviation), P values indicated as following: *P<0.05; P<0.01; *P<0.001.

Example 2

Activated EGFR Signaling Drives Transcriptional Downregulation of KLF6 Expression in Primary Human Lung Adenocarcinomas and a Murine Model of the Disease Downregulation of KLF6 expression in primary lung cancer was studied in a cohort of microdissected normal and tumor patient-derived lung adenocarcinoma samples. Quantitative real-time PCR was performed using validated real-time PCR primers specific to wild-type KLF6 (wtKLF6) (DiFeo, A., et al. Clin Cancer Res 12, 3730-3739 (2006)) and western blotting with a KLF6 polyclonal antibody was used to quantitate KLF6 expression in thirteen matched tumor-normal tissue pairs. Patient-derived lung adenocarcinoma tumor samples with matched normal tissue adjacent to the retrieved tumor were evaluated for KLF6 mRNA expression using quantitative real-time PCR (qRT-PCR) using validated wild-type KLF6-specific primers and normalized to three independent housekeeping genes (GAPDH, Actin, and 18S transcripts). KLF6 mRNA and protein expression was decreased in all patient tumor samples analyzed, by an average of more than 50% as compared to surrounding normal lung tissue (FIG. 1a, b).

To examine the relationship between activated EGFR signaling and KLF6 expression, the respective expression of phosphorylated EGFR (Y-1068) (Rojas, M., et al. J Biol Chem 271, 27456-27461 (1996)) and KLF6 were correlated at the protein levels. Homogenized protein lysates from tumor and normal samples were subjected to Western blotting and probed with a polyclonal KLF6 antibody; quantitation was performed via densitometry normalized against GAPDH expression, then analyzed for fold change as compared to the matched normal tissue of each sample pair. Tumor samples were deemed 'activated' if pEGFR (Y1068) expression was higher compared to matched surrounding lung tissue from the same patient. Activated EGFR signaling, as assessed by comparing tyrosine phosphorylation between matched normal and tumor tissue, was associated with significantly lower KLF6 expression in patient lung adenocarcinomas when compared to tumors demonstrating low levels of EGFR activation (FIG. 1c, d).

Figure 1E:
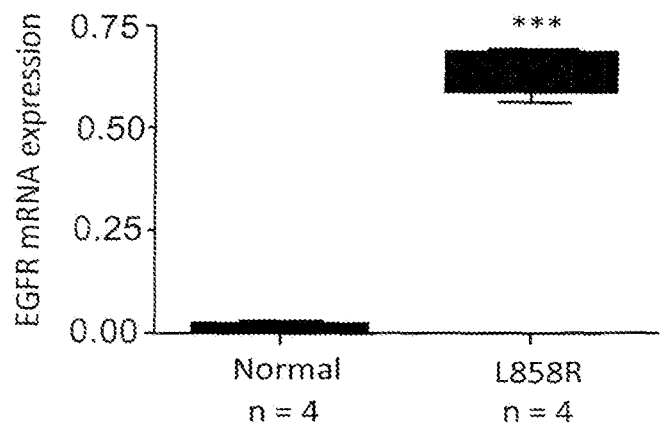

The correlation between EGFR activation and downregulation of KLF6 was investigated further utilizing a mouse model of lung adenocarcinoma driven by the activated EGFR$^{L858R}$ allele, a commonly mutated residue in human lung cancer that is associated with constitutive downstream signaling and response to anti-EGFR-based therapies such as erlotinib and gefitinib. Politi, K., et al. Genes Dev 20, 1496-1510 (2006). By employing a tetracycline-inducible system for conditional EGFR overexpression, these animals develop a highly penetrant (~100%) and aggressive lung adenocarcinoma after 4-8 weeks on a doxycycline-supplemented diet. Quantitative real-time PCR and western blotting with a monoclonal antibody specific to the activated EGFR allele were performed as previously described (Yu, J., et al. Clin Cancer Res 15, 3023-3028 (2009)). Mouse tumor samples obtained from EGFR$^{L858R}$ tetracycline-inducible mouse were evaluated for expression of human cDNA-derived EGFR$^{L858R}$ transgenic construct via qPCR analysis with hEGFR-specific primers and compared to wild-type littermates on doxycycline-supplemented diet. Western blot of tumor lysates using a monoclonal EGFR$^{L858R}$ Ab was used to confirm expression and activation of transgenic tetracycline-induced EGFR$^{L858R}$ construct and evaluated for wtKLF6 protein expression using a polyclonal KLF6 antibody recognizing a conserved region in mKLF6, normalized to mouse tubulin. Results confirmed increased expression of EGFR in the EGFR$^{L858R}$ mutant mouse-derived tumors as compared to normal lung tissue obtained from wild-type age- and sex-matched littermates on a doxycycline supplemented diet (FIG. 1e, g).

Figure 1F:
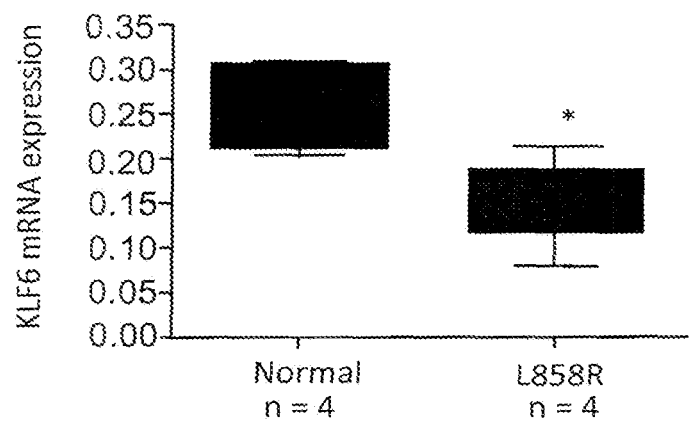
Figure 1G:
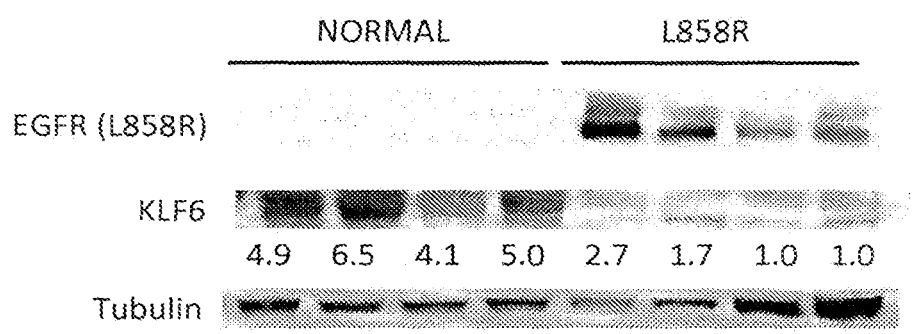

Mouse tissue samples analyzed by quantitative real-time PCR analysis for KLF6 mRNA expression with mouse-specific KLF6 PCR primers were normalized to endogenous mouse housekeeping transcript, cyclophilin. EGFR activation in this murine model of the disease was associated with a greater than 50% decrease in KLF6 expression at both the mRNA and protein level (FIG. 1f, g).

These results demonstrate the association between EGFR-activation and transcriptional down-regulation of the KLF6 tumor suppressor in lung adenocarcinoma.

Example 3

KLF6 is Transcriptionally Upregulated by Anti-EGFR-Based Therapy and Mediates the Apoptotic Response to Erlotinib in Human Lung Adenocarcinoma Cell Lines The effects of the anti-EGFR agent, erlotinib, on KLF6 expression were examined in treatment-resistant and sensitive human lung adenocarcinoma cell lines. Resistance to EGFR-based therapies commonly develops through several distinct genetic mechanisms, most notably gatekeeper mutations in the receptor, e.g. T790M which alters the affinity for the receptor for ATP. In addition, dysregulated activity of downstream mediators of EGFR signaling, such as PTEN, PI3K and K-Ras or amplification of the MET proto-oncogene can also drive the resistant phenotype. To test the effects of anti-EGFR-based therapy on KLF6 expression, the relative erlotinib sensitivity was determined in a panel of four commonly used lung adenocarcinoma cell lines with a variety of the molecular alterations in either EGFR or downstream mediators of its signaling pathway (FIG. 2a). Increasing doses of erlotinib were added as previously described (Sos, M. L., et al. Cancer Res 69, 3256-3261 (2009)) and cellular apoptosis was measured using a combination of fluorescence-activated cell-sorting (FACS) analysis (through determination of the sub-G1 fraction) (FIG. 2b) and western blotting for cleaved PARP (FIG. 2c) and activated Caspase 3 (data not shown). Results showed the HCC827 cell line, harboring an exon 19 deletion, was highly sensitive to erlotinib with a measured IC$_{50}$ of 50 nm. In contrast, the A549, H2122, and H1975 cell lines—with K-Ras and T790M EGFR mutations, respectively—were relatively resistant to erlotinib-mediated apoptosis (IC$_{50}$>500 nm). Tumors formed due to activating EGFR mutations were thus sensitive to anti-EGFR-based therapies, whereas tumors formed due to mutations in either K-Ras or the T790M EGFR mutation were resistant to erlotinib. Sos, M. L., et al. Cancer Res 69, 3256-3261 (2009); Cragg, M. S., et al. Plos Medicine 4, 1681-1690 (2007); Mitsudomi, T., et al. Oncogene 6, 1353-1362 (1991).

Figure 2D:
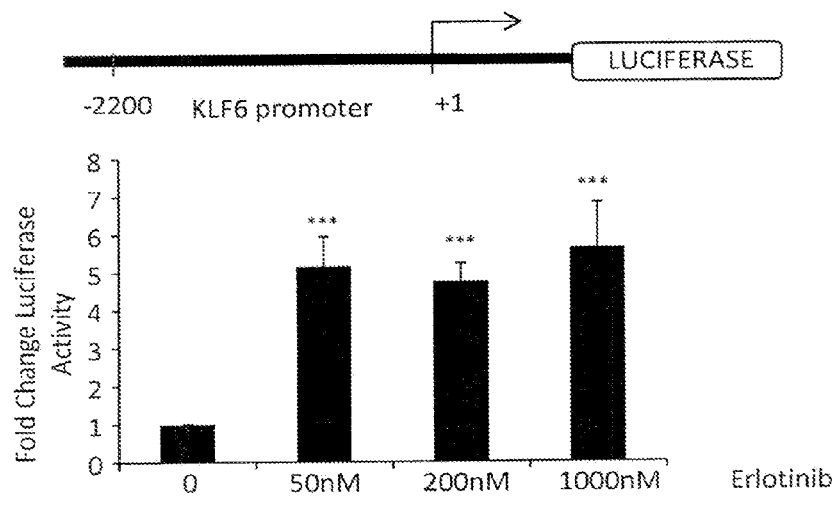
Figure 2E:
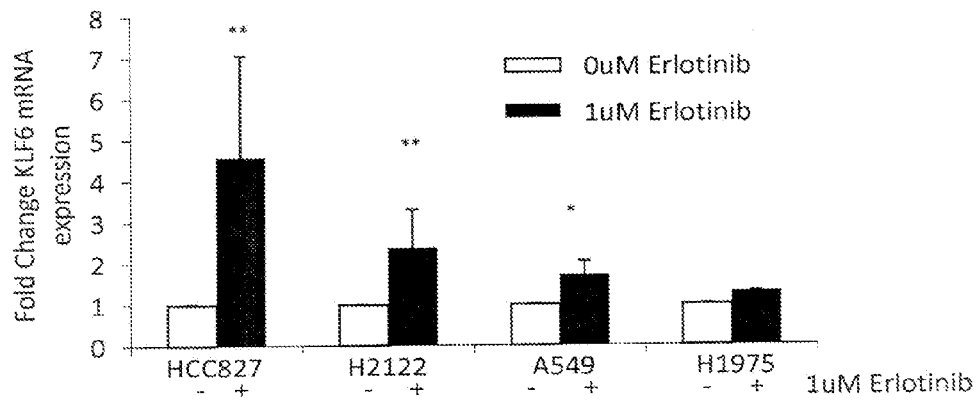
Figure 2F:
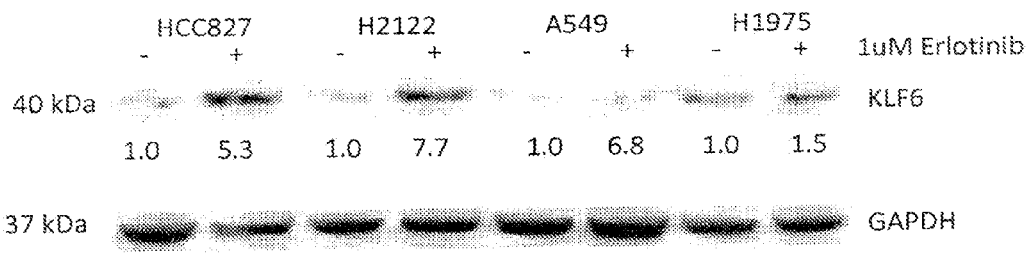

The variable sensitivity of the lung adenocarcinoma cell lines to anti-EGFR-based therapy was used to determine the effects of EGFR inhibition on KLF6 gene transcription. The effects of erlotinib on KLF6 promoter activity were analyzed using a hybrid 2.2 kb KLF6 promoter-luciferase construct (Yea, S., et al. Gastroenterology 134, 1521-1531 (2008)) in the erlotinib-sensitive lung adenocarcinoma HCC827cell line (FIG. 2d). Treatment of this erlotinib-sensitive cell line with erlotinib induced a five-fold increase in KLF6 promoter activity at doses that induced apoptosis and downregulation of key signaling mediators of EGFR signaling (FIG. 2d and data not shown). Significant upregulation of KLF6 gene expression in response to erlotinib treatment was also observed at the endogenous mRNA and protein levels in the treatment-sensitive cell line, HCC827, as compared to the resistant cell line H1975 (FIG. 2e, f). Treatment of H2122 and A549 lung adenocarcinoma cell lines harboring activating K-Ras mutations with erlotinib did not result in a significant induction of apoptosis (FIG. 2b, c). KLF6 expression was still upregulated, however, at both the mRNA and protein levels (FIG. 2e, f). Analysis of downstream regulators of EGFR signaling including ERK and AKT confirmed that erlotinib treatment of the H2122 and A549 cell lines resulted in marked reduction of activated AKT signaling with no changes in downstream ERK signaling. These results were consistent with the K-ras driven resistant phenotype in these two lung adenocarcinoma cell lines and suggests that inhibition of AKT signaling pathway may regulate KLF6 gene transcription.

Figure 2G:
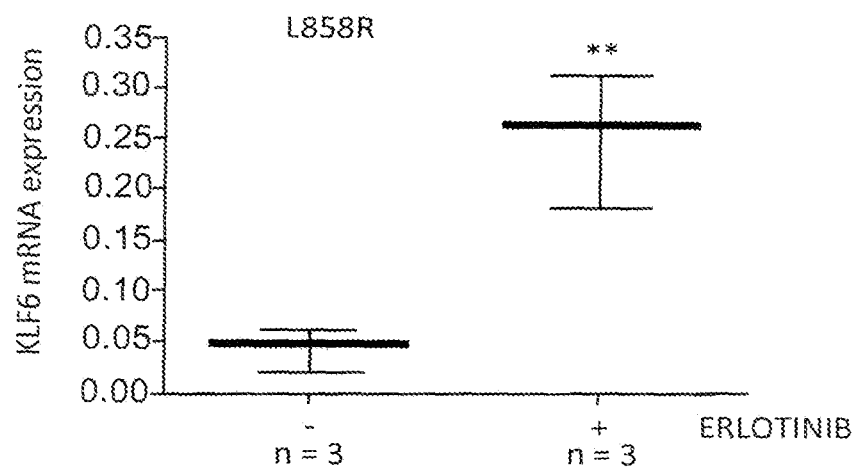
Figure 2H:
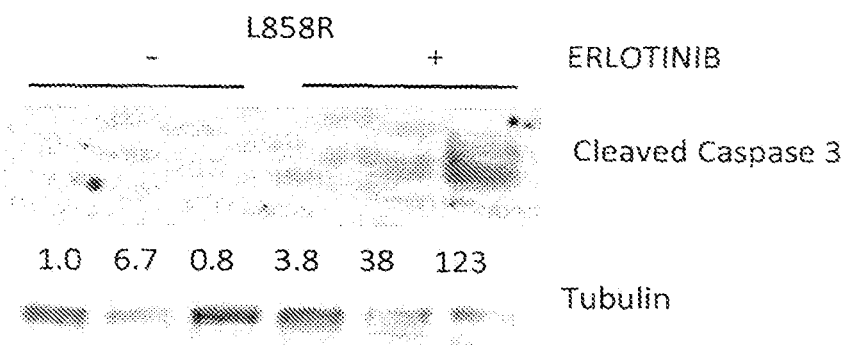

To corroborate this effect in vivo, experiments were performed using the $EGFR^{L858R}$ mouse model in which treatment with erlotinib results in spontaneous tumor regression in the mice. Politi, K., et al. Genes Dev 20, 1496-1510 (2006). Consistent with the cell culture data, tumors treated with erlotinib showed increased KLF6 expression at both the mRNA and protein level (FIG. 2g and data not shown). The upregulation of KLF6 in these tumors in vivo resulted in increased spontaneous apoptosis as demonstrated by increased Caspase 3 cleavage (FIG. 2h).

Figure 2I:
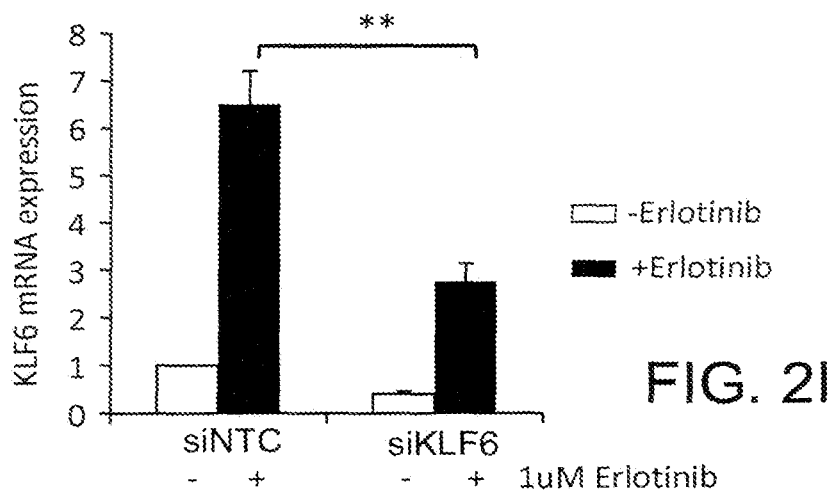
Figure 2J:
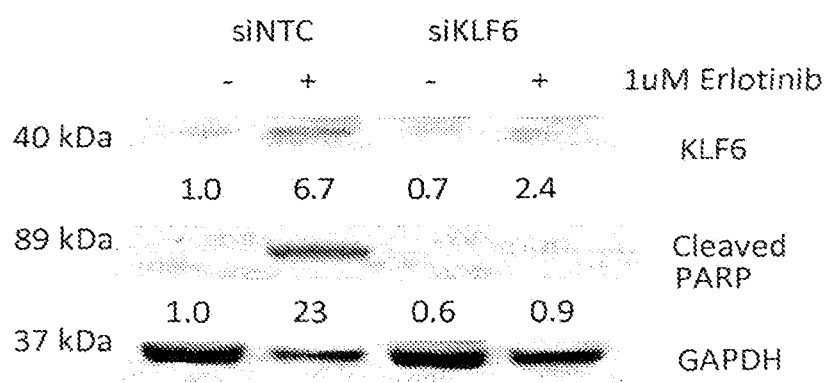
Figure 2K:
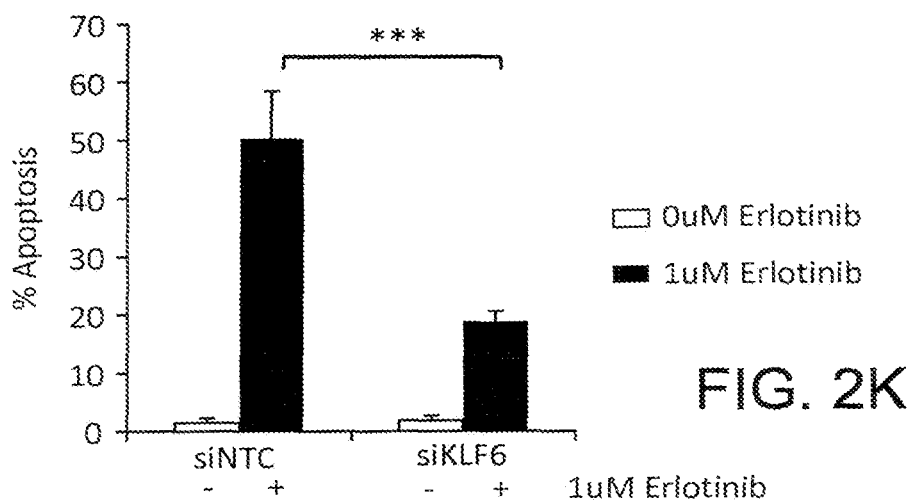

Previous studies have demonstrated that ectopic expression of KLF6 can induce spontaneous apoptosis in lung cancer cell lines. Ito, G., et al. Cancer Res 64, 3838-3843 (2004). To determine the biological effect of KLF6 upregulation on cellular apoptosis, sequence-specific siRNAs to wtKLF6 to were used to reduce upregulation of KLF6 expression in the HCC827 erlotinib-sensitive cell line. Transfection of the KLF6-specific siRNA (Camacho-Vanegas, O., et al. Int J Cancer 121, 1390-1395 (2007)) in the HCC827 cell line resulted in a greater than 50% downregulation of wtKLF6 expression at baseline and a greater than 80% downregulation of KLF6 at both the mRNA and protein level in presence of erlotinib in comparison to a scrambled siRNA control (FIG. 2i, j). Consistent with its function as a tumor suppressor gene in lung cancer, targeted reduction of KLF6 resulted in a marked reduction in erlotinib-driven apoptosis in the EGFR-activated cell line HCC827. This result was confirmed by both FACS analysis (FIG. 2k) and additional markers of apoptosis, including cleaved PARP and Caspase 3 expression as assessed by western blotting (FIG. 2j and data not shown). These results demonstrate that transcription of KLF6 was activated by inhibition of EGFR-driven AKT activation in both cell culture and in vivo models of the disease and that the resulting upregulation of KLF6 expression was necessary for the induction of apoptosis by anti-EGFR based therapy in metastatic lung cancer cell lines.

Example 4

EGFR-Driven AKT Activation Regulates KLF6 Transcription

Figure 3A:
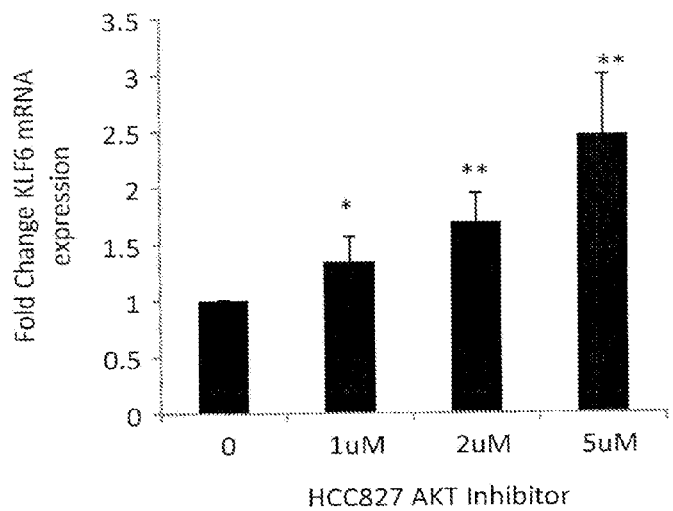
FIG. 3a-e shows results demonstrating that modulation of AKT signaling regulates KLF6. (a) Normalized KLF6 mRNA expression in cell-line HCC827 treated with AKT inhibitor for 72 hours; (b) Western blot of HCC827 cell lysates probed with antibodies to phosphorylated-AKT (P-AKT), total AKT (T-AKT), KLF6 and Actin and quantification of pAKT/AKT ratio; (c) Change in KLF6 promoter activity in A549-luc cell line 48 h after co-transfection of a KLF6 promoter construct and pBABE control or constitutively active AKTmyr plasmid; (d) Normalized KLF6 mRNA expression in A549-luc cell line 48 h after co-transfection of a KLF6 promoter construct and pBABE control or constitutively active AKTmyr plasmid; (e) Western blot of extracts from A549-luc cell line 48 h after co-transfection of a KLF6 promoter construct and pBABE control or constitutively active AKTmyr plasmid, probed with antibodies to phosphorylated-AKT (P-AKT), total AKT (T-AKT), KLF6, and GAPDH. Student's T-test reported with standard deviation. P values indicated as following: *P<0.05; P<0.01; *P<0.001, n=3 per data set.
Figure 3B:
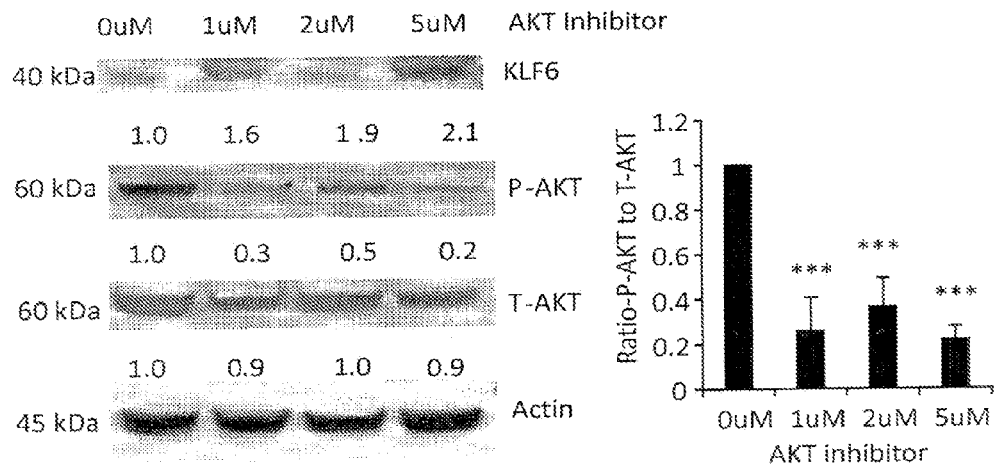

EGFR activates two major downstream pathways, the Ras-Raf-MAPK and the PI3K-AKT signaling cascades, resulting in both increased cellular proliferation and survival. Citri, A., et al. Nat Rev Mol Cell Biol 7, 505-516 (2006). The results presented above indicate that KLF6 expression is regulated by activated PI3K-AKT signaling cascade. The role of PI3K-AKT signaling cascade was tested utilizing an antagonist of AKT signaling that acts by inhibiting of the PDK1 and 2 kinases that activate AKT. Western blot analysis showed a dose-dependent decrease in AKT activation as assessed by phosphorylation of serine 473 (Sarbassov, D. D., et al. Science 307, 1098-1101 (2005)) with increasing doses of this AKT inhibitor in the HCC827 cell line (FIG. 3b). Inhibition of AKT signaling resulted in a dose-dependent upregulation of KLF6 at both the mRNA and protein level (FIG. 3a, b).

Figure 3C:
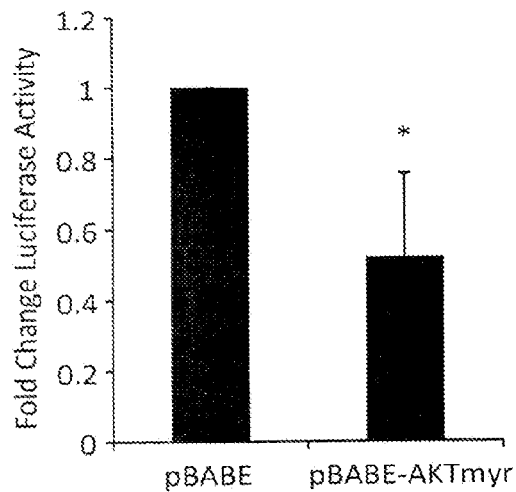
Figure 3D:
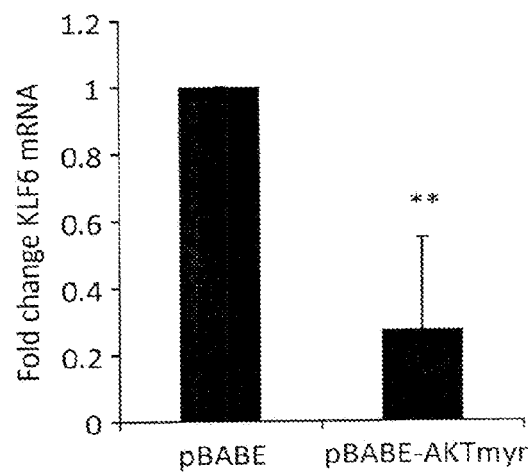
Figure 3E:
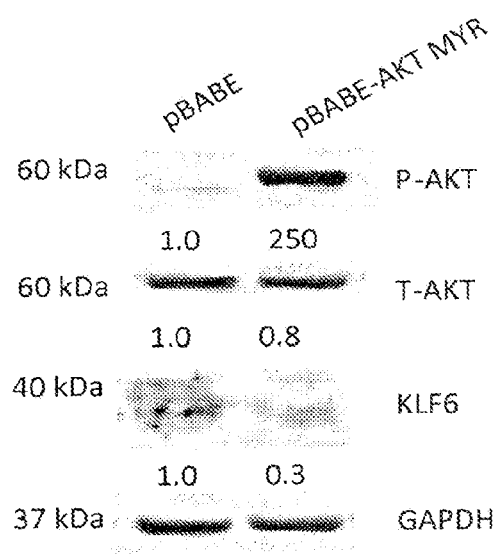

In order to further define the relationship between activated AKT signaling and KLF6 regulation, KLF6 promoter activity and KLF6 mRNA and protein levels were measured in A549 lung adenocarcinoma cell line that overexpressed a constitutively active form of AKT construct (Boehm, J. S., et al. Cell 129, 1065-1079 (2007)). Results showed that increased AKT signaling resulted in a marked reduction in KLF6 promoter activity and endogenous mRNA and protein expression of the KLF6 tumor suppressor (FIG. 3c, d, e). These results demonstrated that the KLF6 expression is negatively regulated by EGFR-driven activation of the PI3K-AKT signaling pathway in human lung adenocarcinoma.

Example 5

FOXO1 is a Transcriptional Regulator of KLF6 in Lung Adenocarcinoma

A key downstream regulator of PI3K-AKT signaling is the transcription factor FOXO1. Post-translational modification of FOXO proteins is a critical mechanism for regulation of their function. AKT-mediated phosphorylation maintains FOXO proteins in the cytoplasm and targets them for proteasome-mediated degradation. Pao, W., et al. PLoS Med 2, e73 (2005). KLF6 is a direct transcriptional target of FOXO1. Terragni, J., et al. BMC Cell Biol 9, 6 (2008).

To examine the role of FOXO1 in regulation of KLF6, the effect of overexpression of FOXO1 was examined in the ras-mutated A549 lung adenocarcinoma cell lines. A549 cells were transiently transfected with pCINEO-FOXO1 construct and analyzed after 48 hrs for FOXO1 and KLF6 mRNA levels, respectively, via quantitative real-time PCR. Data was normalized to GAPDH (similar results were obtained with normalization to 18S and Actin as housekeeping controls), results were calculated as fold change mRNA expression compared to control cells transfected with pCI-NEO. KLF6 promoter activity was measured by a dual-reporter assay in the presence of FOXO1 overexpression and results were calculated as fold change compared to control vector-transfected cells. To determine if FOXO1-driven transcriptional activation of KLF6 was necessary for erlotinib-mediated apoptosis in treatment sensitive cell lines, the effect of siRNA to FOXO1 on the apoptotic response to anti-EGFR therapy was examined. FOXO1 and KLF6 mRNA expression were determined by quantitative real-time PCR, normalized to GAPDH, in A549 cells 48 h after transfection with sequence specific siRNAs to FOXO1 (siFOXO1) or control construct (siNTC). Western blots were used to determine the expression of the apoptotic markers PARP and caspase-3, normalized to GAPDH, 48 hours after treatment with siFOXO1.

Figure 4A:
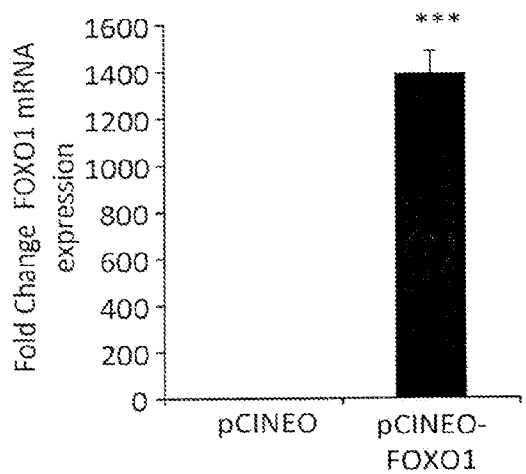
FIG. 4a-g shows results demonstrating transcription factor FOXO1 modulates KLF6 expression in A549 cells transiently transfected with pCINEO-FOXO1. (a) Normalized FOXO1 mRNA levels; (b) KLF6 promoter activity; (c) Normalized KLF6 mRNA levels; (d) Western blot for wtKLF6, FOXO1, and GAPDH protein expression after transfection of FOXO1 construct; (e) FOXO1 mRNA expression (f) KLF6 mRNA expression, and (g) Western blot analysis 48 h after transfection with sequence specific siRNAs to FOXO1. Experiments were repeated three independent times; data is presented as means, reported with error bars (±standard deviation) and P values are as follows, *P<0.05; P<0.01; *P<0.001, Student's T-test.
Figure 4B:
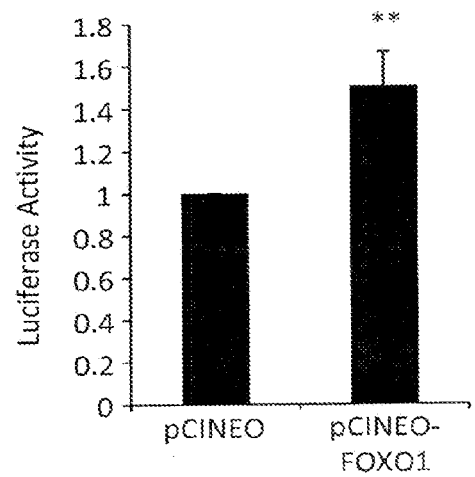
Figure 4C:
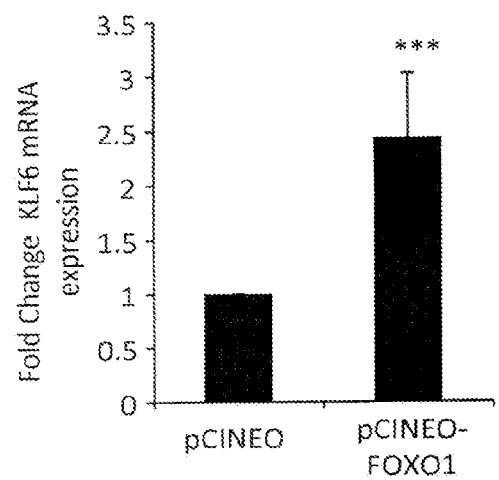
Figure 4D:
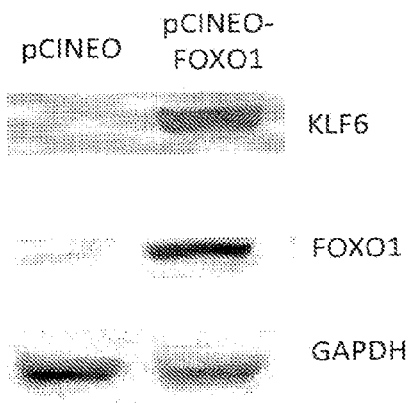
Figure 4E:
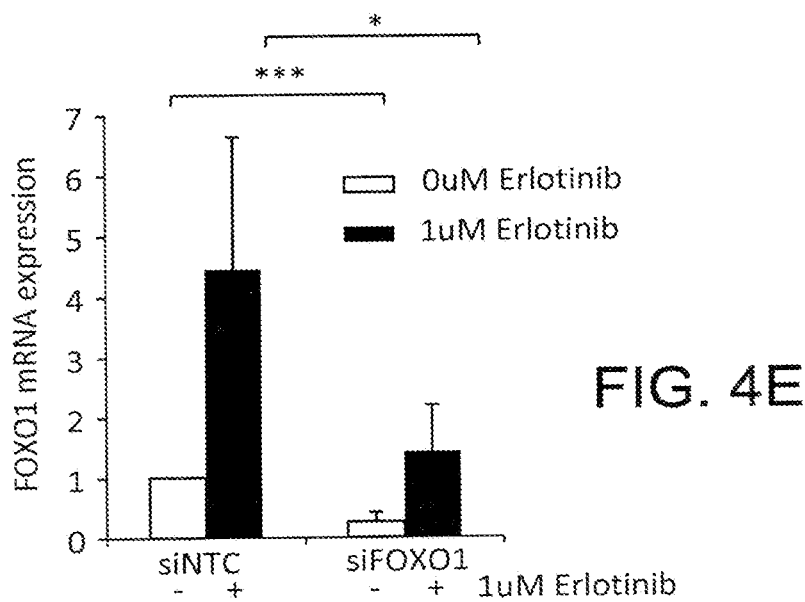
Figure 4F:
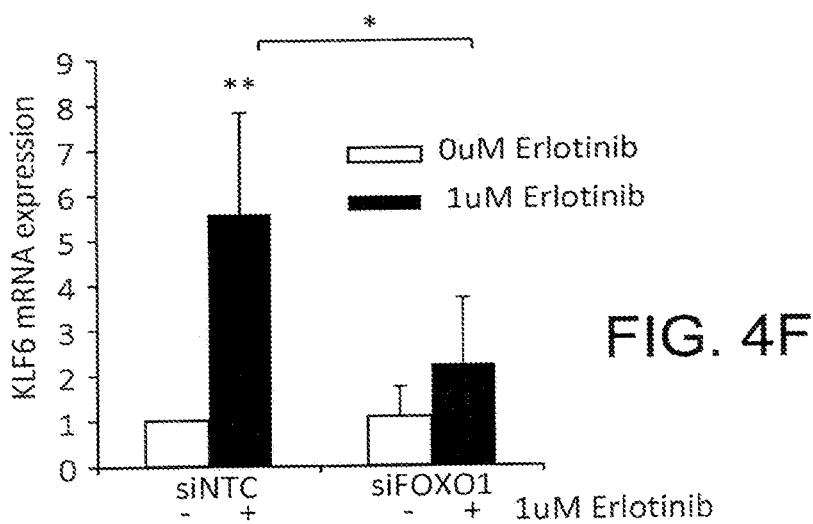
Figure 4G:
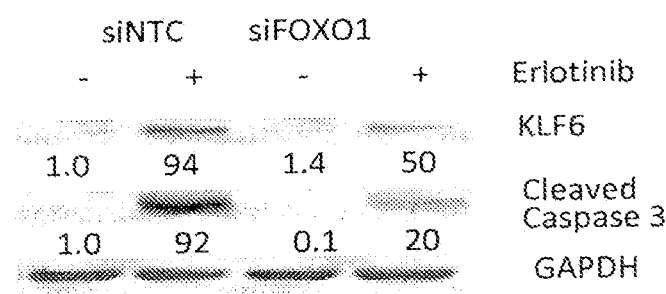

Results showed that overexpression of FOXO1 in the A549 lung adenocarcinoma cell lines increased KLF6 promoter activity, mRNA, and protein expression (FIG. 4a-d). Silencing of FOXO1 using sequence specific siRNAs (FIG. 4e), by comparison, reduced erlotinib-induced KLF6 upregulation (FIG. 4b, g). FOXO1 silencing also resulted in decreased KLF6 upregulation and decreased induction of apoptosis by anti-EGFR-based therapy in the HCC827 cell line, as indicated by cleaved Caspase 3 (FIG. 4g) and PARP expression (data not shown).

To investigate the role of KLF6 and FOXO1 regulation in human lung adenocarcinoma, a retrospective analysis was performed on the cohort of 13 matched patient-derived tumor and adjacent normal lung samples. Quantitative real-time PCR and western blotting for both KLF6 and FOXO1 on the same cohort of patient-derived tumor and adjacent normal lung tissues were used to correlate the expression of these two transcription factors in vivo. AKT status was determined using western blotting for phospho-AKT compared to total-AKT levels, with "AKT activation" being defined as higher levels of the ratio in tumor compared to matched surrounding lung tissue from each individual patient.

Figure 5A:
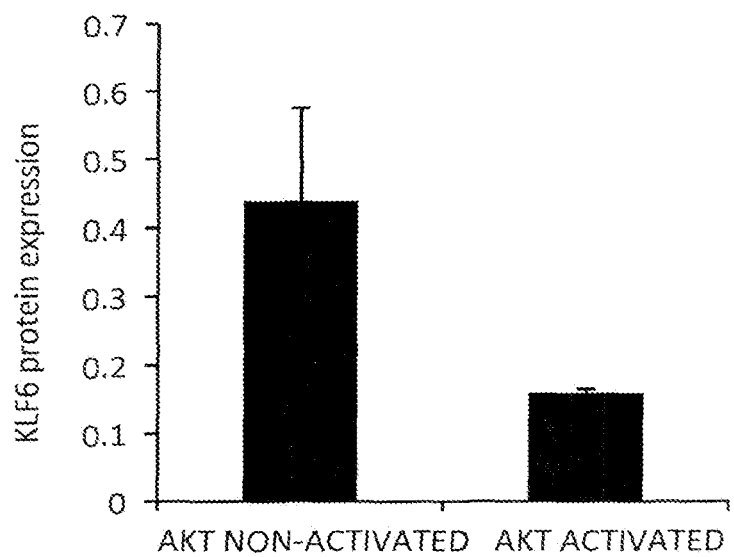
FIG. 5a-d shows results demonstrating decreased FOXO1 expression correlated with downregulation of KLF6 expression in a mouse model and human primary lung adenocarcinomas. (a) Western blot densitometry quantitation of KLF6 protein expression in AKT-activated versus non-AKT activated human tumor samples; (b) Western blot analysis of representative matched tumor and normal samples from human patients probed with P-AKT, T-AKT, KLF6 and GAPDH antibodies; (c) Western blotting analysis of lung tissue protein extract from PTEN+/− mice and wild-type age-matched litter-mates with antibodies to PTEN, phosphorylated-AKT (P-AKT), total AKT (T-AKT), phosphorylated-FOXO1 (P-FOXO1), total FOXO1 (T-FOXO1) and KLF6; and (d) KLF6 mRNA expression in PTEN+/− mice as compared to wild-type age-matched litter-mates.
Figure 5B:
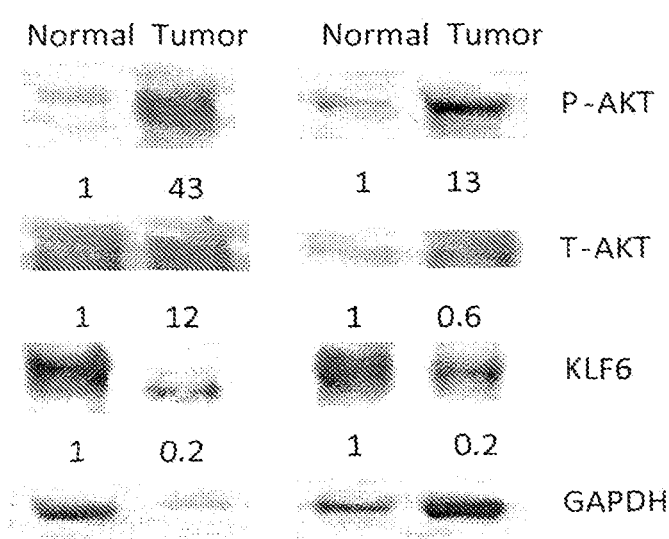

Western blot analysis of phosphorylated AKT (p-AKT) and total AKT (T-AKT), showed that tumors exhibited increased AKT signaling (as determined by an increased ratio of p-AKT/T-AKT in the tumor tissue, compared to matched surrounding lung tissue from the same patient) and expressed significantly lower levels of KLF6 (FIG. 5a, b). These results demonstrated that KLF6 was downregulated in tumors in AKT activated cancer, compared to normal tissue. Absolute expression levels of KLF6 and FOXO1 were positively correlated, indicating the FOXO1 protein levels were also reduced in tumors in AKT activated cancer, compared to normal tissue (correlation coefficient of $R^2=0.4069$ (number of XY pairs=35; Pearson r=0.6379; 95% confidence level=0.3868 to 0.8009; P value (two-tailed=P<0.0001; significant correlation (alpha=0.05)).

Figure 5C:
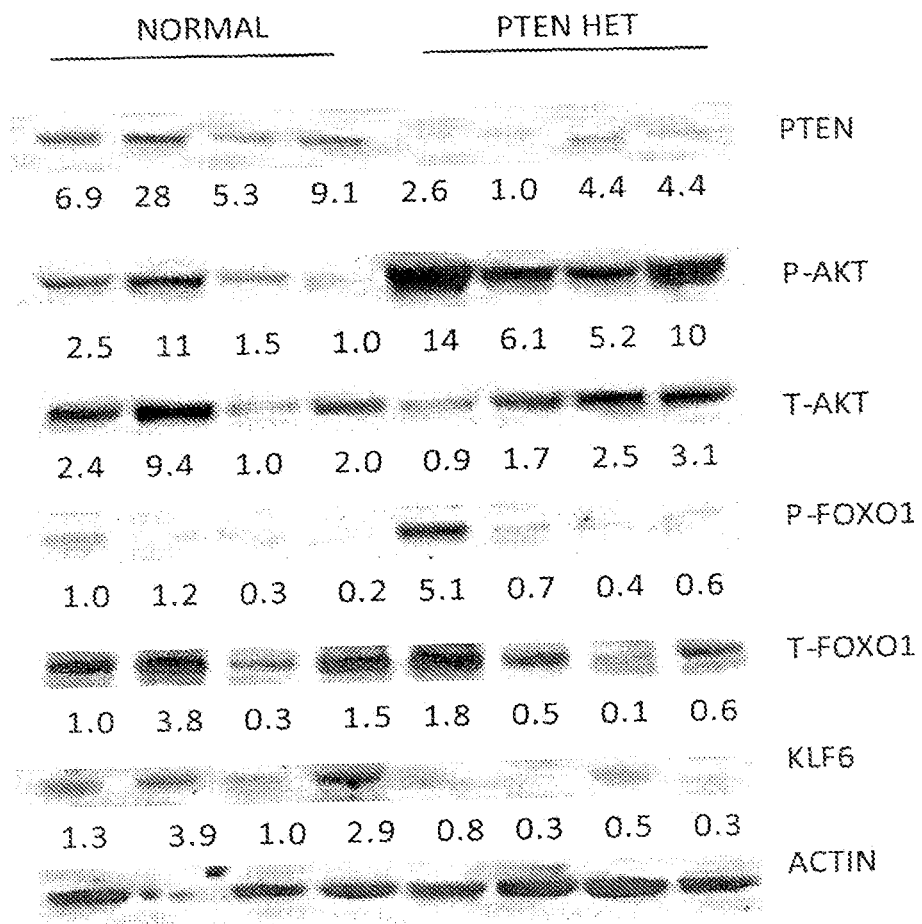
Figure 5D:
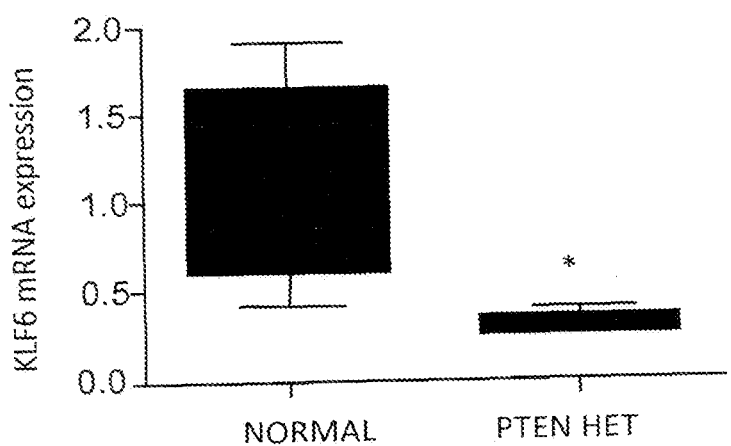

To further define the association between increased AKT signaling and decreased expression of FOXO1 and KLF6 in vivo, the expression of these two transcription factors were studied in lung tissue derived from normal and Pten/Mmac1+/− heterozygous mice. Podsypanina, K., et al. Proc Natl Acad Sci USA 96, 1563-1568 (1999). Western blot analysis showed that loss of one PTEN allele, resulted in increased AKT signaling and subsequently increased phosphorylation of FOXO1 (FIG. 5c). Consistent with the cell culture and patient derived tumor data, activated AKT signaling was associated with decreased KLF6 mRNA and protein expression as assessed by quantitative real-time PCR and western blotting in heterozygous PTEN mice compared to age-matched/sex-matched wild-type littermates (FIG. 5c, d).

Figure 6A:
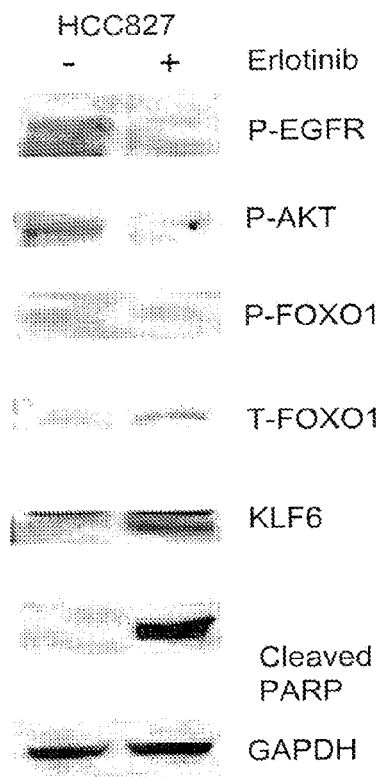
FIG. 6a-c shows results demonstrating that inhibition of EGFR-signaling causes upregulation of KLF6 expression via increased accumulation of nuclear FOXO1. (a) Western blot analysis of HCC827 cells treated with 50 nM erlotinib and control, untreated cells, probed with antibodies to P-EGFR, P-AKT, P-FOXO1, KLF6, PARP, and GAPDH; (b) Western blot analysis of nuclear and cytoplasmic fraction of HCC827 cells treated with 50 nM erlotinib and control, untreated cells, probed with antibodies to T-FOXO1, KLF6, Histone H3, and GAPDH; (c) FOXO1 protein levels in human lung adenocarcinoma tumors, compared to matched control, normal tissue from the same patient.
Figure 6B:
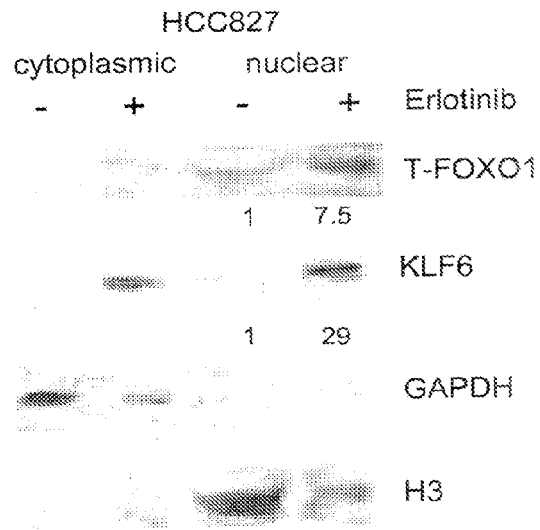
Figure 6C:
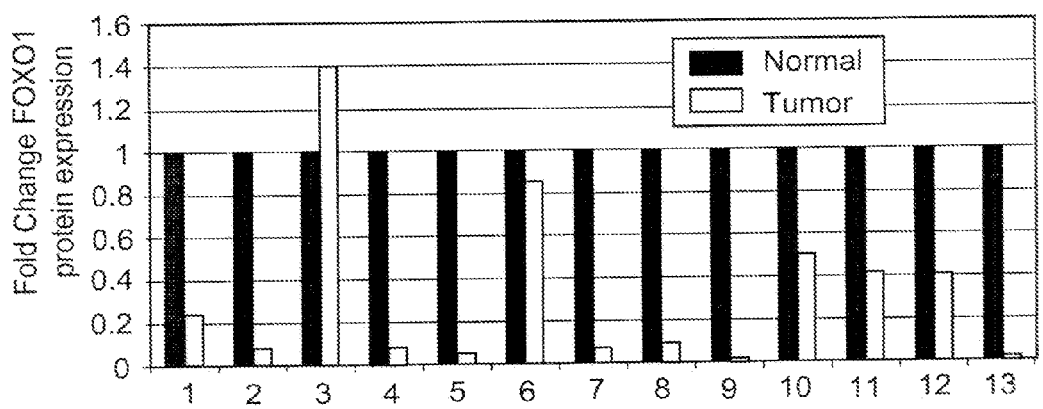

The effect of erlotinib on the EGFR-FOXO1-KLF6 signaling pathway was examined by comparing protein levels in HCC827 cells treated with 50 nM erlotinib to untreated controls. Western blotting analysis with antibodies to phosphorylated EGFR (P-EGFR), phosphorylated-AKT (P-AKT), phosphorylated FOXO1 (P-FOXO1), total FOXO1 (T-FOXO1), KLF6, PARP, and GAPDH antibodies showed that erlotinib treatment reduced phosphorylated forms of EGFR, AKT and FOXO1, increased total amount of FOXO1, and increased cleaved PARP (FIG. 6a). Fraction of erlotinib-treated and untreated, control cells demonstrated that nuclear localization of FOXO1 and KLF6 increased upon erlotinib treatment. (FIG. 6b) In a separate set of experiments, FOXO1 protein levels were shown to be reduced in human lung adenocarcinoma tumors, compared to matched control, normal tissue from the same patient (FIG. 6c) and the relative amount of FOXO1 localized to the nucleus was lower in human lung adenocarcinoma tumors (data not shown). These results demonstrated that inhibition of EGFR signaling results in decreased AKT signaling and increased FOXO1 nuclear localization, which results in increased KLF6 expression and increased KLF6 nuclear localization. These data demonstrate the presence of a signaling network in which inhibition of EGFR signaling results in decreased AKT activation and increased nuclear accumulation of FOXO1, thus leading to transactivation of the KLF6 tumor suppressor gene and induction of apoptosis (FIG. 6a, b).

Example 6

Figure 7D:
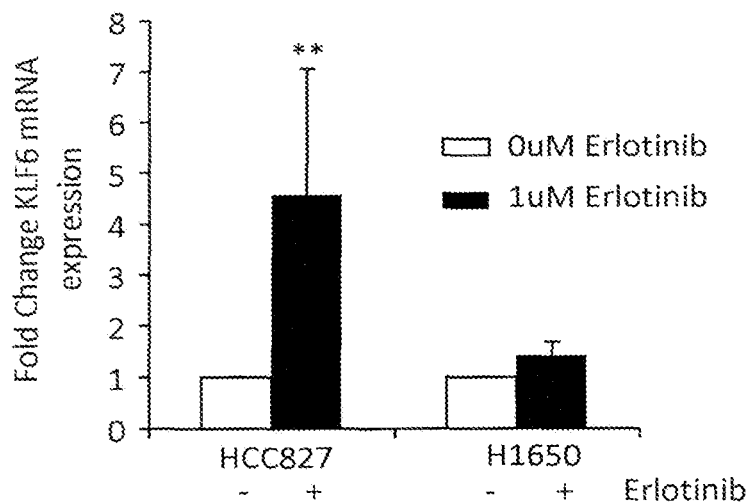
Figure 7E:
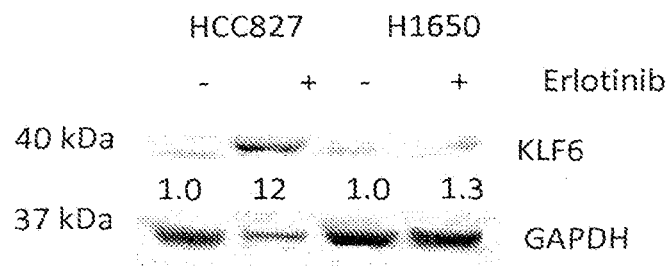

Upregulation of the KLF6 Tumor Suppressor is Required for Erlotinib Response in Both Cell Culture and In Vivo The role of KLF6 in induction of apoptosis in response to anti-EGFR therapeutics was further tested in cell culture. The H1650 and HCC827 cell lines are respective models for anti-EGFR treatment sensitivity and resistance. Both cell lines harbor the del746-50 activating mutation in EGFR that should render them sensitive to anti-EGFR based therapies (FIG. 7a). The H1650 cell line, however, is resistant to erlotinib, due to loss depletion of the PTEN tumor suppressor gene that results in constitutive AKT activation (FIG. 7a). Compared to untreated controls, HCC827 cell lines treated with 1 μM erlotinib for 48 h exhibited significantly increased levels of apoptosis, as measured by FACS analysis by sub-G1 propidium iodide staining (FIG. 7b) and cleaved PARP (FIG. 7c). The erlotinib-resistant H1650 cell line showed no increase in apoptosis following erlotinib treatment (FIG. 7b, c). KLF6 expression was significant upregulated in the treatment-sensitive HCC827 cell line and not in the resistant H1650 cell line (FIG. 7d, e).

Figure 8A:
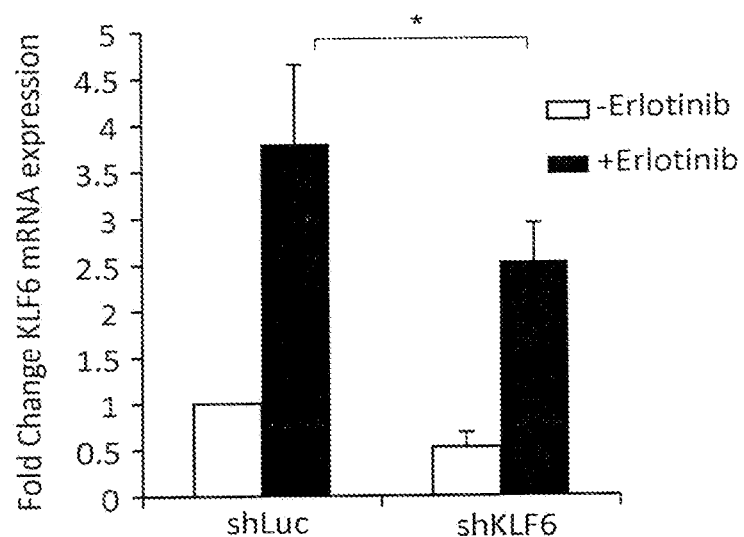
FIG. 8a-d shows results demonstrating stable knockdown of KLF6 in the erlotinib-sensitive HCC827 cell line confers drug resistance in culture and in vivo. (a) Wild-type KLF6 expression, (b) Western blot analysis, (c) Apoptosis levels, and (d) Tumor growth rates in control cell line shLuc-HCC827 and stable knockdown cell line shKLF6-HCC827, either untreated or treated with 50 nM erlotinib.
Figure 8B:
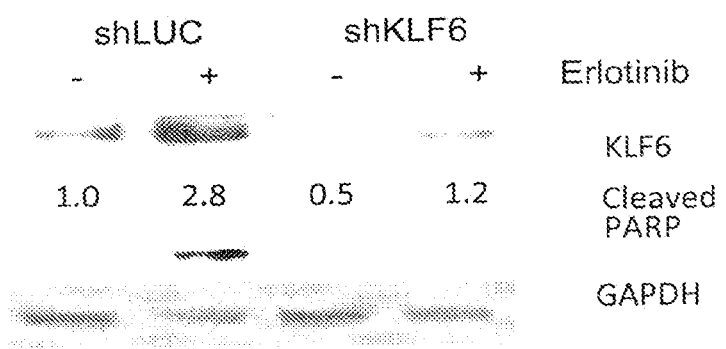
Figure 8C:
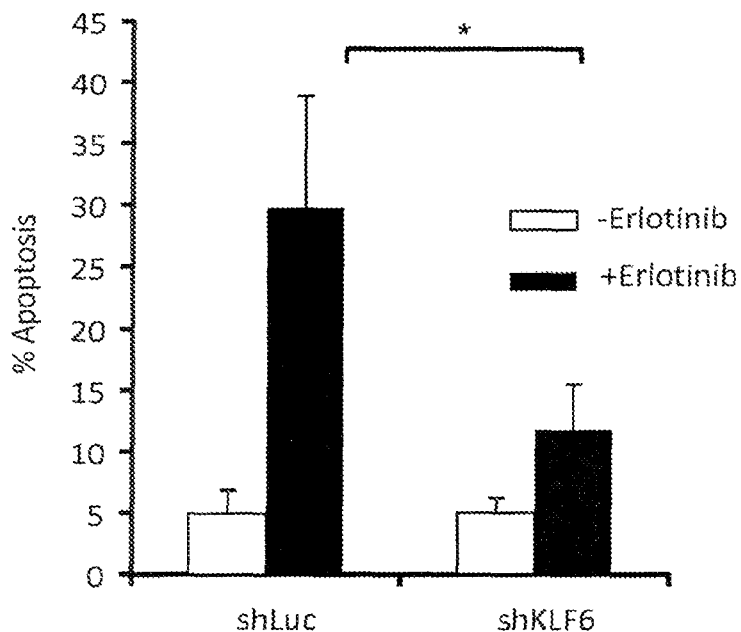

To determine whether the upregulation of KLF6 was necessary for anti-EGFR based therapy response in culture and in vivo, short hairpin RNA interference was used to stably reduce KLF6 in the HCC827 cell line. Control cell line shLuc-HCC827 and cell line shKLF6-HCC827 were left untreated or treated with 50 nM erlotinib for 48 h. Expression of KLF6 RNAi reduced KLF6 expression (FIG. 8a, b) in the HCC827 cell line. Expression of KLF6 RNAi also decreased erlotinib driven apoptosis, as demonstrated by decreased PARP cleavage (FIG. 8b) and flow cytometric analysis of the sub-G1 cell cycle fraction via propidium iodide staining (FIG. 8c). This result was confirmed using a clonogenic assay, where treatment with 50 nM erlotinib for 7 days resulted in a decreased colony formation in control shLuc but not in the shKLF6 cell line.

Figure 8D:
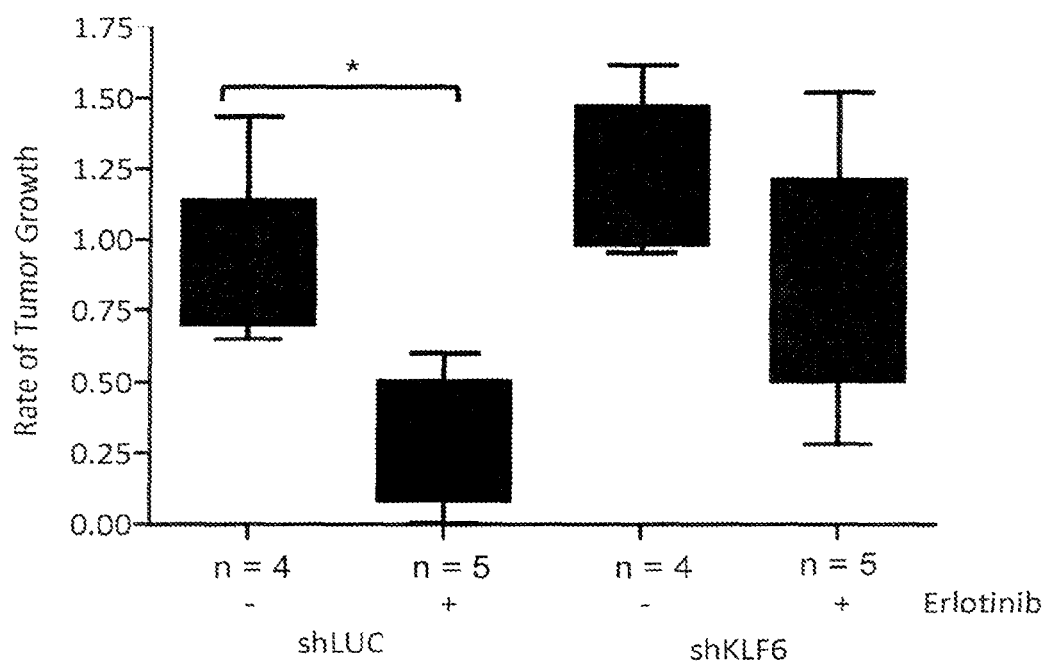

KLF6-dependence of anti-EGFR based therapy was tested in vivo using an animal model of the disease. Tumors were induced by subcutaneous injection of shLuc-HCC827 or shKLF6-HCC827 stable cell lines ($1 \times 10^6$ cells/injection) into right posterior flank of nude mice (n=18). Upon reaching an average volume of 150 mm$^3$, tumors were divided among 4 treatment groups: shLuc-HCC827 treated with vehicle (DMSO) (n=4), shLuc-HCC827 treated with 20 mg/kg erlotinib (n=5), shKLF6-HCC827 treated with vehicle (n=4), and shKLF6-HCC827 treated with 20 mg/kg erlotinib (n=5). Tumor growth was measured 24 hours after injection. Results showed that erlotinib treatment of the shKLF6-HCC827-derived tumors did not significantly decrease the rate of tumor growth, while erlotinib treatment of the shLuc-HCC827-derived tumors treated with erlotinib were markedly smaller than the DMSO treated control group. (FIG. 8d).

These data confirm that transcriptional activation of the KLF6 tumor suppressor gene is required for anti-EGFR based therapy response in both cell culture and mouse models of advanced lung cancer and suggest that anti-EGFR treatment resistance could be overcome by restoring downstream function of the FOXO1/KLF6 transcriptional network.

Example 7

Inhibition of FOXO1 Nuclear Export Increases KLF6 Expression

Trifluoperazine Hydrochloride (TFP), a FDA-approved antipsychotic and antiemetic, is an effective nuclear export inhibitor of the FOXO1 transcription factor that increases FOXO1 nuclear localization via calmodulin inhibition upstream of AKT and downstream of PI3K. Kau, T. R., et al. Cancer Cell 4, 463-476 (2003). TFP was used to inhibit nuclear export of FOXO1 and determine if activation of the FOXO1/KLF6 transcriptional network could restore sensitivity to the PTEN-depleted, erlotinib-resistant cell line, H1650. To examine the effect of TFP on nuclear localization of FOXO1 and, subsequently, KLF6 expression, H1650 cells were treated for 1 h with increasing doses of TFP (0, 20 µM, 40 µM) and fractionated into nuclear and cytoplasmic fractions. BRCA1 served as a nuclear marker and GAPDH served as a cytoplasmic marker for the fractionation.

Figure 9A:
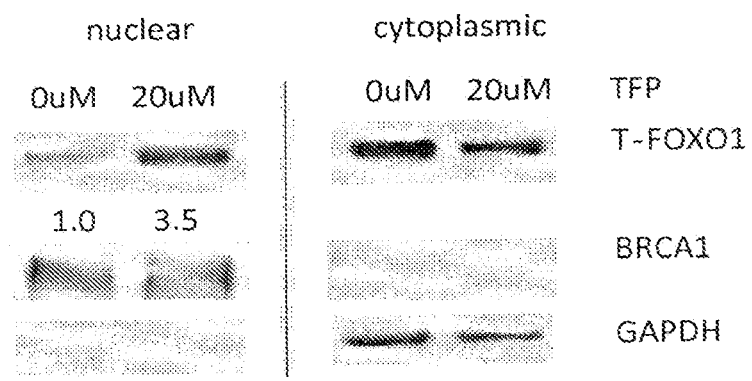
FIG. 9a-g shows results demonstrating inhibition of FOXO1 nuclear export results in upregulation of KLF6 expression and increased apoptosis. (a) Western blot analysis of nuclear and cytoplasmic fractions of H1650 cells, untreated controls or 1 h treatment with 20 µM TFP, and probed with antibodies to FOXO1, BRCA1, and GAPDH; (b)-(c) Apoptosis in H1650, untreated controls or 1 h treatment with 40 µM TFP analyzed by (b) percent of gated sub-G1 cell cycle fraction as measured by FACS analysis of nuclear DNA content identified by propidium iodide staining and (c) western blot analysis of PARP, cleaved Caspase 3 and GAPDH (control); (d) Normalized KLF6 mRNA expression levels in controls and H1650 cells treated 1 h and 48 h with 40 µM TFP; (e) Western blot analysis of extracts of controls and H1650 cells treated 1 h with 40 µM TFP and probed with antibodies to KLF6 and GAPDH; (f)-(g) Apoptotic response in control cells and cells treated separately or in combination with 1 µM erlotinib and/or 30 mM TFP, measured by (f) percent of gated sub-G1 cell cycle fraction on FACS identified by PI staining and (g) western blot for PARP, Caspase 3 (normalized to GAPDH). All data was repeated three independent times, results presented as means, error bars indicate±s.d., P values are as follows, *P<0.05; P<0.01; *P<0.001, Student's T-test. All western blots are representative of three independent experiments.
Figure 9B:
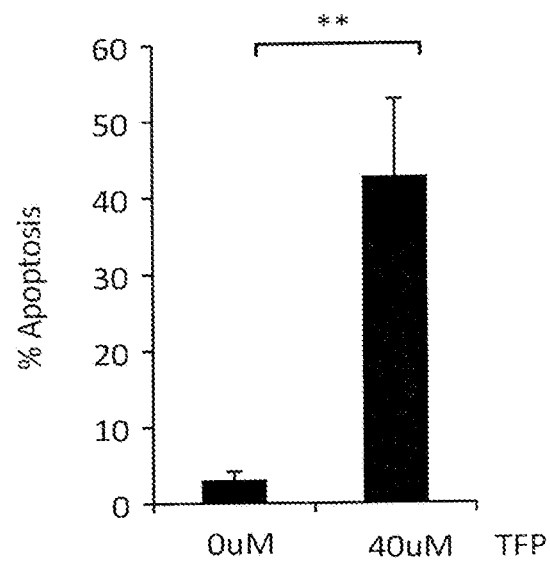
Figure 9C:
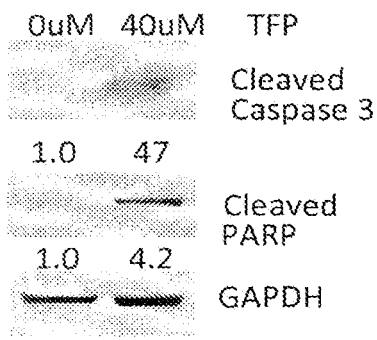
Figure 9E:
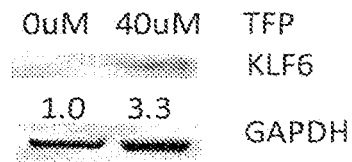
Figure 9D:
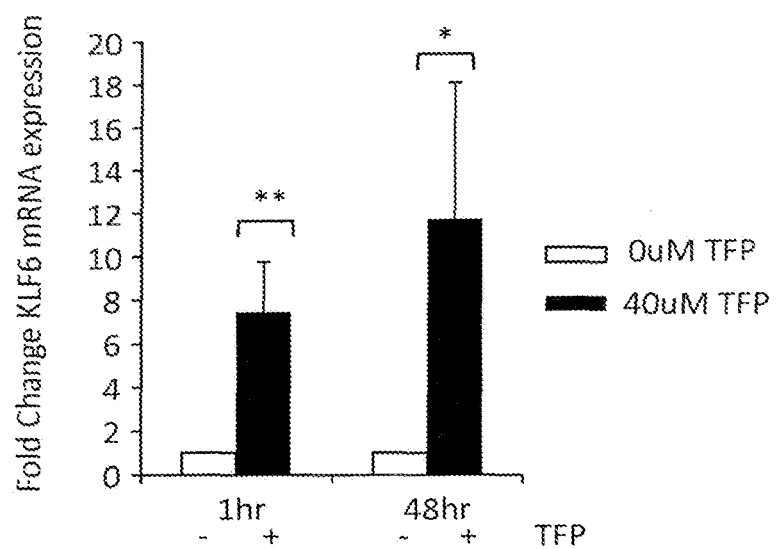
Figure 10A:
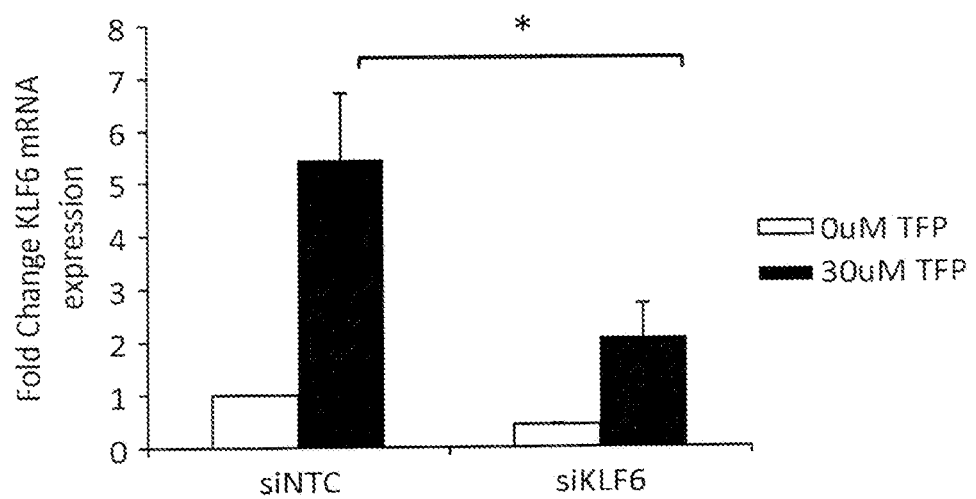
FIG. 10a-b shows results demonstrating that knockdown of KLF6 abrogates apoptotic response to TFP. (a) Normalized KLF6 mRNA expression 72 h after transient transfection with 100 mM siKLF6 and subsequent treatment with 30 µM TFP; (b) Western blot analysis of apoptosis markers PARP and cleaved Caspase 3 in response to siKLF6 transfection and subsequent treatment with 30 µM TFP.
Figure 10B:
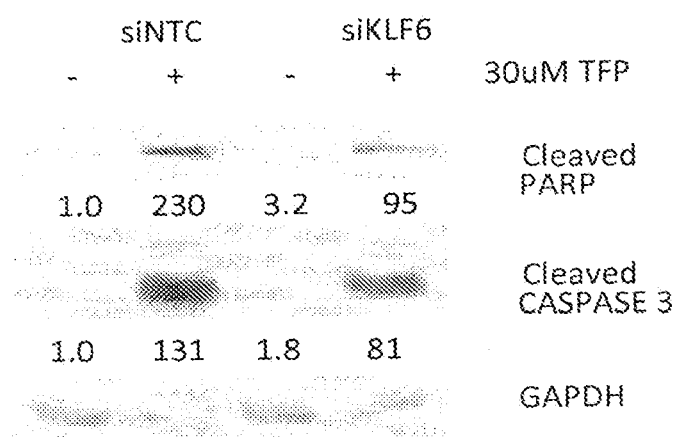

Western blot analysis of nuclear and cytoplasmic fractions confirmed that treatment for 1 h with 20 µM TFP increased nuclear FOXO1 expression (FIG. 9a). Treatment with 40 µM TFP for 1 h resulted in increased apoptosis as shown through FACS analysis and western blotting for cleaved PARP and cleaved Caspase 3 (FIG. 9b, c). Quantitative real-time PCR and western blotting confirmed concurrent upregulation of KLF6 mRNA and protein at 1 h and 48 h after treatment with 40 µM TFP (FIG. 9d, e). Inhibition of KLF6 with sequence specific siRNA, by comparison, inhibited KLF6 upregulation and decreased TFP-mediated apoptosis suggesting that the transcriptional upregulation of KLF6 by FOXO1 was required for TFP-induced apoptosis (FIG. 10a, b). These data suggest that increasing nuclear localization of FOXO1 could restores therapeutic response to anti-EFGR-based therapy through modulation of the expression of the FOXO1/KLF6 tumor suppressor gene transcriptional network.

Chlorpromazine was also shown to increase FOXO1 nuclear accumulation in NSCLC cell lines. Viability of cells line H1650, A549luc and H3255 were determined for cells grown in control medium and medium supplemented with 10 µM, 20 µM and 40 µM chlorpromazine. The respective $IC_{50}$ values for chlorpromazine determined for the cell lines were determined to be: H1650=20 µM, A549luc=20 µM, H3255=8 µM. Immunocytochemistry of H1650 cells showed that cells treated with 20 µM chlorpromazine at 48 hours resulted in significant nuclear accumulation of FOXO1, compared to untreated control cells. FACS analysis by sub-G1 propidium iodide staining of H1650 cells treated with increasing doses of CPZ for 48 hrs demonstrates increased amount of apoptosis in response to the drug. Combined, this data suggests a general class effect of phenothiazine based small molecules in relocalizing FOXO1 from the cytoplasm to the nucleus and in the induction of apoptosis in metastatic lung cancer cell lines.

Example 8

Figure 9F:
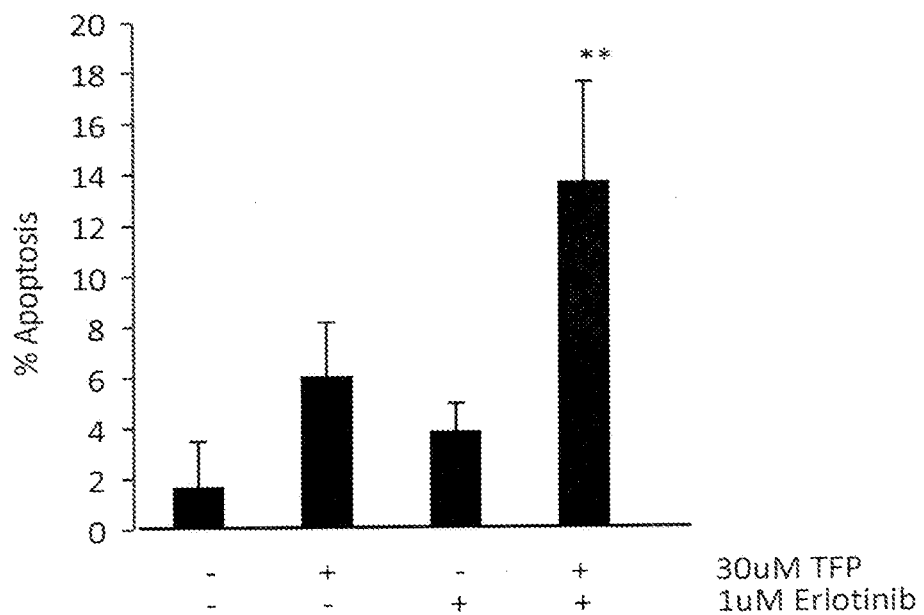
Figure 9G:
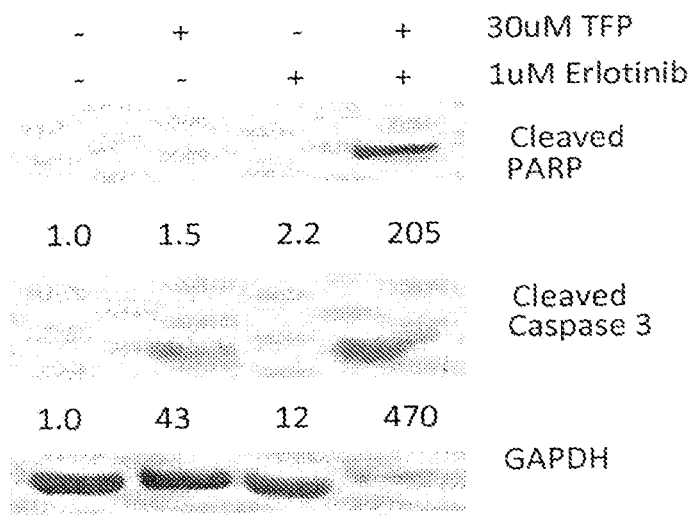

Combination Treatment with TFP and Erlotinib Increased Apoptosis and Decreased Tumorigenicity in a Resistant Cell Line In Vitro and In Vivo The effect of combining TFP and erlotinib treatments was examined in cell culture and an in vivo model of disease. FACS analysis showed an increase in the sub-g1 fraction of the cell cycle with the combination TFP-erlotinib treatment in the resistant H1650 lung adenocarcinoma cell line (FIG. 9f). Western blotting for apoptotic markers, cleaved PARP and Caspase 3, confirmed the increased induction of apoptosis in the presence of both TFP and erlotinib compared to either drug alone (FIG. 9g).

Figure 11A:
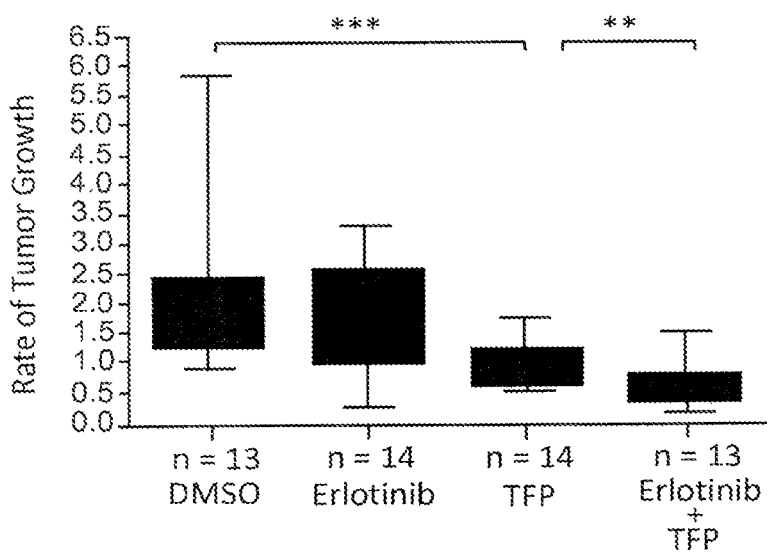
FIG. 11a-g shows results demonstrating trifluoperazine and erlotinib administered in combination decrease tumorigenicity in a xenograft model of lung adenocarcinoma. Subcutaneous lung adenocarcinoma-derived cell line xenograft tumors derived from injection into nude mice that were subsequently administered DMSO (vehicle control), erlotinib (80 mg/kg), TFP (20 mg/kg) or both (80 mg/kg erlotinib, 20 mg/kg TFP) were analyzed for (a) Growth rate, (b) Kaplan Meyer survival analysis, (c) KLF6 mRNA expression, (d) Western blot analysis, (e) KLF6 protein expression, (f) Quantification of TUNEL positive cells, and (g) Quantification of nuclear-localized proliferating-cell nuclear antigen (PCNA).
Figure 11B:
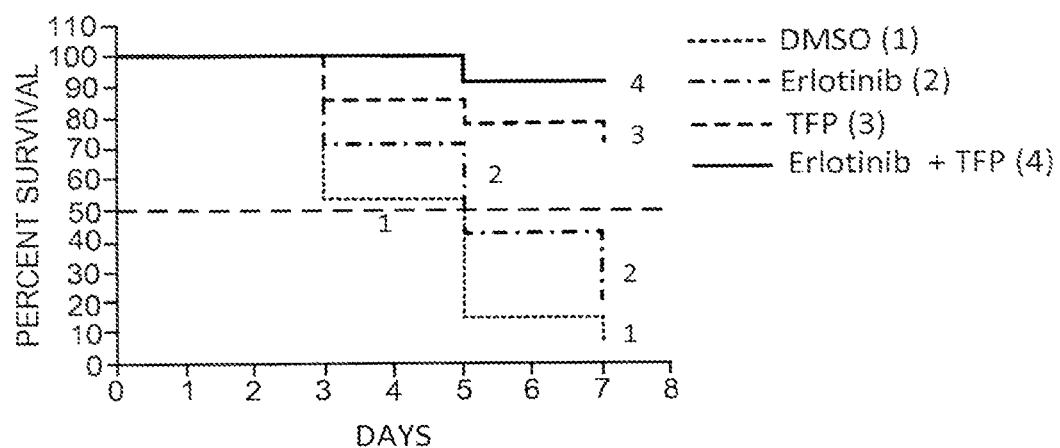
Figure 11C:
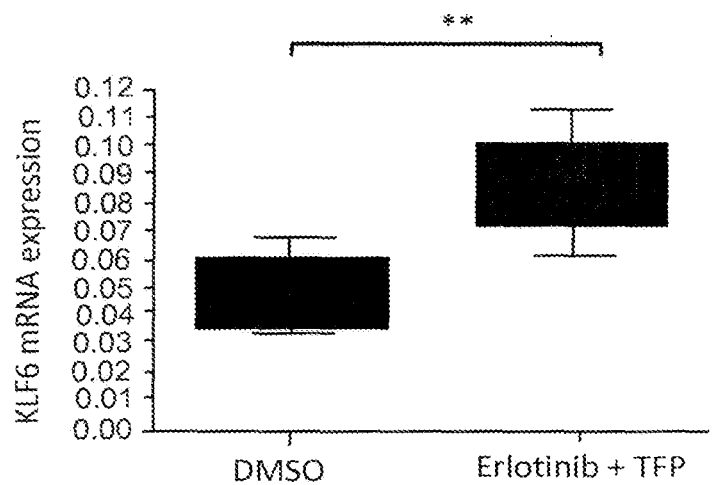
Figure 11D:
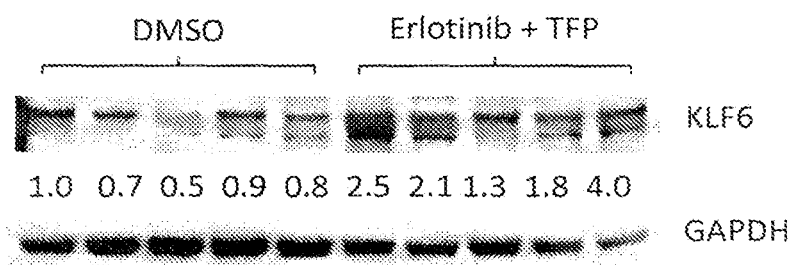
Figure 11E:
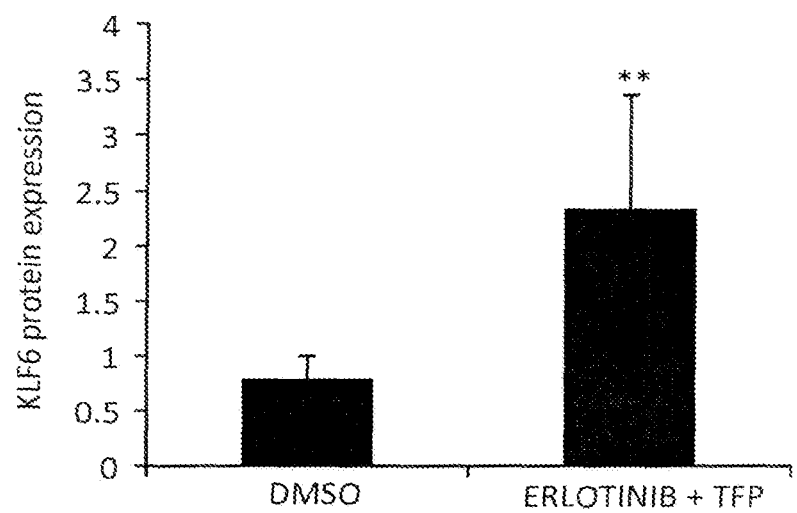

To examine the effect of combination treatment with TFP and erlotinib in vivo, the PTEN-depleted treatment-resistant cell line H1650 was injected subcutaneously into nude mice (n=54). Tumor growth was measured weekly until average tumor volume for all mice was approximately 200 mm³. Mice were then divided into four experimental groups that were treated as described in Example 1 with, respectively, vehicle (DMSO) (n=13), erlotinib (n=14), TFP (n=14), or erlotinib in combination with TFP (n=13). Tumor growth in H1650-injected nude mice was measured 24 hours after each drug injection. Tumor growth rates increased following treatment with vehicle control and erlotinib (FIG. 11a). Tumor growth rates decreased after treatment with TFP alone (FIG. 11a). Combination treatment with TFP and erlotinib showed a dramatic response, with an almost complete regression of tumor burden in the majority of mice (FIG. 11a). Survival analysis showed that combination treatment with erlotinib and TFP increased survival relative to DMSO or erlotinib alone (FIG. 11b). Quantitative real-time PCR analysis of control and TFP-Erlotinib treated tumors in homogenized tumor samples from H1650-injected mice treated and sacrificed 24 h after injection showed an increase in KLF6 expression at both the mRNA and protein level (FIG. 11c-e). Lysate homogenates from treated and untreated tumors were run and probed in parallel (n=5); statistical significance of densitometry calculations indicated (*P<0.05; P<0.01; *P<0.001).

Figure 11F:
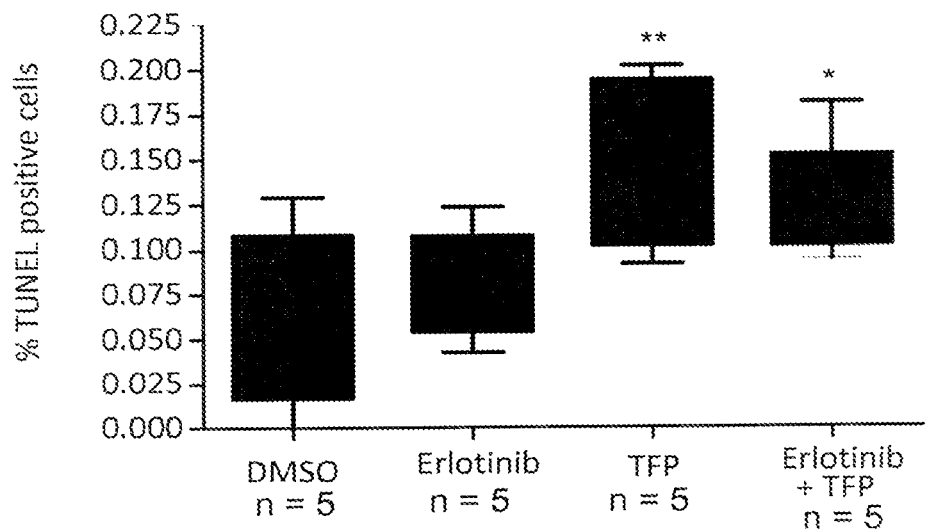
Figure 11G:
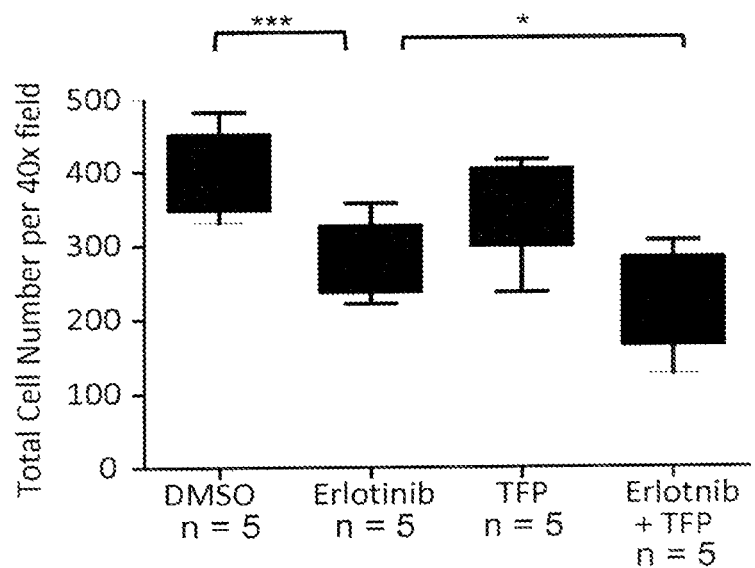
Figure 12:
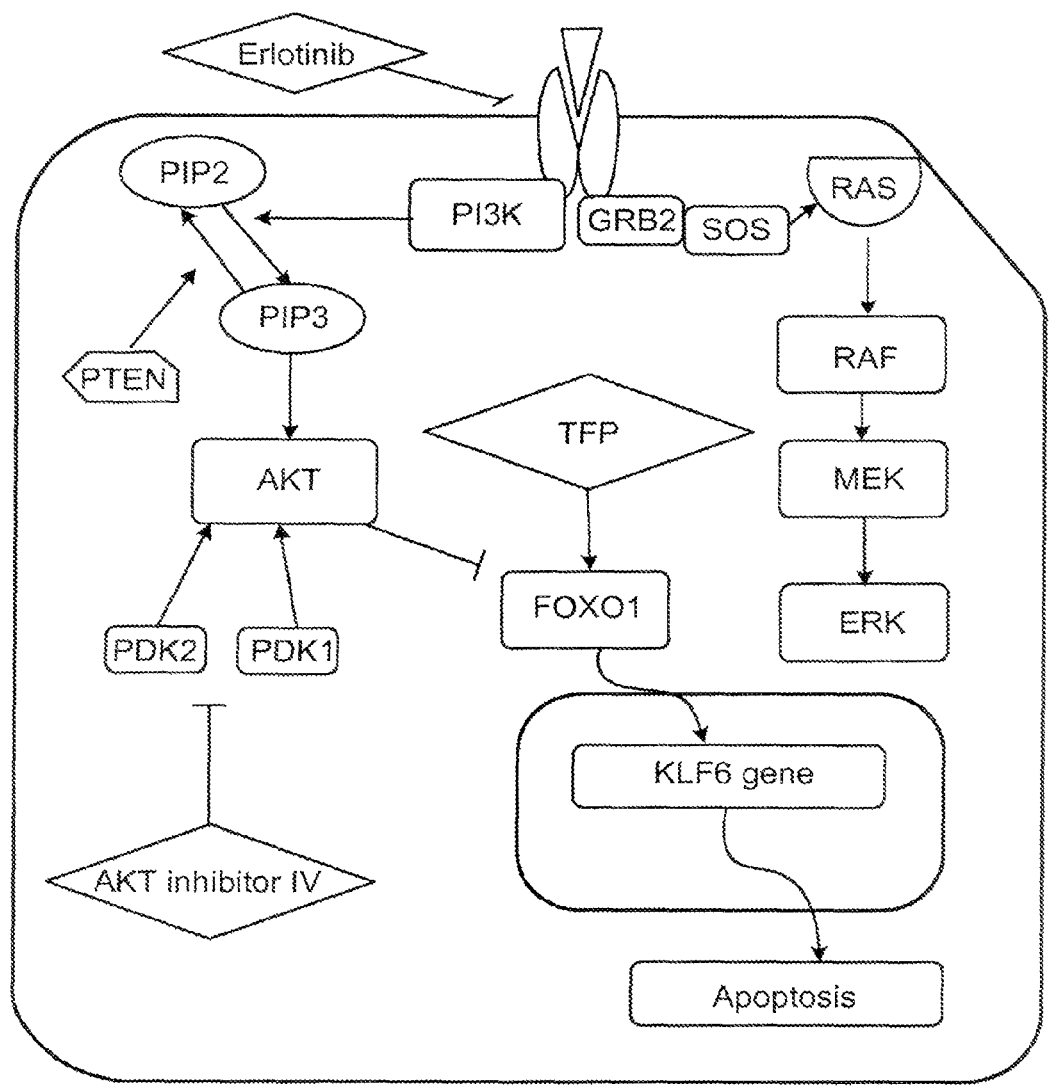
FIG. 12 shows a schematic representation of the EGFR-AKT-FOXO1-KLF6 signaling axes and associated inhibitors utilized to determine functional signaling relationships among the signaling components of the cascade.

The molecular and cellular mechanisms involved in the modulation of Erlotinib and TFP response were also examined in vivo. Analysis of the tumor xenografts derived from each of the four treatment groups demonstrated an increase in apoptosis, as assessed by immunohistochemistry for terminal deoxynucleotidyl transferase dUTP nick end labeling (TUNEL) (FIG. 11f). Evaluation of the proliferative index of each of the treated tumors for expression of proliferating cell nuclear antigen (PCNA) showed a decrease in cell number with erlotinib alone and erlotinib in combination with TFP (FIG. 11g).

Example 9

Chloripramine Exhibits Anti-Proliferative Properties and Causes FOXO1 Nuclear Accumulation The effect of the tricylic (dibenzazapine) antidepressant, chlorimpramine on growth of certain tumor cell lines measured in cell culture. Chlorimpramine exhibited anti-proliferative properties in vitro against the tumor cells lines H1650 (lung; $IC_{50}=\sim 40$ μM), ASPC1 (pancreatic; $IC_{50}=23$ μM), MiaPaca2 (pancreatic; $IC_{50}=17$ μM) and Panc1 (pancreatic; $IC_{50}=16$ μM).

Chloripramine (40 μM) also lead to nuclear accumulation of FOXO1 in H1650 cells. H1650 cells were plated on glass coverslips at a density of 150,000 cells in complete RPMI media. Cells were then fixed in 4% paraformaldehyde at 24-hours post-plating and were incubated with FOXO1 (1:100) primary antibody (Cell Signaling, 9454) for one hour. After incubation with a secondary goat anti-Rabbit IgG (1:1000), (H+L) FITC conjugate (Millipore, P307F), cover slips were mounted with Vectashield DAPI counterstain (H1200) and visualized under fluorescent microscope. A total of 100 cells per condition were counted to determine the distribution of FOXO1 in the cytoplasm vs. the nucleus. All results were confirmed with nuclear cytoplasmic fractionation and western blotting of chloripramine treated cells with a FOXO1 monoclonal antibody. Chloripramine treated cells exhibited a FOXO1 nuclear:cytoplasmic localization ratio of about 60:40, whereas control cells treated with DMSO showed a substantially complete cytoplasmic localization of FOXO1, with little or no detectable localization of FOXO1 to the nucleus.

Example 10

FOXO1 Localization in Circulating Tumor Cells as Pharmacodynamic and Predictive Biomarkers Cells from cancer patients undergoing treatment with tricyclic agents are captured by microfilter and washed with 1 ml PBS and subjected to on-filter immunofluorescence staining or are eluted for staining on glass slides. Cells are fixed with 4% paraformaldehyde for 10 min followed by 30 min blocking and permeabilization with 5% normal goat serum and 0.25% Triton X-100. Cells are then incubated for 1 h with a cocktail of three different primary antibodies against human CD45 (rat monoclonal, Santa Cruz), human cytokeratin (mouse monoclonal, AbCam) and human FOXO1 (rabbit polyclonal, AbCam), followed by incubation for 10 min with a cocktail of Alexa Fluor 488-conjugated goat anti-rat antibody, Alexa Fluor 568 conjugated goat anti-mouse antibody, and Alexa Fluor 647 conjugated goat anti-rabbit antibody, to distinguish tumor cells from leukocytes and to demonstrate FOXO1 cellular localization. A coverslip is then applied with VectaShield mounting medium containing 4',6-diamidino-2-phenylindole (DAPI) for nuclear counterstaining Immunofluorescent images are then obtained using an immunofluorescent microscope equipped with a digital camera interfaced with imaging software. The frequency of circulating tumor cells (CK+ CD45-DAPI+). FOXO1 localization for each CK+DAPI+ CD45-event is then scored: 0=cytoplasmic, 1=nuclear and cytoplasmic, 2=nuclear, A=absent.

Incubation of cancer cells isolated from peripheral blood of patients who are responding to or are predicted to respond to treatment with a tricyclic agent will result in FOXO1 relocalization to the nucleus (greater than 80% of all cells counted). Incubation of cancer cells isolated from peripheral blood of patients who are not responding to or are predicted to not respond to treatment with a tricyclic agent will not result in FOXO1 relocalization to the nucleus.

Example 11

FOXO Localization in Biopsy Material

Direct Biopsy

Biopsy specimens from cancer patients at times pretreatment and post-treatment with a tricyclic agent are used for FOXO1 localization using immunohistochemistry, using FOXO1 antibodies. Slides containing biopsy material either fresh frozen or from paraffin embedded material are deparaffinized with three changes of xylene and rehydrated through graded ethanol washes followed by antigen retrieval in a pressure cooker at 124° C. for 4 min using citrate buffer (10 mM, pH 6.0). Slides are quenched in 0.3% hydrogen peroxide for 10 min and then blocked by incubation in 0.1 M PBS/5% normal goat serum. Slides are incubated overnight at 4° C. in Fox01 (C29H4) Rabbit monoclonal antibody (#2880 Cell Signaling) diluted at 1:100 in PBS/5% BSA. Slides are treated with biotin-labeled anti-rabbit IgG 1:200 in PBS/5% BSA and incubated with preformed avidin biotin peroxidase complex. Metal enhanced diaminobenzidine substrate is added in the presence of horseradish peroxidase. Sections are counter-stained with hematoxylin, dehydrated, and mounted. Quantitation is completed using a cell counter function of ImageJ (http://rsb.info.nih.gov/ij/)

Incubation of cancer cells isolated from peripheral blood with tricyclic agents resulted in FOXO1 relocalization (greater than 80% of all cells counted).

Tumor Derived Explants

Human tumor derived explants from immunodeficient mice treated are with tricyclic agents. Explant material are prepared for FOXO1 localization using immunohistochemistry, using FOXO1 antibodies, as described above.

Treatment with tricyclic agents result in FOXO1 relocalization from a predominantly cytoplasmic distribution in controls (>90% cytoplasmic) to a nuclear predominant staining pattern (>50% nuclear positive staining cells from paraffin embedded material).

These data highlight the involvement of the Ras-Raf-MAPK signaling pathway in the regulation of cellular proliferation and the AKT-PI3K signaling axis in the regulation of cellular survival.

A number of embodiments of the invention have been described. Nevertheless, it will be understood that various modifications may be made without departing from the spirit and scope of the invention. Accordingly, other embodiments are within the scope of the following claims.

What is claimed is:

1. A method for treatment of neoplastic disease comprising administering a subject suffering from said neoplastic disease a first amount of an anti epidermal growth factor receptor (anti-EGFR) agent and one or both of a second amount of an agent that increases activity of Krüppel-like factor 6 (KLF6) and/or a third amount of an agent that increases activity of transcription factor forkhead box O1 (FOXO1) wherein said first and said second and/or third amounts together comprise a therapeutically effective amount of an active combination of agents to treat said neoplastic disease.

2. The method according to claim 1 wherein said neoplastic disease is an EGFR-based neoplasm.

3. The method according to claim 2 wherein said neoplastic disease is non-small cell lung cancer (NSCLC).

4. The method according to claim 3 wherein said anti-EGFR agent is erlotinib.

5. The method according to claim 1 wherein said agent that increases activity of said KLF6 or said FOXO1 increases nuclear accumulation of FOXO1.

6. The method according to claim 5 wherein said agent that increases nuclear accumulation of FOXO1 is a tricyclic agent.

7. The method according to claim 5 wherein said tricyclic agent is a phenothiazine, dibenzazepine or thioxanthene.

8. The method according to claim 6 wherein said tricyclic agent is administered at a dose such that said administration does not lead to a substantial central nervous system effect.

9. The method according to claim 1 wherein said subject is resistant to treatment of said neoplastic disease with said anti-EGFR agent in the absence of treatment with said agent that increases activity of KLF6 or said agent that increases activity of FOXO1.

10. The method according to claim 9 wherein said subject has primary or acquired drug resistance to said anti-EGFR agent.

* * * * *

SEQUENCE LISTING

<160> NUMBER OF SEQ ID NOS: 4

<210> SEQ ID NO 1
<211> LENGTH: 23
<212> TYPE: DNA
<213> ORGANISM: Artificial Sequence
<220> FEATURE:
<223> OTHER INFORMATION: synthetically generated oligonucleotide

```
<400> SEQUENCE: 1
aaggataagg gtgacagcaa cag                                              23

<210> SEQ ID NO 2
<211> LENGTH: 25
<212> TYPE: DNA
<213> ORGANISM: Artificial Sequence
<220> FEATURE:
<223> OTHER INFORMATION: synthetically generated oligonucleotide

<400> SEQUENCE: 2
ttgctgtgta gggacagatt atgac                                            25

<210> SEQ ID NO 3
<211> LENGTH: 20
<212> TYPE: DNA
<213> ORGANISM: Artificial Sequence
<220> FEATURE:
<223> OTHER INFORMATION: synthetically generated oligonucleotide

<400> SEQUENCE: 3
tcctctggag gctgagaaaa                                                  20

<210> SEQ ID NO 4
<211> LENGTH: 20
<212> TYPE: DNA
<213> ORGANISM: Artificial Sequence
<220> FEATURE:
<223> OTHER INFORMATION: synthetically generated oligonucleotide

<400> SEQUENCE: 4
gggctctgga ggaaaagaaa                                                  20
```